US012258393B2

(12) United States Patent
Germinaro et al.

(10) Patent No.: US 12,258,393 B2
(45) Date of Patent: *Mar. 25, 2025

(54) METHOD OF TREATING INFLAMMATORY BOWEL DISEASE WITH A COMBINATION THERAPY OF ANTIBODIES TO IL-23 AND TNF ALPHA

(71) Applicant: Janssen Biotech, Inc., Horsham, PA (US)

(72) Inventors: Matthew Germinaro, Philadelphia, PA (US); Christopher O'Brien, Lafayette Hill, PA (US); Jacqueline Perrigoue, Oreland, PA (US); Marion Vetter, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/325,743

(22) Filed: May 20, 2021

(65) Prior Publication Data

US 2021/0363234 A1 Nov. 25, 2021

Related U.S. Application Data

(60) Provisional application No. 63/116,383, filed on Nov. 20, 2020, provisional application No. 63/028,219, filed on May 21, 2020.

(51) Int. Cl.
*A61K 39/00* (2006.01)
*A61P 1/04* (2006.01)
*A61P 37/02* (2006.01)
*C07K 16/24* (2006.01)

(52) U.S. Cl.
CPC ............. *C07K 16/244* (2013.01); *A61P 1/04* (2018.01); *A61P 37/02* (2018.01); *C07K 16/241* (2013.01); *A61K 2039/505* (2013.01); *C07K 2317/565* (2013.01)

(58) Field of Classification Search
CPC ............................................ A61K 2039/55527
See application file for complete search history.

(56) References Cited

U.S. PATENT DOCUMENTS

| | | |
|---|---|---|
| 3,773,919 A | 11/1973 | Boswell |
| 4,239,754 A | 12/1980 | Bertrand |
| 4,309,989 A | 1/1982 | Fahim |
| 4,399,216 A | 8/1983 | Axel |
| 4,603,106 A | 7/1986 | Cerami |
| 4,634,665 A | 1/1987 | Axel |
| 4,656,134 A | 4/1987 | Ringold |
| 4,668,218 A | 5/1987 | Virtanen |
| 4,676,980 A | 6/1987 | Segal |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,822,776 A | 4/1989 | Cerami |
| 4,873,316 A | 10/1989 | Meade |
| 4,889,818 A | 12/1989 | Gelfand |
| 4,921,794 A | 5/1990 | Tabor |
| 4,925,673 A | 5/1990 | Steiner |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,116,964 A | 5/1992 | Capon |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,538 A | 7/1993 | Capon |
| 5,225,539 A | 7/1993 | Winter |
| 5,231,024 A | 7/1993 | Moeller |
| 5,260,203 A | 11/1993 | Ladner |
| 5,266,491 A | 11/1993 | Nagata |
| 5,304,489 A | 4/1994 | Rosen |
| 5,342,613 A | 8/1994 | Creaven |
| 5,385,839 A | 1/1995 | Stinski |
| 5,403,484 A | 4/1995 | Ladner |
| 5,404,871 A | 4/1995 | Goodman |
| 5,427,908 A | 6/1995 | Dower |
| 5,447,851 A | 9/1995 | Beutler |
| 5,455,030 A | 10/1995 | Ladner |
| 5,457,038 A | 10/1995 | Trinchieri |
| 5,458,135 A | 10/1995 | Patton |
| 5,496,549 A | 3/1996 | Yamazaki |
| 5,514,670 A | 5/1996 | Friedman |
| 5,518,889 A | 5/1996 | Ladner |
| 5,530,101 A | 6/1996 | Queen |
| 5,534,621 A | 7/1996 | Ladner |
| 5,545,806 A | 8/1996 | Lonberg |
| 5,545,807 A | 8/1996 | Surani |

(Continued)

FOREIGN PATENT DOCUMENTS

| | | |
|---|---|---|
| AU | 1764992 A | 10/1992 |
| CL | 6882000 | 3/2000 |

(Continued)

OTHER PUBLICATIONS

US 5,733,746 A, 03/1998, Treco (withdrawn)

(Continued)

*Primary Examiner* — Prema M Mertz
(74) *Attorney, Agent, or Firm* — Riverside Law LLP

(57) ABSTRACT

A method of treating inflammatory bowel disorders, such as ulcerative colitis, comprises administering an IL-23 inhibitor, such as an anti-IL-23p19 antibody (e.g., guselkumab) and a TNF-α inhibitor, such as an anti-TNF-α antibody (e.g., golimumab).

7 Claims, 18 Drawing Sheets

Specification includes a Sequence Listing.

(56) References Cited

U.S. PATENT DOCUMENTS

| | | |
|---|---|---|
| 5,547,852 A | 8/1996 | Seiler |
| 5,565,362 A | 10/1996 | Rosen |
| 5,569,825 A | 10/1996 | Lonberg |
| 5,571,698 A | 11/1996 | Ladner |
| 5,576,195 A | 11/1996 | Robinson |
| 5,580,717 A | 12/1996 | Dower |
| 5,580,734 A | 12/1996 | Treco |
| 5,582,996 A | 12/1996 | Curtis |
| 5,585,089 A | 12/1996 | Queen |
| 5,595,898 A | 1/1997 | Robinson |
| 5,601,819 A | 2/1997 | Wong |
| 5,618,920 A | 4/1997 | Robinson |
| 5,625,126 A | 4/1997 | Lonberg |
| 5,625,825 A | 4/1997 | Rostoker |
| 5,627,052 A | 5/1997 | Schrader |
| 5,633,425 A | 5/1997 | Lonberg |
| 5,637,052 A | 6/1997 | Hirota |
| 5,641,670 A | 6/1997 | Treco |
| 5,643,759 A | 7/1997 | Pfreundschuh |
| 5,643,768 A | 7/1997 | Kawasaki |
| 5,648,467 A | 7/1997 | Trinchieri |
| 5,654,407 A | 8/1997 | Boyle |
| 5,656,272 A | 8/1997 | Le |
| 5,656,730 A | 8/1997 | Lee |
| 5,658,570 A | 8/1997 | Newman |
| 5,658,754 A | 8/1997 | Kawasaki |
| 5,661,016 A | 8/1997 | Lonberg |
| 5,693,493 A | 12/1997 | Robinson |
| 5,693,762 A | 12/1997 | Queen |
| 5,698,195 A | 12/1997 | Le |
| 5,698,417 A | 12/1997 | Robinson |
| 5,698,419 A | 12/1997 | Wolpe |
| 5,698,435 A | 12/1997 | Robinson |
| 5,714,352 A | 2/1998 | Jakobovits |
| 5,723,323 A | 3/1998 | Kauffman |
| 5,733,761 A | 3/1998 | Treco |
| 5,750,105 A | 5/1998 | Newman |
| 5,750,373 A | 5/1998 | Garrard |
| 5,763,192 A | 6/1998 | Kauffman |
| 5,763,733 A | 6/1998 | Whitlow |
| 5,766,886 A | 6/1998 | Studnicka |
| 5,767,260 A | 6/1998 | Whitlow |
| 5,770,198 A | 6/1998 | Coller |
| 5,770,222 A | 6/1998 | Unger |
| 5,770,359 A | 6/1998 | Wilson |
| 5,770,428 A | 6/1998 | Boris-Lawrie |
| 5,780,597 A | 7/1998 | Gately |
| 5,789,650 A | 8/1998 | Lonberg |
| 5,807,706 A | 9/1998 | Carter |
| 5,811,523 A | 9/1998 | Trinchieri |
| 5,814,476 A | 9/1998 | Kauffman |
| 5,814,599 A | 9/1998 | Mitragotri |
| 5,817,483 A | 10/1998 | Kauffman |
| 5,821,333 A | 10/1998 | Carter |
| 5,824,514 A | 10/1998 | Kauffman |
| 5,827,690 A | 10/1998 | Meade |
| 5,827,739 A | 10/1998 | Wilson |
| 5,833,985 A | 11/1998 | Ball |
| 5,837,500 A | 11/1998 | Ladner |
| 5,839,446 A | 11/1998 | Waner |
| 5,849,695 A | 12/1998 | Cohen |
| 5,849,992 A | 12/1998 | Meade |
| 5,851,198 A | 12/1998 | Castellano |
| 5,856,456 A | 1/1999 | Whitlow |
| 5,859,205 A | 1/1999 | Adair |
| 5,871,753 A | 2/1999 | Crabtree |
| 5,879,681 A | 3/1999 | Leone-Bay |
| 5,885,793 A | 3/1999 | Griffiths |
| 5,888,511 A | 3/1999 | Skurkovich |
| 5,891,680 A | 4/1999 | Lieschke |
| 5,919,452 A | 7/1999 | Le |
| 5,932,448 A | 8/1999 | Tso |
| 5,958,413 A | 9/1999 | Anagnostopulos |
| 5,959,083 A | 9/1999 | Bosslet |
| 5,959,084 A | 9/1999 | Ring |
| 5,962,255 A | 10/1999 | Griffiths |
| 5,976,862 A | 11/1999 | Kauffman |
| 5,989,530 A | 11/1999 | Lorenz |
| 5,993,833 A | 11/1999 | De Lacharriere |
| 5,994,616 A | 11/1999 | Rosen |
| 6,010,902 A | 1/2000 | Ledbetter |
| 6,017,732 A | 1/2000 | Jespers |
| 6,037,453 A | 3/2000 | Jardieu |
| 6,060,284 A | 5/2000 | Bazan |
| 6,060,285 A | 5/2000 | Lenz |
| 6,086,876 A | 7/2000 | Karp |
| 6,106,833 A | 8/2000 | Ring |
| 6,132,992 A | 10/2000 | Ledbetter |
| 6,180,370 B1 | 1/2001 | Queen |
| 6,190,691 B1 | 2/2001 | Mak |
| 6,193,967 B1 | 2/2001 | Morganelli |
| 6,204,023 B1 | 3/2001 | Robinson |
| 6,210,668 B1 | 4/2001 | Lindhofer |
| 6,225,117 B1 | 5/2001 | Gately |
| 6,277,969 B1 | 8/2001 | Le |
| 6,284,471 B1 | 9/2001 | Le |
| 6,300,478 B1 | 10/2001 | Trinchieri |
| 6,338,848 B1 | 1/2002 | Leonard |
| 6,479,634 B1 | 11/2002 | Bazan |
| 6,495,667 B1 | 12/2002 | Bazan |
| 6,610,285 B1 | 8/2003 | Hirata |
| 6,756,481 B2 | 6/2004 | Chirica |
| 6,800,460 B1 | 10/2004 | Oppmann |
| 6,835,825 B1 | 12/2004 | Bazan |
| 6,902,734 B2 | 6/2005 | Giles-Komar |
| 6,914,128 B1 | 7/2005 | Salfeld |
| RE39,015 E | 3/2006 | Bazan |
| 7,063,964 B2 | 6/2006 | Giles-Komar |
| 7,090,847 B1 | 8/2006 | Oppmann |
| 7,166,285 B2 | 1/2007 | Giles-Komar |
| 7,183,382 B2 | 2/2007 | Oppmann |
| 7,247,711 B2 | 7/2007 | Benson |
| 7,252,971 B2 | 8/2007 | Benson |
| 7,279,157 B2 | 10/2007 | Giles-Komar |
| 7,282,204 B2 | 10/2007 | Oft |
| 7,491,391 B2 | 2/2009 | Benson |
| 7,521,206 B2 | 4/2009 | Heavner |
| 7,560,247 B2 | 7/2009 | Giles-Komar |
| 7,691,378 B2 | 4/2010 | Heavner |
| 7,807,414 B2 | 10/2010 | Benson |
| 7,887,807 B2 | 2/2011 | Giles-Komar |
| 7,935,344 B2 | 5/2011 | Benson |
| 7,993,645 B2 | 8/2011 | Benson |
| 8,084,233 B2 | 12/2011 | Giles-Komar |
| 8,106,177 B2 | 1/2012 | Benson |
| 8,221,760 B2 | 7/2012 | Benson |
| 8,241,899 B2 | 8/2012 | Heavner |
| 8,329,171 B2 | 12/2012 | Giles-Komar |
| 8,703,141 B2 | 4/2014 | Giles-Komar |
| 9,353,181 B2 | 5/2016 | Benson |
| 9,353,645 B1 | 5/2016 | Kennedy |
| 9,409,984 B2 | 8/2016 | Giles-Komar |
| 9,512,065 B2 | 12/2016 | Northen |
| 9,676,848 B2 | 6/2017 | Giles-Komar |
| 9,783,607 B2 | 10/2017 | Benson |
| 10,030,070 B2 | 7/2018 | Benson |
| 10,259,867 B2 | 4/2019 | Giles-Komar |
| 10,519,231 B2 | 12/2019 | Giles-Komar |
| 10,961,307 B2 | 3/2021 | Johanns |
| 2002/0042386 A1 | 4/2002 | Rosen |
| 2002/0168360 A1 | 11/2002 | Dingivan |
| 2003/0003097 A1 | 1/2003 | Reff |
| 2003/0124617 A1 | 7/2003 | Gram |
| 2003/0162261 A1 | 8/2003 | Oppmann |
| 2004/0185506 A1 | 9/2004 | Heavner |
| 2004/0258686 A1 | 12/2004 | Chirica |
| 2005/0049402 A1 | 3/2005 | Babcook |
| 2005/0053598 A1 | 3/2005 | Burke |
| 2005/0175611 A1 | 8/2005 | Mahler |
| 2005/0208052 A1 | 9/2005 | Katsikis |
| 2005/0244874 A1 | 11/2005 | Kastelein |
| 2007/0048315 A1 | 3/2007 | Presta |
| 2008/0311043 A1 | 12/2008 | Hoffman |
| 2009/0028794 A1 | 1/2009 | Medich |

(56) References Cited

U.S. PATENT DOCUMENTS

| | | |
|---|---|---|
| 2009/0181027 A1 | 7/2009 | Dal Monte |
| 2009/0214528 A1 | 8/2009 | Dorai |
| 2010/0266590 A1 | 10/2010 | Demetri |
| 2010/0322863 A1 | 12/2010 | Benson |
| 2011/0160085 A1 | 6/2011 | Li |
| 2011/0319292 A1 | 12/2011 | Benson |
| 2014/0356357 A1 | 12/2014 | Ariaans |
| 2015/0147337 A1 | 5/2015 | Reichert |
| 2016/0122429 A1 | 5/2016 | Millican |
| 2017/0081402 A1 | 3/2017 | Boecher |
| 2017/0218092 A1 | 8/2017 | Chiu |
| 2018/0036379 A1 | 2/2018 | Chevrier |
| 2018/0252728 A1 | 9/2018 | Georgantas, III |
| 2019/0269757 A1 | 9/2019 | Adedokun |
| 2019/0345245 A1 | 11/2019 | Drevets |
| 2020/0062841 A1 | 2/2020 | Giles-Komar |
| 2020/0262908 A1 | 8/2020 | Jones |
| 2020/0369761 A1 | 11/2020 | Germinaro |
| 2021/0171622 A1 | 6/2021 | Johanns |
| 2021/0363234 A1 | 11/2021 | Germinaro |
| 2022/0372129 A1 | 11/2022 | Germinaro |

FOREIGN PATENT DOCUMENTS

| | | |
|---|---|---|
| EP | 0003089 | 7/1979 |
| EP | 229246 | 10/1986 |
| EP | 0218868 A2 | 4/1987 |
| EP | 0350690 A2 | 1/1990 |
| EP | 368684 | 5/1990 |
| EP | 371998 | 6/1990 |
| EP | 0380068 A1 | 8/1990 |
| EP | 0393438 A2 | 10/1990 |
| EP | 0433900 A1 | 6/1991 |
| EP | 0438474 | 7/1991 |
| EP | 0237507 B1 | 12/1991 |
| EP | 0463151 | 1/1992 |
| EP | 0525570 A2 | 2/1993 |
| EP | 0526905 A3 | 5/1993 |
| EP | 550400 | 7/1993 |
| EP | 0229246 B1 | 8/1993 |
| EP | 0260610 B1 | 9/1993 |
| EP | 0288088 B1 | 3/1994 |
| EP | 0368684 B1 | 3/1994 |
| EP | 0371998 B1 | 3/1994 |
| EP | 0590689 A2 | 4/1994 |
| EP | 0229046 B1 | 5/1994 |
| EP | 614989 A1 | 9/1994 |
| EP | 0212489 B1 | 11/1994 |
| EP | 0308378 B1 | 11/1994 |
| EP | 0412486 B1 | 11/1994 |
| EP | 0398327 B1 | 3/1995 |
| EP | 0640689 | 3/1995 |
| EP | 0438474 B1 | 5/1996 |
| EP | 0710719 A1 | 5/1996 |
| EP | 0463151 B1 | 6/1996 |
| EP | 0550400 B1 | 7/1996 |
| EP | 790255 | 8/1997 |
| EP | 0814259 | 12/1997 |
| EP | 433827 | 3/1998 |
| EP | 0351789 B1 | 11/1998 |
| EP | 0486526 B2 | 3/2001 |
| EP | 0610201 B1 | 5/2001 |
| EP | 804581 | 9/2001 |
| EP | 1137766 | 9/2005 |
| EP | 0710719 B1 | 3/2007 |
| EP | 2870137 B1 | 5/2018 |
| GB | 2272440 A | 5/1994 |
| JP | 11127855 A | 5/1999 |
| JP | 2009523012 | 6/2009 |
| JP | 2016505572 | 2/2016 |
| WO | 8605803 A1 | 10/1986 |
| WO | 8806630 A1 | 9/1988 |
| WO | 8906283 A1 | 7/1989 |
| WO | 9000902 A1 | 2/1990 |
| WO | 9003809 A1 | 4/1990 |
| WO | 9004036 A1 | 4/1990 |
| WO | 9005147 | 5/1990 |
| WO | 9005370 A1 | 5/1990 |
| WO | 1990005370 | 5/1990 |
| WO | 9014424 A1 | 11/1990 |
| WO | 9014430 A1 | 11/1990 |
| WO | 9014443 A1 | 11/1990 |
| WO | 9100360 A1 | 1/1991 |
| WO | 9102078 A1 | 2/1991 |
| WO | 9109967 A1 | 7/1991 |
| WO | 9117271 A1 | 11/1991 |
| WO | 9118980 A1 | 12/1991 |
| WO | 9119818 A1 | 12/1991 |
| WO | 9200373 A1 | 1/1992 |
| WO | 1992001047 A1 | 1/1992 |
| WO | 9203461 A1 | 3/1992 |
| WO | 1992003461 | 3/1992 |
| WO | 9205256 | 4/1992 |
| WO | 9205258 A1 | 4/1992 |
| WO | 9206204 A1 | 4/1992 |
| WO | 9207076 A1 | 4/1992 |
| WO | 1992006204 | 4/1992 |
| WO | 9211272 A1 | 7/1992 |
| WO | 9211383 A1 | 7/1992 |
| WO | 1992011272 | 7/1992 |
| WO | 9213095 A1 | 8/1992 |
| WO | 9214843 A1 | 9/1992 |
| WO | 9216221 A1 | 10/1992 |
| WO | 9216553 A1 | 10/1992 |
| WO | 9218619 A1 | 10/1992 |
| WO | 1992020791 A1 | 11/1992 |
| WO | 9302108 A1 | 2/1993 |
| WO | 9308278 A1 | 4/1993 |
| WO | 1993006213 A1 | 4/1993 |
| WO | 9308829 A1 | 5/1993 |
| WO | 9311383 A1 | 6/1993 |
| WO | 1993011236 A1 | 6/1993 |
| WO | 1993019172 A1 | 9/1993 |
| WO | 9406498 A1 | 3/1994 |
| WO | 9408552 A2 | 4/1994 |
| WO | 9416970 A1 | 8/1994 |
| WO | 9418219 A1 | 8/1994 |
| WO | 1994018219 | 8/1994 |
| WO | 9425585 A1 | 11/1994 |
| WO | 9501538 A1 | 1/1995 |
| WO | 1995001438 | 1/1995 |
| WO | 9516027 A1 | 6/1995 |
| WO | 1995015388 | 6/1995 |
| WO | 9607754 A1 | 3/1996 |
| WO | 9613583 A2 | 5/1996 |
| WO | 9619256 A1 | 6/1996 |
| WO | 9633735 | 10/1996 |
| WO | 9634096 A1 | 10/1996 |
| WO | 9708320 A1 | 3/1997 |
| WO | 9713852 A1 | 4/1997 |
| WO | 9715327 | 5/1997 |
| WO | 9720032 A1 | 6/1997 |
| WO | 9722376 A1 | 6/1997 |
| WO | 1997020032 | 6/1997 |
| WO | 9725086 | 7/1997 |
| WO | 9729131 A1 | 8/1997 |
| WO | 9801757 A1 | 1/1998 |
| WO | 1998001757 | 1/1998 |
| WO | 9824884 A1 | 6/1998 |
| WO | 9824893 A1 | 6/1998 |
| WO | 9835888 A1 | 8/1998 |
| WO | 9850433 A2 | 11/1998 |
| WO | 9853847 A1 | 12/1998 |
| WO | 9905280 | 2/1999 |
| WO | 9906834 A2 | 2/1999 |
| WO | 1999006834 | 2/1999 |
| WO | 9937682 | 7/1999 |
| WO | 9940195 | 8/1999 |
| WO | 9954342 A1 | 10/1999 |
| WO | 0009552 | 2/2000 |
| WO | 0034459 | 6/2000 |
| WO | 0053631 | 9/2000 |
| WO | 0056772 | 9/2000 |
| WO | 0070049 | 11/2000 |

(56) References Cited

FOREIGN PATENT DOCUMENTS

| | | |
|---|---|---|
| WO | 0212500 A2 | 2/2001 |
| WO | 0118051 | 3/2001 |
| WO | 0119373 | 3/2001 |
| WO | 0185790 | 11/2001 |
| WO | 0212502 A2 | 2/2002 |
| WO | 03011878 A2 | 2/2003 |
| WO | 2004042009 | 5/2004 |
| WO | 2004058178 | 7/2004 |
| WO | 2004071517 | 8/2004 |
| WO | 2004081190 | 9/2004 |
| WO | 2004101750 | 11/2004 |
| WO | 2005103083 | 11/2005 |
| WO | 2005108425 | 11/2005 |
| WO | 2007024846 | 3/2007 |
| WO | 2007076524 | 7/2007 |
| WO | 2008016633 | 2/2008 |
| WO | 2010056399 A1 | 5/2010 |
| WO | 2011070339 | 6/2011 |
| WO | 2013087911 | 6/2013 |
| WO | 2014004436 | 1/2014 |
| WO | 2014006414 A1 | 1/2014 |
| WO | 2014140509 A1 | 9/2014 |
| WO | 2015119841 A1 | 8/2015 |
| WO | 2017048901 | 3/2017 |
| WO | 2017049035 | 3/2017 |
| WO | 2017136524 | 8/2017 |
| WO | 2017172771 | 10/2017 |
| WO | 2018218215 A1 | 11/2018 |
| WO | 2019090078 | 5/2019 |
| WO | 2019090329 | 5/2019 |
| WO | 2019191464 | 10/2019 |
| WO | 2020183269 | 9/2020 |
| WO | 2020234834 | 11/2020 |
| WO | 2021234634 | 11/2021 |

OTHER PUBLICATIONS

Liang, Chi-Ming et al., "Production and Characterization of Monoclonal Antibodies Against Recombinant Human Tumor Necrosis Factor/Cachectin," Biochemistry & Biophysics Research Communication, vol. 137, No. 2 (1986), pp. 847-854.
Lis et al., 2014, "Tumor necrosis factor inhibitors—state of knowledge." Arch Med Sci. Dec. 22; 10(6): 1175-1185.
Liu et al., 2015, "Association analyses identify 38 susceptibility loci for inflammatory bowel disease and highlight shared genetic risk across populations. "Nature Genetics vol. 47, pp. 979-986.
Loetscher et al., "Molecular Cloning and Expression of the Human 55 kd Tumor Necrosis Factor Receptor", Cell, vol. 61 (1990), pp. 351-359.
Loftus, et al., "Epidemiology of inflammatory bowel disease," Gastroenterology Clinics of North America, 31:1-20 (2002).
Lonberg et al. "Antigen-specific human antibodies from mice comprising four distinct genetic modifications", Nature, vol. 368 (1994), pp. 856-859.
Lonberg et al., "Human Antibodies from Transgenic Mice", International Reviews of Immunology, vol. 13, No. 1 (1995), pp. 65-93.
Lowenberg et al. "Golimumab for the treatment of ulcrative colitis." Clinical and Experimental Gastroenterology, 4:7, pp. 53-59, 2014.
Lucas, R. et al., "Generation and characterization of a neutralizing rat anti-rm TNF-a monoclonal antibody," Immunology, 71:218-223 (1990).
M. J. Page and M. A. Sydenham, "High Level Expression of the Humanized Monoclonal Antibody Campath-1H in Chinese Hamster Ovary Cells", Biotechnology, vol. 9 (1991), pp. 64-68.
Ma et al., "Immunotherapeutic potential of antibodies produced in plants", Trends in Biotechnology, vol. 13 (1995), pp. 522-527.
Ma et al., "Plant Antibodies for Immunotherapy", Plant Physiology, vol. 109 (1995), pp. 341-346.
Maguire van Seventer, et al., "Interferon-☐ differentially regulates expression of the IL-12 family members p35, p40, p19 and EB13 in activated human dendritic cells," Journal of Neuroimmunology, 133: 60-71 (2002).

Marrack et al, "The Staphylococcal Enterotoxins and Their Relatives", Science, vol. 248 (1990), pp. 705-711.
Meager, Anthony et al., "Preparation and Characterization of Monoclonal Antibodies Directed Against Antigenic Determinants of Recombinant Human Tumour Necrosis Factor (rTNF)," Hybridoma, vol. 6, No. 3 (1987), pp. 305-311.
Mease PJ, Antoni CE, Gladman DD, Taylor WJ. Psoriatic arthritis assessment tools in clinical trials. Ann Rheum Dis. 2005;64(Suppl II):ii49-ii54.
Mease PJ, Kivitz AJ, Burch FX, et al. Etanercept treatment of psoriatic arthritis: safety, efficacy, and effect on disease progression. Arthritis Rheum. 2004;50(7):2264-2272.
Mendez, et al., "Functional transplant of megabase human immunoglobulin loci recapitulates human antibody response in mice," Nature Genetics, vol. 15, No. 2 (1997), pp. 146-156.
Milstein, et al., "Hybrid hybridomas and their Use in Immunohistochemistry," Nature, vol. 305 (1983), pp. 537-540.
Mocellin et al., "Tumor necrosis factor, cancer and anticancer therapy", Cytokine Growth Factor Rev. Feb. 2005; 16(1) 35-53, Epub Dec. 19, 2004.
Moller, Achim et al., "Monoclonal Antibodies to Human Tumor Necrosis Factor a: In Vitro and In Vivo Application," Cytokine, vol. 2, No. 3 (1990), pp. 162-169.
Morrison, Sherie L., "Transfectomas Provide Novel Chimeric Antibodies," Science, 229:1202-1207(1985).
Muller, "Determination of Affinity and Specificity of Anti-Hapten Antibodies by Competitive Radioimmunoassay", Meth. Enzymol., 92:589-601 (1983).
Murphy, et al., "Divergent pro- and anti-inflammatory roles for IL-23 and IL-12 in Joint autoimmune inflammation," Journal of Experimental Medicine, 198(12): 1951-1957 (2003).
Murphy, et al., "Matrix metalloproteinase degradation of elastin, type IV collagen and proteoglycan", Biochem. J., vol. 277 (1991), pp. 277-279.
Nagai, M. et al., "Antibody to tumor necrosis factor (TNF) reduces endotoxin fever," Experientia, 44:606-607 (1988).
NCT03662542, "A Study of Efficacy and Safety of Combination Therapy with Guselkumab and Golimumab in Participants with Moderatly to Severely Active Ulcerative Colitis (VEGA)" ClinicalTrials.gov, Sep. 7, 2018.
Neuberger, M., "Generating high-avidity human Mabs in mince", Nature Biotechnology, vol. 14 (1996), p. 826.
Neurath et al., "Antibodies to Interleukin 12 Abrogate Established Experimental Colitis in Mice," Journal of Experimental Medicine, 182(5):1281-1290 (1995).
Nguyen et al., "Production of Human Monoclonal Antibodies in SCID Mouse", Microbiology and Immunology, vol. 41 (1997), pp. 901-907.
Nophar, Yaron et al., "Soluble forms of tumor necrosis factor receptors (TNF-Rs). The cDNA for the type 1 TNF-R, cloned using amino acid sequence data of its soluble form, encodes both the cell surface and a soluble form of the receptor," The EMBO Journal, 9(10):3269-3278(1990).
Opal, Steven M. et al., "Efficacy of a Monoclonal Antibody Directed Against Tumor Necrosis Factor in Protecting Neutropenic Rats from Lethal Infection with Pseudomonas aeruginosa," J. of Infectious Diseases, 161:1148-1152 (1990).
Oppmann, et al., "Novel p19 Protein Engages IL-12p40 to Form a Cytokine, IL-23, with Biological Activities Similar as Well as Distinct from IL-12," Immunity, 13: 715-725 (2000).
Panaccione, et al., "Briakinumab or Treatment of Crohn's Disease: Results of a Randomized Trial," Inflammatory Bowel, 21: 1329-1340 (2015).
Papp, et al., Efficacy and Safety of Ustekinumab, A Human Interleukin-12/23 Monoclonal Antibody, in Patients with Psoriasis: 52 Week Results from a Randomised, Double-Blind, Placebo-Controlled Trial (PHOENIX 2), The Lancet, 371: 1675-1684 (2008).
Parham, et al., "A Receptor for the Heterodimeric Cytokine IL-23 is Composed of IL-12R☐1 and a Novel Cytokine Receptor Subunit, IL-23R," The Journal of Immunology, 168: 5699-5708 (2002).
Parrillo, Joseph E., "Pathogenetic Mechanisms of Septic Shock," N.E. Journal of Medicine, 328(20):1471-1477 (1993).

(56) References Cited

OTHER PUBLICATIONS

Partsch G, Steiner G, Leeb BF, Dunky A, Broil H, Smolen JS. Highly increased levels of tumor necrosis factor-alpha and other proinflammatory cytokines in psoriatic arthritis synovial fluid. J Rheumatol. 1997;24(3):518-523.
Paulus, H., A Preparation and Biomedical Applications of Bispecific Antibodies®, Behring Inst. Mitt, No. 78:118-132 (1985).
PCT Search Report, PCT/IB/19/58098, dated Jan. 13, 2020. 10 pages.
Pennington, James, "TNF: Therapeutic Target in Patients with Sepsis," ASM News, 58(9):479-482(1992).
Peppel et al., "A Tumor Necrosis Factor (TNF) Receptor-IgG Heavy ChainChimeric Protein as a Bivalent Antagonist of TNF Activity", Journal of Experimental Medicine, vol. 174 (1991), pp. 1483-1489.
Peter J. Barnes, "Cytokine-directed therapies for the treatment of chronic airway diseases," Cytokine & Growth Factor Reviews 14 (2003): 511-522 (2003).
Pham T, Guillemin F, Claudepierre P, et al. TNFa antagonist therapy in ankylosing spondylitis and psoriatic arthritis: recommendations of the French Society for Rheumatology. Joint Bone Spine. 2006;73:547-553.
Piguet, Pierre-Francois et al., "Tumor Necrosis Factor/Cachectin is an Effector of Skin and Gut Lesions of the Acute Phase of Graft-vs.-Host Disease," J. Exp. Med., 166:1280-1289 (1987).
Portolano, et al., "Lack of Promiscuity in Autoantigen-Specific H and L Chain Combinations as Revealed by Human H and L Chain 'Roulette'," Journal of Immunology, 150(3): 880-887 (1993).
Powell et al., "Gel Microdroplets and Flow Cytometry: Rapid Determination of Antibody Secretion by Individual Cells Within a Cell Population", Biotechnology, vol. 8 (1990), pp. 333-337.
Presta et al., "Humanization of an Antibody Directed Against IgE", Journal of Immunology, vol. 151 (1993), p. 2623.
Riechmann, et al., "Reshaping human antibodies for therapy," Nature, vol. 332 (1988), pp. 323-327.
Van Riel PL, van Gestel AM, Scott DL, for the EULAR Standing Committee for International Clinical Studies Including Therapeutic Trials—ESCISIT. EULAR Handbook of Clinical Assessments in Rheumatoid Arthritis. Alphen Aan Den Rijn, The Netherlands: Van Zuiden Communications B.V.; 2000:40.
Veale DJ, Markham T, Fearon U, et al. St Vincents University Hospital, Dublin, Ireland. Therapy in psoriasis and psoriatic arthritis: anti-TNF-alpha clinical and angiogenic responses. Arthritis Rheum. 2003;48(suppl):S168-S169.
Verhoef, J. and Torensma, R., "Prospects for Monoclonal Antibodies in the Diagnosis and Treatment of Bacterial Infections," Eur. J. Clin. Microbiol. Dis., 9(4):247-250 (1990).
Verhoeyen et al., "Reshaping Human Antibodies:Grafting an Antilysozyme Activity", Science, vol. 239 (1988), p. 1534.
Von Asmuth, E.J.U. et al., "Tumour Necrosis Factor Alpha (TNF-a) and Interleukin 6 in a Zymosan-Induced Shock Model," Scand. J. Immunol., 32:313-319 (1990).
Waldmann, Thomas A., "Monoclonal Antibodies in Diagnosis and Therapy," Science, 252:1657-1662(1991).
Ware JE Jr, Sherbourne CD. The MOS 36 item short form health survey (SF 36), I. Conceptual framework and tem selection. Med Care. 1992;30(6):473 483.
Ware JE, Kosinski M, Keller SD. Interpretation: NormBased. In: SF-36 Physical and Mental Health Summary Scales: A User's Manual. Boston, MA: The Health Institute; 1994:8:1-8:42.
Wen et al., "Limiting diluation assay for human B cells based on their activation by mutant EL4 thymoma cells:total and antimalaria responder B cell frequencies" Journal of Immunology, vol. 17 (1987), pp. 887-892.
Werlen et al., "Site-Specific Conjugation of an Enzyme and an Antibody Fragment", Bioconjugate Chemistry, vol. 5 (1994), pp. 411-417.
Whitelam, et al., "Antibody production in transgenic plants," Biochemical Society Transactions, Transgenic Plants and Plan Biochemistry, vol. 22 (1994), pp. 940-944.
Whittle, Nigel, et al., "Construction and Expression of a CDR-Grafted Anti-TNF Antibody," J. Cell Blochem, Supl. 13A:96 (1989).
Wiekowski, et al., "Ubiquitous Transgenic Expression of the IL-23 Subunit p19 Induces Multiorgan Inflammation, Runting, Infertility, and Premature Death," Journal of Immunology, 166: 7563-7570 (2001).
Wiendl, et al., "Therapeutic Approaches in Multiple Sclerosis: Lessons from Failed and Interrupted Treatment Trials," BioDrugs, 16(3): 183-200 (2002).
William J. Sandborn et al: "Ustekinumab Induction and Maintenance Therapy in Refractory Crohn's Disease", The New England Journal of Medicine, vol. 367, No. 16, Oct. 18, 2012 (Oct. 18, 2012), pp. 1519-1528, XP055414033, US ISSN: 0028-4793, DOI: 10.1 056/NEJMoa1203572.
Winter et al., "Antibody-based Therapy", Immunology Today, 14(6), pp. 243-246 (1993).
Wood et al, "Staphylococcal enterotoxins and the immune system", FEMS Microbiology Immunology, vol. 76 (1991), pp. 121-134.
Yadav, et al., "Cytokines and autoimmunity: redundancy defines their complex nature," Current Opinion in Immunology, 15: 697-703 (2003).
Yen et al., "IL-23 is essential for T cell-mediated colitis and promoted inflammation via IL-17 and IL-6," The Journal of Clinical Investigation, 116(5):1310-1316 (2006).
Yu et al., "Expression of Interleukin-22/STAT3 signaling pathway in ulcerative colitis and related carcinogenesis," World Journal of Gastroenterology, 19(17):2638-2649 (2013).
Zhuang et al., 2010, Pharmacokinetics of Golimumab, an Anti-TNFalpha Human Monoclonal Antibody After Multiple Subcutaneous or Intravenous Injections in Subjects with Rheumatoid Arthritis Clinical Pharmacology & Therapeutics, vol. 87, Supplement 1, PI-80, p. S34-S35.
Zochling J, van der Heijde D, Burgos-Vargas R, et al. ASAS/EULAR recommendations for the management of ankylosing spondylitis. Ann Rheum Dis. 2006;65(4):442-452.
Acosta Felquer et al., "Drug therapies for peripheral joint disease in psoriatic arthritis: a systematic review", Journal of Rheumatology, (Nov. 30, 2014), vol. 41, No. 11, doi:10.3899/jrheum. 140876, ISSN 0315-162X, pp. 2277-2285, XP055622320.
Adedokun, et al, "Ustekinumab Pharmacokinetics and Exposure Response in a Phase 3 Randomized Trial of Patients with Ulcerative Colitis," Clinical Gastroenterology and Hepatology, 18: 2244-2255 (2020).
Adedokun, OJ, et al. Pharmacokinetics and Exposure Relationships of Ustekinumab in Patients With Crohn's Disease. Gastroenterology, May 2018; vol. 154; pp. 1660-1671.
Aderka, Dan et al., "IL-6 Inhibits Lipopolysaccharide-Induced tumor Necrosis Factor Production in Cultured Human Monocytes, U937 Cells, and in Mice," J Immunol, 143:3517-3523(1989).
Aderka, Dan et al., "The Possible Role of Tumor Necrosis Factor (TNF) and Its Natural Inhibitors, The Soluble-TNF Receptors, In Autoimmune Diseases," Israel J. Med. Scl., 28(2):126-130 (1992).
Aderka, Dan, "Role of Tumor Necrosis Factor in the Pathogenesis of Intravascular Coagulopathy of Sepsis: Potential New Therapeutic Implications," IsrJ Med Scl, 27:52-60 (1991).
Aggarwal, Bharat B. et al., "Human Tumor Necrosis Factor Production, Purification and Characterization," J. of Biol. Chem., 260(4):2345-2354 (1985).
Aggarwal, et al., "Interleukin-23 Promotes a Distinct CD4 T Cell Activation State characterized by the Production of Interleukin-17," The Journal of Biological Chemistry, 278(3): 1910-1914 (2003).
Ahern et al., "Interleukin-23 Drives Intestinal Inflammation through Direct Activity on T Cell," Immunity. 33(2):279-288 (2010).
Akama, Hideto et al., "Mononuclear Cells Enhance Prostaglandin E2 Production of Polymorphonuclear Leukocytes via Tumor Necrosis Factor a," Biochemical and Biophysical Research Comm., 168(2):857-862 (1990).
Alex Hoffman, "Prefilled syringes point to the future," Beremans Limited, 1-4 (2004).
Allocca et al, Best Practice & Research Clinical Gastroenterology, Apr. 2018, vol. 32-33, pp. 95-102.

(56) References Cited

OTHER PUBLICATIONS

Allocca, et al., "Can IL-23 be a good target for ulcerative colitis?" Best Practice & Research Clinical Gastroenterology, 32-33: 95-102 (2018).

Alt, et al., "Selective Multiplication of Dihydrofolate Reductase Genes in Methotrexate-resistant Variants of Cultured Murine Cells", Journal of Biological Chemistry, vol. 253 (1978), pp. 1357-1370.

Anderson et al., "Meta-analysis identifies 29 additional ulcerative colitis risk loci, increasing the number of confirmed associations to 47," Nature Genetics, 43(3):246-252 (2011).

Anonymous, "Australian Public Assessment Report for golimumab (rmc) SIMPONI", Product report, (20140500), p. 11, URL: https://www.tga.gov.au/sites/default/files/auspar-golimumab-140519.pdf, (Jul. 17, 2020), XP055761798.

Anonymous, "History of Changes for Study NCT02181673", submitted Jan. 23, 2017,https://clinicaltrials.gov/ct2/history/NCT02181673?V _30=View#StudyPageTop.

Ashkenazi et al., 1991, "Protection against endotoxic shock by a tumor necrosis factor receptor immunoadhesin," Proc. Natl. Acad. Sci. USA, 88(23): 10535-10539.

Babcook et al., "A novel strategy for generating monoclonal antibodies from single, isolated lymphocytes producing antibodies of defined specificities", Proc. Natl. Acad. Sci. USA , vol. 93 (1996), pp. 7843-7848.

Baker et al., "Control of established experimental allergic encephalomyelitis by inhibition of tumor necrosis factor (TNF) activity within the central nervous system using monoclonal antibodies and TNF receptor-immunoglobulin fusion proteins", European Journal of Immunology, vol. 24 (1994), pp. 2040-2048.

Barrie, et al., "The interleukin-12 family of cytokines: Therapeutic targets for inflammatory disease mediation," Clinical and Applied Immunology Reviews, 5: 225-240 (1995).

Basra MKA, Fenech R, Gatt RM, Salek MS, Finlay AY. The Dermatology Life Quality Index 1994-2007: a comprehensive review of validation data and clinical results. Br J Rheumatol. 2008;159:997-1035.

Baumgart, et al., "Crohn's Disease," Lancet, 380: 1590-1605 (2012).

Bebbington, et al., "High-Level Expression of a Recombinant Antibody from Myeloma Cells Using a Glutamine Systhetase Gene as an Amplifiable Selectable Marker", Bio/Technology, vol. 10 (1992), pp. 169-175.

Belladonna, et al., "IL-23 and IL-12 Have Overlapping, but Distinct, Effects on Murine Dendritic Cells," The Journal of Immunology, 168: 5448-5454 (2002).

Berg et al., "Enterocolitis and Colon Cancer in Interleukin-10-deficient Mice are Associated with Aberrant Cytokine Production and CD4+ TH1-like Responses," Journal of Clinical Investigations, 98:1010-1020 (1996).

Berkow et al., Eds, The Merck Manual of Diagnosis and Therapy, Sixteenth Edition, Merck Research Laboratories, Rahway, NJ 1992 p. 1263-1287.

Beutler, B. et al., "Identity of tumour necrosis factor and the macrophage-secreted factor cachectin," Nature, 316:552-554 (1985).

Beutler, B. et al., "Passive Immunization Against Cachectin/Tumor Necrosis Factor Protects Mice from Lethal Effect of Endotoxin," Science, 229:869-871 (1985).

Beutler, B. et al., "Purification of Cachectin, A Lipoprotein Lipase-Suppressing Hormone Secreted by Endotoxin-Induced RAW 264.7 Cells," J. Exp. Med., 161:984-995 (1985).

Bodmer, Mark, "Humanized Antibodies for Anti-TNF Therapy," Abstract, Endotoxemia & Sepsis Conference (1991). 4 pages.

Boshart, et al., "A Very Strong Enhancer Is Located Upstream of an Immediate Early Gene of Human Cytomegalovirus", Cell, vol. 41 (1985), pp. 521-530.

Bringman, Timothy S. and Aggarwal, Bharat B., "Monoclonal Antibodies to Human Tumor Necrosis Factors Alpha and Beta: Applications for Affinity Purification, Immunoassays, and as Structural Probes," Hybridoma, vol. 6, No. 5 (1987), pp. 489-507.

Butler et al., "TNF Receptor Fusion Proteins Are Effective Inhibitors of TNF-Mediated Cytotoxicity on Human KYM-1D4 Rhabdomyosarcoma Cells", Cytokine, vol. 6, No. 6 (1994), pp. 616-623.

Capellas, et al., "Enzymatic Condensation of Cholecystokinin CCK-8 (4-6) and CCK-8 (7-8) Peptide Fragments in Organic Media," Biotechnology and Bioengineering, vol. 56, No. 4 (1997), pp. 456-463.

Capon et al., "Designing CD4 immunoadhesins for AIDS therapy", Nature, vol. 337 (1989), pp. 525-531.

Carter et al., "Humanization of an anti-p185HER2 antibody for human cancer therapy", Proc. Natl. Acad. Sci. U.S. A., vol. 89 (1992), p. 4285.

Cassell SE, Bieber JD, Rich P, Tutuncu ZN, Lee SJ, Kalunian KC, Wu CW, Kavanaugh A. The modified Nail Psoriasis Severity Index: validation of an instrument to assess psoriatic nail involvement in patients with psoriatic arthritis. J Rheumatol. 2007;34(1):123-129.

Cella D, Yount S, Sorensen M, Chartash E, Sengupta N, Grober J. Validation of the Functional Assessment of Chronic Illness Therapy Fatigue Scale relative to other instrumentation in patients with rheumatoid arthritis. J Rheumatol. 2005;32(5):811-819.

Chandran V, Bhella S, Schentag C, Gladman D. Functional Assessment of Chronic Illness Therapy-Fatigue Scale is valid in patients with psoriatic arthritis. Ann Rheum Dis. 2007;66:936-939.

Chothia, et al., "Canonical Structures for the Hypervariable Regions of Immunoglobulins", Journal of Molecular Biology, vol. 196 (1987), pp. 901-917.

Clinicaltrials.gov/ct2/show/NCT02407236. Accessed from the internet Jul. 13, 2020.

Coates LC, Helliwell PS. Validation of minimal disease activity criteria for psoriatic arthritis using interventional trial data. Arthritis Care Res (Hoboken). 2010; 62(7):965-969.

Cohen et al., "Intravenous golimumab in rheumatoid arthritis", Expert Review of Clinical Immunology, (May 15, 2014), vol. 10, No. 7, doi:10.1586/1744666X.2014.918847, pp. 823-830, XP009516813.

Collins, M.S. et al., "Immunoprophylaxis of Polymicrobic Cellulitis with a Human Monoclonal Antibody Against Lipopolysaccharide Antigen of Pseudomonas aeruginosa," Abstract E-63, Abstracts of Annual Meeting 1989.

Colombel et al., "Adalimumab for Maintenance of Clinical Response and Remission in Patients with Crohn's Disease: The CHARM Trial," Gastroenterology. 132:52-65 (2007).

Conrad et al., "Compartment-specific accumulation of recombinant immunoglobulins in plant cells: an essential tool for antibody production and immunomodulation of physiological functions and pathogen activity", Plant Molecular Biology, vol. 38 (1998), pp. 101-109.

Canadian Examination Report for CA2878319 dated Dec. 11, 2019, 4 pages.

Corcoran et al., "Characterization of ligand binding by the human p55 tumour-necrosis-factor receptor", European Journal of Biochemistry, vol. 223 (1994), pp. 831-840.

Costello P, FitzGerald O. Disease mechanisms in psoriasis and psoriatic arthritis. Curr Rheumatol Rep. 2001 ;3(5):419-427.

Geremia et al., "Innate and adaptive immunity in inflammatory bowel disease," Autoimmunity Reviews, 13:3-10 (2014).

Gillies, Stephen D. et al., "High-level expression of chimeric antibodies using adapted cDNA variable region cassettes," J Immunol Methods, 125:191-202 (1989).

Gladman DD, Inman RD, Cook RJ, et al. International spondylarthrites interobserver reliability exercise-the INSPIRE study: II. Assessment of peripheral joints, enthesitis, and dactylitis. J Rheumatol. 2007;34(8):1740-1745.

Gladman DD, Ziouzina O, Thavaneswaran A, Chandran V. Dactylitis in psoriatic arthritis: prevalence and response to therapy in the biologic era. J Rheumatol. 2013;40(8):1357-1359.

Goedkoop AY, Kraan MC, Teunissen MB, et al. Early effects of tumour necrosis factor alpha blockade on skin and synovial tissue in patients with active psoriasis and psoriatic arthritis. Ann Rheum Dis. 2004;63(7):769-773.

Gorman, S.D. and Clark, M.R., "Humanisation of monoclonal antibodies for therapy," Sem Immunol, 2:457-466 (1990).

(56) References Cited

OTHER PUBLICATIONS

Gossen, and H. Bujard, "Tight control of gene expression in mammalian cells by tetracycline-responsive promotoers", Proc. Natl. Acad. Sci. USA, vol. 89 (1992), pp. 5547-5551.
Gray et al., "Secretion capture and report web: use of affinity derivatized agarose microdroplets for the selection of hybridoma cells", Journal of Immunological Methods, vol. 182 (1995), pp. 155-163.
Green et al, "Antigen-specific human monoclonal antibodies from mice engineered with human Ig heavy and light chain YACs", Nature Genetics, vol. 7 (1994), pp. 13-21.
Green, L. "Antibody Engineered via Genetic Engineering of the Mouse: Xenomouse Strains Are a Vehicle for the Facile Generation of Therapeutic Human Monoclonal Antibodies", Journal of Immunological Methods, 231, pp. 11-23 (1999).
H. Hoogenboom et al., "By-passing immunization. Human antibodies from synthetic repertoires of germline VH gene segments rearranged in vitro", Journal of Molecular Biology, vol. 227, No. 2, XP024020530; p. 386 (Sep. 10, 1992).
Hanauer, et al., "IM-UNITI: Three-year Efficacy, Safety, and Immunogenicity of Ustekinumab Treatment of Crohn's Disease," Journal of Crohn's and Colitis: 23-32 (2020).
Hanes et al. "Ribosome display efficiently selects and evolves high-affinity antibodies in vitro from immune libraries", Proc Natl. Aca. Sci USA, vol. 95 (1998), pp. 14130-14135.
Hanes et al., "In vitro selection and evolution of functional proteins by using ribosome display", Proc. Natl. Acad. Sci. USA, vol. 94 (1997), pp. 4937-4942.
Harlow, et al., Antibodies A Laboratory Manual, Cold Spring Harbor Laboratory, pp. 567-569 (1988).
Harris, "Ankylosing Spondylitis", Chapter 6, Spondyloarthropathies, Kellev's Textbook of Rheumatology, 6th Edition, Sledqe CB, pas. 1039-1053 (2001).
Hayashi, H. et al., "An Enzyme-linked Immunosorbent Assay for Recombinant Human Tumor Necrosis Factor Using Monoclonal Antibody," Recent Adv. Chemother, 820-821 (1985).
Healy PJ, Helliwell PS. Measuring clinical enthesitis in psoriatic arthritis: assessment of existing measures and development of an instrument specific to psoriatic arthritis. Arthritis Rheum. 2008;59(5):686-691.
Herve, P. et al., "Monoclonal Anti TNF a Antibody for the Treatment of Severe Acute GvHD in Humans," Abstract 3.25, Lymphoma Res. 9:591 (1990).
Hibi, et al., "Efficacy and safety of ustekinumab in Japanese patients with moderately to severely active Crohn's disease: a subpopulation analysis of phase 3 induction and maintenance studies," Intestinal Research, 15(4): 475-486 (2017).
Hinshaw, L.B. et al., "Survival of Primates in LD100 Septic Shock Following Therapy with Antibody to Tumor Necrosis Factor (TNFa)," Circulatory Shock, 30:279-292 (1990).
Hirai, Makoto et al., "Production and characterization of monoclonal antibodies to human tumor necrosis factor," Journal of Immunological Methods, vol. 96 (1987), pp. 57-62.
Hood et al., "Molecular Farming of Industrial Proteins from Transgenic Maize", Advances in Experimental Medicine and Biology, vol. 464 (1999), pp. 127-147.
Hu, et al., "Information contributed by meta-analysis in exposure-response modeling: application to phase 2 dose selection of guselkumab in patients with moderate-to-severe Psoriasis", Journal of Pharmacokinetics and Pharmacodynamics, vol. 41, No. 3, pp. 239-250, (2014).
Husted JA, Gladman DD, Cook RJ, Farewell VT. Responsiveness of health status instruments to changes in articular status and perceived health in patients with psoriatic arthritis. J Rheumatol. 1998;25(11):2146-2155.
Itoh et al., "Application of Inverse Substrates to Trypsin-Catalyzed Peptide Synthesis", Bioorganic Chemistry, vol. 24, No. 1 (1996), pp. 59-68.
J. L. Hamlin and C. Ma, "The mammalian dihydrofolate reductase locus", Biochimica et Biophysica Acta, vol. 1097 (1990), pp. 107-143.

Janssen Biotech, Inc., Highlights of Prescribing Information, Sep. 2016. 37 pages.
Janssen Research & Development, LLC, "A Study to Evaluate the Safety and Efficacy of Ustekinumab Induction and Maintenance Therapy in participants with Moderately to Severely Active Ulcerative Colitis (UNIFI)," (Dec. 19, 2019). 1 page.
Jones, et al., "Replacing the complementarity-determining regions in a human antibody with those from a mouse," Nature, vol. 321 (1986), pp. 522-525.
Jostins et al., 2012, "Host-microbe interactions have shaped the genetic architecture of inflammatory bowel disease." Nature, 491: pp. 119-124.
Junginger, et al. "Visualization of Drug Transport Across Human Skin and the Influence of Penetration Enhancers", In Drug Permeation Enhancement, Hsieh, D. S., Eds., pp. 59-90 (Marcel Dekker, Inc. New York 1994.
Kameyama, Koh-zoh, et al., "Convenient plasmid vectors for construction of chimeric mouse/human antibodies," FEBS Lett, 244:301-306 (1989).
Katsube, Y., et al., "Analysis of k light chain contribution to anti-DNA antibody activity of a human VH4-21-encoded monoclonal antibody (NE-1) by antibody-phage display technique", International Journal of Molecular Medicine, vol. 1, No. 5 (1998), pp. 863-868.
Kavanaugh et al., 2014, "Clinical efficacy, radiographic and safety findings through 5 years of subcutaneous golimumab treatment in patients with active psoriatic arthritis: results from a long-term extension of a randomised, placebo-controlled trial (the GO-REVEAL study)", Ann Rheum Dis, 73(9): 1689-1694.
Kawasaki, Hajime et al., "Analysis of Endotoxin Fever in Rabbits by Using a Monoclonal Antibody to Tumor Necrosis Factor (Cachectin)," Infection and Immunity, 57(10):3131-3135 (1989).
Kenny et al., "Production of Monoclonal Antiboodies Using a Secretion Capture Report Web", Bio/Technology, vol. 13 (1995), pp. 787-790.
Khilji FA, Gonzalez M, Finlay AY. Clinical meaning of change in dermatology life quality index scores. Br J Dermatol. 2002;147(suppl 62): 25-54. Simponi IV (golimumab) Clinical Protocol CNTO148PSA3001 Amendment 2 98 Approved, Jun. 29, 2016.
Knappik, et al., "Fully Synthetic Human Combinatorial Antibody Libraries (HuCAL) Based on Modular Consensus Frameworks and CDRs Randomized with Trinucleotides," Journal of Molecular Biology, 296(1): 57-86 (2000).
Knight, D. M. et al., "A Construction and Initial Characterization of a Mouse-Human Chimeric Anti-TNF Antibody", Mol. Immunol. 30 (16): 1443-1453, 1993.
Kolls et al., "Prolonged and effective blockade of tumor necrosis factor activity through adeno virus-mediated gene transfer", Proc. Natl. Acad. Sci. USA, vol. 91 (1994), pp. 215-219.
Kozbor et al., "The production of monoclonal antibodies from human lymphocytes", Immunol. Today, 4:72-79(1983).
Kretzschmar, et al., "Antibody discovery: phage display," Current Opinion in Biotechnology, 13: 598-602 (2002).
Krnjevic-Pezic, et al., "Our experience using ustekinumab in patients with plaque psoriasis," British Journal of Dermatology, Abstract P-24 (2011). Abstract only.
Kumaran et al., "Conformationally driven protease-catalyzed splicing of peptide segments: V8 protease-mediated synthesis of fragments derived from thermolysin and ribonuclease A", Protein Science, vol. 6, No. 10 (1997), pp. 2233-2241.
Larmonier et al., "The inhibition of TNF-alpha anti-tumoral properties by blocking antibodies promotes tumor growth in rat model" Exp. Cell Res. Mar. 30, 2007; Epub ahead of print; Abstract only, 1 page.
Lassalle, Ph., et al., "Potential Implicaton of Endothelial Cells in Bronchial Asthma," Int Arch Allergy Appl Immunol, 94:233-238 (1991).
Lee, et al., "Increased Expression of Interleukin 23 p19 and p40 in Lesional Skin of Patients with Psoriasis Vulgaris," Journal of Experimental Medicine, 199(1): 125-130 (2004).

(56) References Cited

OTHER PUBLICATIONS

Lesslauer et al., "Recombinant soluble tumor necrosis factor receptor proteins protect mice from lipopolysaccharide-induced lethality", European Journal of Immunology, vol. 21 (1991), pp. 2883-2886.

Li, et al., "Relationship Between Combined Histologic and Endoscopic Endpoints and Efficacy of Ustekinumab Treatment in Patients with Ulcerative Colitis," Gastroenterology, S0016-5085 (20): 35107-6 (Journal Pre-proof Aug. 2020).

Cramer et al., "Transgenic Plants for Therapeutic Proteins: Linking Upstream and Downstream Strategies", Current Topics in Microbiology and Immunology, vol. 240 (1999), pp. 95-118.

Cross, A.S. et al., "Pretreatment with Recombinant Murine Tumor Necrosis Factor a Cachectin and Murine Interleukin 1 a Protects Mice from Lethal Bacterial Infection," J of Exp Med., 169:2021-2027 (1989).

Cua, et al., "Interleukin-23 rather than interleukin-12 is the critical cytokine for autoimmune inflammation of the brain," Nature, 421: 744-748 (2003).

Cullen, et al., "Functional Analysis of the Transcription Control Region Located Within the Avian Retroviral Long Terminal Repeat", Molecular and Cellular Biology, vol. 5 (1985), pp. 438-447.

Cunningham and Wells, "High-Resolution Epitope Mapping of hGH-Receptor Interations by Alanine-Scanning Mutagenesis", Science Ausubel, supra, Chapters 8, 15; 244:1081-1085 (1989)).

D. Shealy et al., "Characterization of golimumab, a human monoclonal antibody specific for human tumor necrosis factor alpha", MABS, vol. 2, No. 4, pp. 428-439 (2010).

Danese, et al., "Ulcerative Colitis," New England Journal of Medicine, 365:1715-1725 (2011).

David M. Frucht, "IL-23: A Cytokine That Acts on Memory T Cells," Science STKE, 114: 1-3 (2002).

Davidson, et al., "IL-12, But Not IFN-y, Plays a Major Role in Sustaining the Chronic Phase of Colitis inIL-10-DeficientMice," The Journal of Immunology, 161: 3143-3149 (1998).

De Vos, et al., "Human Growth Hormone and Extracellular Domain of Its Receptor: Crystal Structure of the Complex", Science, vol. 255 (1992), pp. 306-312.

Deodhar, A. A. et al., "Safety and Efficacy of Intravenous Golimumab in Adult Patients with Active Ankylosing Spondylitis: Results through Week 28", Arthritis Rheumatol, 68, Suppl. 10, abstract No. 1043, Sep. 28, 2016, 3 pages.

Di Giovine, Francesco, S. et al., "Tumour necrosis factor in synovial exudates," Annals of the Rheumatic Diseases, 47:768-772 (1988).

Doyle et al., Rheumatology 52:1214-1219,(2013).

Duncombe, Andrew S. et al., "Tumor Necrosis Factor Mediates Autocrine Growth Inhibition in a Chronic Leukemia," J Immunol, 143:3828-3834 (1989).

Dupont et al., "*Escherichia coli* Diarrhea" Bacterial Infections of Humans: Epidemioloqv and Control, A.S. Evans et al., 2nd Edition, Spring Science & Business Media, New York, pp. 239-254(1991).

E. Rankin et al., "The therapeutic effects of an engineered human anti-tumour necrosis factor alpha antibody (CDP571) in rheumatoid arthritis", British Journal of Rheumatology, vol. 34, No. 4, pp. 334-342, XP000674590 (Apr. 1995).

Echtenacher, Bernd et al., "Requirement of Endogenous Tumor Necrosis Factor/Cachectin for Recovery from Experimental Peritonitis," J. of Immunology, 145(11):3762-3766 (1990).

Eck, Michael J. and Sprang, Stephen R., "The Structure of Tumor Necrosis Factor-L at 2.6 L Resolution," J Biol Chem, 264:17595-17605 (1989).

Eduardo Padlan, "Anatomy of the Antibody Molecule," Molecular Immunology, 31(3): 169-217 (1994).

Edward V. Loftus, Jr., "Clinical Epidemiology of Inflammatory Bowel Disease: Incidence, Prevalence, and Environmental Influences," Gastroenterology, 126(6):1504-1517 (2004).

Elliott, M.J. et al., "A Repeated Therapy with Monoclonal Antibody to Tumour Necrosis Factor a (cA2) in Patients with Rheumatoid Arthritis", The Lancet, vol. 344 (1994), pp. 1125-1127.

Engelmann, Hartmut et al., "A Tumor Necrosis Factor-binding Protein Purified to Homogeneity from Human Urine Protects Cells from Tumor Necrosis Factor Toxicity," J. of Bio. Chem., 264(20): 1974-11980 (1989).

Engelmann, Hartmut et al., "Two Tumor Necrosis Factor-binding Proteins Purified from Human Urine," Journal of Biological Chemistry, vol. 265, No. 3 (1990), pp. 1531-1536.

Eren et al. "Human monoclonal antibodies specific to hepatitis B virus generated in a human/mouse radiation chimera: the Trimera system", Immunology, vol. 93 (1998), pp. 154-161.

EUROQOL Group. EUROQOL—a new facility for the measurement of health-related quality of life. Health Policy. 1990;16:199-208.

Exley, A.R. et al., "Monoclonal Antibody (Mab) to Recombinant Human Tumour Necrosis Factor (rhTNF) in the Prophylaxis and Treatment of Endotoxic Shock in Cynomolgus Monkeys," Medical Research Society, Abstract 184, p. 50 (1989).

Exley, A.R. et al., "Monoclonal antibody to TNF in severe septic shock," The Lancet, 335:1275-1277(1990).

Faraawi et al., 2016, "Comparison of Baseline Characteristics of Rheumatoid Arthritis Patients Initating Therapy with Subcutaneous Golimumab and Infliximab and Intravenous Golimumab: An Analysis from the Prospective, Observational Registry, BioTRAC." The Journal of Rheumatology, 43(6), No. 87, p. 1186.

Feagan et al., "Vedolizumab as Induction and Maintenance Therapy for Ulcerative Colitis," New England Journal of Medicine, 369:699 710 (2013).

Feagan, et al., "Ustekinumab as Induction and Maintenance Therapy for Crohn's Disease," The New England Journal of Medicine, 375: 1946-1960 (2016).

Feldman SR, Gordon KB, Bala M, et al. Infliximab treatment results in significant improvement in the quality of life of patients with severe psoriasis: a double-blind placebo-controlled trial. British Journal of Dermatology. 2005;152:954-960.

Felson, et al., "American College of Rheumatology Preliminary Definition of Improvement in Rheumatoid Arthritis," Arthritis & Rheumatism, 38 (6): 727-735 (1995).

Fendly, Brian M. et al., "Murine Monoclonal Antibodies Defining Neutralizing Epitopes on Tumor Necrosis Factor," Hybridoma, vol. 6, No. 4 (1987), pp. 359-370.

Finlay AY, Khan GK. Dermatology Life Quality Index (DLQI)—a simple practical measure for routine clinical use. Clin Exp Dermatol. 1994;19(3):210-216.

Fisch et al., "Site-Specific Modification of a Fragment of a Chimeric Monoclonal Antibody Using Reverse Proteolysis", Bioconjugate Chemistry, vol. 3 (1992), pp. 147-153.

Fischer et al., "Towards molecular farming in the future: moving from diagnostic protein and antibody production in microbes to plants", Biotechnology and Applied Biochemistry, vol. 30 (1999), pp. 101-108.

Fishwild et al., "High-avidity human IgGk monoclonal antibodies from a novel strain of minilocus transgenic mice", Nature Biotechnology, vol. 14, No. 7 (1996), pp. 845-851.

Fong, Yuman and Lowry, Stephen F., "Tumor Necrosis Factor in the Pathophysiology of Infection and Sepsis," Clin Immunol Immunopathol, 55:157-170 (1990).

Fong, Yuman et al., "Antibodies to Cachectin/Tumor Necrosis Factor Reduce Interleukin 1β and Interleukin 6 Appearance During Lethal Bacteremia," J. Exp. Med., 170:1627-1633 (1989).

Foote et al., "Antibody Framework Residues Affecting the Conformation of the Hypervariable Loops", Journal of Molecular Biology, 224(2), pp. 487-499 (1992).

Fredriksson T, Pettersson U. Severe psoriasis—oral therapy with a new retinoid. Dermatologica. 1978; 157(4):238-244.

Fries JF, Spitz P, Kraines RG, Holman HR. Measurement of patient outcomes in arthritis. Arthritis Rheum. 1980;23(2):137-145.

Galloway, Cynthia J et al., "Monoclonal anti-tumor necrosis factor (TNF) antibodies protect mouse and human cells from TNF cytotoxicity," J. of Immunological Methods, 140:37-43 (1991).

Garrett S, Jenkinson T, Kennedy LG, Whitelock H, Gaisford P, Calin A. A new approach to defining disease status in ankylosing spondylitis: the Bath Ankylosing Spondylitis Disease Activity Index. J Rheumatol. 1994;21(12):2286-2291.

(56) References Cited

OTHER PUBLICATIONS

GenBank Accession No. AA418747, Hillier, et al., May 12, 1997. 3 pages.
GenBank Accession No. AA418955, Hillier, et al., May 12, 1997. 3 pages.
GenBank Accession No. AF301620, Oppmann, et al., Dec. 4, 2000. 2 pages.
GenBank Accession No. C06368, J. Takeda, Aug. 9, 1996. 2 pages.
Genebank Accession, No. M32046 (1990,Jun. 15). 1 page.
Genebank Accession, No. N90300 (Nov. 1, 1989). 1 page.
Altschul, et al., "Basic Local Alignment Search Tool," Journal of Molecular Biology, 215: 403-410 (1990).
Anonymous: "NCT03466411 A Study of the Efficacy and Safety of Guselkumab in Participants With Moderately to Severely Active Crohn's Disease (GALAXI)", None (earliest Version on record) 2 Mar. 30, 2018 Contacts/Locations Study Status, Contacts/Locations and Study Design 16 May 16, 2019 Contacts/Locations and Study Status 17 Jun. 13, 2019 Study Status and Contacts/Locations 18 Jul. 11, 2019 Study St, Feb. 21, 2019 (Feb. 21, 2019), pp. 1-28, XP055895303.
Bhandari et al, "Discovery of Novel Oral Peptide Antagonists of IL-23 Receptor that are Efficacious in a Rat Model of IBD." Inflammatory Bowel Diseases, Mar. 2016, vol. 22, No. 1, abstract p. 148.
Boehringer Ingelheim & Abbvie press release, "IL-23 inhibitor risankizumab induces remission in phase II study in patients with moderate-to-severe Crohn's disease"; news.abbvie.com/news/il-23-linhibitor-risankizumab-induces-remission-in-phase-ii-study-in-patients-with-moderate-to-severe-crohns-disease.htm; May 2016.
Boehringer Ingelheim, May 2016. "IL-23 Inhibitor Risankizumab Induces Remission in Phase II Study in Patients with Moderate-to-Severe Crohn's Disease" 4 pages.
Devereaux, et al., "A comprehensive set of sequence analysis programs for the VAX," Nucleic Acids Research, 12(1):387-395 (1984).
Fan, et al., "Mixed treatment comparison of infliximab with ustekinumab in patients with moderate to severe psoriasis," British Journal of Dermatology, Abstract p. 64 (2011). Abstract only.
Feagan et al, Induction therapy with the selective interleukin-23 inhibitor risankizumab in patients with moderate-to-severe Crohn's disease: a randomized, double-blind, placebo-controlled phase 2 study, Lancet; Apr. 29, 2017; vol. 389, pp. 1699-1709.
Feagan et al, "Supplemental Material: Induction therapy with the selective interleukin-23 inhibitor risankizumab in patients with moderate-to-severe Crohn's disease: a randomised, double-blind, placebo-controlled phase 2 study" Lancet; Apr. 2017; vol. 389, pp. 1699-1709.
Girolomoni G. et al: "The role of IL-23 and the IL-23/T H 17 immune axis in the pathogenesis and treatment of psoriasis", JEADV. Journal of the European Academy of Dermatology and Venereology., vol. 31, No. 10, Oct. 1, 2017 (Oct. 1, 2017 ), pp. 1616-1626.
Henikoff, et al., "Amino acid Substitution matrices from protein blocks," Proceedings of the National Academy of Sciences USA, 89: 10915-10919 (1992).
Hong, et al., IL-12, independently of IFN-gamma, plays a crucial role in the pathogenesis of a murine psoriasis-like skindisorder, Journal of Immunology, 162(12): 7480-7491 (1999).
Langrish, et al., "IL-23 drives a pathogenic T cell population that induces autoimmune inflammation," Journal of Experimental Medicine, 201(20: 233-240 (2005).
Leonard, et al., "Prevention of experimental autoimmune encephalomyelitis by antibodies against interleukin 12," Journal of Experimental Medicine, 181(1): 381-386 (1995).
Liu et al, "Blockage of tumor necrosis factor prevents intestinal mucosal inflammation through down-regulation of interleukin-23 secretion", Journal of Autoimmunity, London, GB, vol. 29, No. 2-3, Sep. 14, 2007 (Sep. 14, 2007), p. 187-194, XP022245363.

Malfait, et al., "Blockade of IL-12 during the induction of collagen-induced arthritis (CIA) markedly attenuates the severity of the arthritis," Clinical and Experimental Immunology, 111:327-383 (1998).
Needleman, S. & Wunsch, C, "A General Method Applicable to the Search for Similarities in the Amino Acid Sequence of Two Proteins.", J. Mol. Biol., 1970, pp. 443-453, vol. 48.
Perrier Clementine et al, "Cytokine blockade in inflammatory bowel diseases", Immunotherapy, Future Medicine Ltd, GB, vol. 3, No. 11, Nov. 1, 2011 (Nov. 1, 2011), p. 1341-1352, XP009177396.
Presky et al., "A functional interleukin 12 receptor complex is composed of two beta-type cytokine receptor subunits," Proceedings of the National Academy of Science USA, 93(24): 14002-14007 (1996).
Ramos et al; "Targeting Specific Immunologic Pathways in Crohn's Disease." Gatroenterol Clin N Am, Sep. 2017, vol. 46, No. 3, pp. 577-588.
Sandborn et al, ("Guselkumab for the Treatment of Crohn's Disease: Induction Results from the Phase 2 GALAXI-1 Study." Gastroenterology 2022;162:1650-1664).
Sandborn William, et al. "882—Efficacy and Safety of Anti-Interleukin-23 Therapy with Mirikizumab (LY3074828) in Patients with Moderate-To-Severe Ulcerative Colitis in a Phase 2 Study." Gastroenterology, vol. 154, No. 6, May 1, 2018, pp. S-1360.
Shields, et al., "High Resolution Mapping of the Binding Site onHuman IgFI for FOyRI, FCyRII, FCyRIII, and RcRn and Design of IgGI Variants with Improved Binding to the RCyR," The Journal of Biological Chemistry, 276(9): 6591-6604 (2001).
Umana, et al., "Engineered glycoforms of an anfineuro-blastoma IgGI with optimized antibody-dependent cellular cytotoxic activity," Nature Biotechnology, 17: 176-190 (1999).
Visvanathan et al, "OP103 Selective IL-23 Inhibition by Risankizumab Modulates the Molecular Profile in the Colon of Active Crohn's Diseae Patients." United European Gastroenterology Journal; 4 (5S) A1-A156), Oct. 2016.
Ritchlin C, Haas-Smith SA, Hicks D, Cappuccio J, Osterland CK, Looney RJ. Patterns of cytokine production in psoriatic synovium. J Rheumatol. 1998;25(8):1544-1552.
Ruddle, Nancy H. et al., "An Antibody to Lymphotoxin and Tumor Necrosis Factor Prevents Transfer of Experimental Allergic Encephalomyelitis," J. Exp. Med., 172:1193-1200 (1990).
Rudikoff et al., Single amino acid substitution altering antigen-binding specificity, PNAS, Mar. 1982, vol. 79, p. 1979-83.
S. Siegal et al., "The mouse/human chimeric momoclonia antibody cA2 neutralizes TNF in vitro and protects transgenic mice from cachexia and TNF lethality in vivo", Cytokine, vol. 7, No. 1 pp. 15-25 XP000990566 (Jan. 1995).
S. Stephens et al., "Comprehensive pharmacokinestic of a humanized antibody and analysis of residual anti-idoiotypic responses", Immunology, vol. 85, No. 4, pp. 668-674 XP000881488 (Aug. 1995).
Sandborn et al., "A Randomized Trial of Ustekinumab, a Human Interleukin-12/23 Monoclonal Antibody, in Patients with Moderate-to-Severe Crohn's Disease," Gastroenterology. 135(4):1130-1141 (2008).
Sandborn et al., "Adalimumab Induces and Maintains Clinical Remission in Patients With Moderate-to-Severe Ulcerative Colitis," Gastroenterology. 142:257-265 (2012).
Sandborn et al., "Vedolizumab as Induction and Maintenance Therapy for Crohn's Disease," New England Journal of Medicine, 369:711-721 (2013).
Sandborn, et al., "Long-Term Efficacy and Safety of Ustekinumab for Crohn's disease through the second year of therapy," Alimentary Pharmacology & Therapeutics, 48: 65-77 (2018).
Sandhu et al., "The Use of SCID Mice in Biotechnology and as a Model for Human Disease", Critical Reviews in Biotechnology, vol. 16 (1996), pp. 95-118.
Sands, et al., "Ustekinumab as Induction and Maintenance Therapy for Ulcerative Colitis," The New England Journal of Medicine, 381(13): 1201-1214 (2019).
Sands, et al., "Safety and Efficacy of Ustekinumab Induction Therapy in Patients with Moderate to Severe Ulcerative Colitis:

(56) References Cited

OTHER PUBLICATIONS

Results from the Phase 3 UNIFI Study," American College of Gastroenterology Conference, Philadelphia, Pennsylvania (Oct. 2018). (Poster Presentation). 15 pages.

Scallon, et al., "Functional Comparisons of Different Tumour Necrosis Factor Receptor/IgG Fusion Proteins", Cytokine, vol. 7 (1995), pp. 759-770.

Schall, Thomas J. et al., "Molecular Cloning and Expression of a Receptor for Human Tumor Necrosis Factor," Cell, vol. 61 (1990), pp. 361-370.

Schmidt, et al., Expression of Interleukin-12-Related Cytokine Transcripts in Inflammatory Bowel Disease: Elevated Interleukin-23p19 and Interneukin-27p28 in Crohn's Disease But Not in Ulcerative Colitis, 11: 16-23 (2005).

Schoch, et al, "Charge-mediated influence of the antibody variable domain on FcRn-dependent pharmacokinetics," Proceedings of the National Academy of Science, 112(19): 5997-6002 (2015).

Scott et al., "An Anti-Tumor Necrosis Factor-a Antibody Inhibits the Development of Experimental Skin Tumors", Mol. Can Therapy, May 2003, 2:445-451.

Shimamoto, Yoshinori et al., "Monoclonal antibodies against human recombinant tumor necrosis factor: prevention of endotoxic shock," Immunology Letters, 77:311-318 (1988).

Silva, Ayona T. et al., "Prophylactic and Therapeutic Effects of a Monoclonal Antibody to Tumor Necrosis Factor-a in Experimental Gram-Negative Shock," J. of Infectious Diseases, 162:421-427(1990).

Simon, et al., "Ustekinumab for the treatment of Crohn's disease: can it find its niche?" Therapeutic Advances in Gastroenterology, 9 (1): 26-36 (2016).

Sims et al., "A Humanized CD18 Antibody Can Block Function without Cell Destruction", Journal of Immunology, vol. 151 (1993), p. 2296.

Smith, Craig R., "Human and Chimeric Antibodies to LPS and TNF," 4Abstract, Endotoxemia & Sepsis Conference (1991). 4 pages.

Smith, et al., "Human Interleukin 4: The Solution Structure of a Four-helix Bundle Protein", Journal of Molecular Biology, vol. 224 (1992), pp. 899-904.

Sofen, et al., "Guselkumab (an IL-23-specific mAb) demonstrates clinical and molecular response in patients with moderate-to-severe psoriasis," Journal of Allergy and Clinical Immunology, 133(4): 1032-1040 (2014).

Sofen, et al., "Results of a single ascending dose study to assess the safety and tolerability of CNTO1959 following intravenous or subcutaneous administration in healthy subjects and in subjects with moderate to severe psoriasis," British Journal of Dermatology, Abstract FC-21 (2011). Abstract only.

Sprague, et al., "Expression of a Recombinant DNA Gene Coding for the Vesiclar Stomatitis Virus Nucleocapsid Protein", Journal of Virology, vol. 45 (1983), pp. 773-781.

Starnes, H. Fletcher, Jr., et al., "ANTI-IL-6 Monoclonal Antibodies Protect Against Lethal *Escherichia Coll* Infection and Lethal Tumor Necrosis FactorL Challenge in Mice," J Immunol, 145:4185-4191 (1990).

Steadman Medical Dictionary, 27th Ed. 2000 Lippincott Williams & Wilkins—"Carcinoma", 7 pages.

Steenbakkers et al., "Efficient generation of monoclonal antibodies from preselected antigen-specific B", Molecular Biology Reports, vol. 19 (1994), pp. 125-134.

Stein et al., "Diseases of the Hearth and Blood Vessels", Internal Medicine, 3rd 3d., p. 1-13, Little Brown and Co. Boston (1990).

Steven Brant, "Promises, Delivery, and Challenges of Inflammatory Bowel Disease Risk Gene Discovery," Clinical Gastroenterology and Hepatology, 11(1):22-26 (2013).

Stone et al., "Solid malignancies among patients in the Wegener's Granulomatosis Etanercept Trial", Arthritis Rheum. May 2006; 54(5) 1608-18 abstract only.

Sunahara, N. et al., "Simple enzyme immunoassay methods for recombinant human tumor necrosis factor L and its antibodies using a bacterial cell wall carrier," J Immunol Methods, 109:203-214(1988).

Supplementary European Search Report dated May 25, 2022. 6 pages.

Suresh et al., "Bispecific Monoclonal Antibodies from Hybrid Hybridomas", Methods in Enzymology 121:210 (1986).

Tally et al., "An Evidence-Based Systematic Review of Medical Therapies for Inflammatory Bowel Disease," American Journal of Gastroenterology, 106 Suppl 1:S2-S25 (2011).

Tavernier et al., "Analysis of the Structure-Function Relationship of Tumour Necrosis Factor. Human/Mouse Chimeric TNF Proteins: General Properties and Epitope Analysis", Journal Molecular Biology, 211, p. 493-501 (1990).

Taylor et al., "A transgenic mouse that expresses a diversity of human sequence heavy and light chain immunoglobulins", Nucleic Acids Research, vol. 20, No. 23 (1992), pp. 6287-6295.

Taylor W, Gladman D, Helliwell P, Marchesoni A, Mease P, Mielants H; CASPAR Study Group. Classification criteria for psoriatic arthritis: development of new criteria from a large international study. Arthritis Rheum. 2006;54 (8):2665-2673.

Taylor, et al., "Human immunoglobulin transgenes undergo rearrangement, somatic mutation and class switching in mice that lack endogenous IgM," International Immunology, vol. 6, No. 4 (1994), pp. 579-591.

Tracey, Kevin J. et al., "Anti-cachectin/TNF monoclonal antibodies prevent septic shock during lethal bacteraemia," Nature, 330:662-664 (1987).

Traunecker, et al., "Bispecific Single chain molecules (Janusins) target cytotoxic lymphocytes on HIV infected cells," EMBO Journal, 10(12): 3655-3659 (1991).

Trinchieri, et al., "The IL-12 Family of Heterodimeric Cytokines: New Players in the Regulation of T Cell Responses," Immunity, 19: 641-644 (2003).

Tuaillon et al., "Human immunoglobulin heavy-chain minilocus recombination in transgenic mice: Gene-segment use in u and y transcripts", Proc Natl Acad Sci USA, vol. 90, No. 8 (1993), pp. 3720-3724.

Tursi et al; Journal of Gastrointestinal and Liver Diseases, Sep. 2017, vol. 26, No. 3, pp. 239-244.

Uhlig et al., "Differential Activity of IL-12 and IL-23 in Mucosal and Systemic Innate Immune Pathology," Immunity. 25:309 318 (2006).

Vajdos, et al., "Comprehensive Functional Maps of the Antigen-Binding Site of an Anti-ErbB2 Antibody Obtained with Shotgun Scanning Mutagenesis," Journal of Molecular Biology, 320(2): 415-428 (2002).

Van der Heijde DM, van Leeuwen MA, van Riel PL, et al. Biannual radiographic assessments of hands and feet in a three-year prospective followup of patients with early rheumatoid arthritis. Arthritis Rheum. 1992;35(1):26-34.

Van der Linden MA. Disease Activity Scores using C-reactive protein. Apr. 5, 2004. Available at: www.umcn.nl/scientist/afdelingen/reumatologie/the das/the_das_crp. Accessed Aug. 19, 2005, 10 pages.

Van Riel P, Fransen J, Scott DL. EULAR handbook of clinical assessments in rheumatoid arthritis. Third ed. Alphen Aan Den Rijn, The Netherlands: Van Zuiden Communications B.V. 2004. 54 pages.

Matteo Menga, Anna Balato, Annunziata Raimondo and Nicola Balato (2018) Guselkumab for the treatment of psoriasis, Expert Opinion on Biological Therapy, 18:4, 459-468, DOI: 10.1080/14712598.2018.1445223. Published online Mar. 3, 2018. (Year: 2018).

Berman et al., "Guselkumab in the treatment of concomitant hidradentitis supperativa, psoriasis, and Crohn's disease", The Journal of Dermatological Treatment, vol. 32, No. 2, Aug. 23, 2019, pp. 261-263.

Brunner et al., "Infliximab induces downregulation of the I-12/IL-23 axis in 6-sulfo-LacNac (slan)+ dendritic cells and macrophages", Journal of Allergy and Clinical Immunology, vol. 132, No. 5, Nov. 1, 2013, pp. 1184-1193.e8.

(56) References Cited

OTHER PUBLICATIONS

Cunningham et al., "Golimumab in the treatment of ulcerative colitis", Therapeutic Advances in Gastroenterology, vol. 12, Jan. 1, 2019.

History of Changes for Study: NCT03662542,ClinicalTrials.gov archive,[online], Sep. 24, 2018, [Search day Apr. 21, 2024], URL: https://classic.clinicaltrials.gov/ct2/history/NCT03662542?V_2.

Janssen Research & Development, LLC, "A Study of Efficacy and Safety of Combination Therapy With Guselkumab and Golimumab in Participants With Moderately to Severely Active Ulcerative Colitis (VEGA)". NCT03662542, dated Oct. 30, 2019, found online on Jul. 31, 2024 at ClinicalTrials.gov.

Jurij et al., "Anti-interleukin-23 agents for the treatment of ulcerative colitis", Expert Opinion on Biological Therpay, vol. 20, No. 4, Nov. 27, 2019, pp. 399-406.

Kentaro Muarte et al., "A case where administration of ustekinumab maintained the intestinal patency after balloon dialation for small intestimal stenosis caused by Crohn's disease", HHS Public Access Author Manuscript, vol. 25, No. 11, Aug. 2, 2019, pp. e140-e140.

Olbjorn et al., "Combination of biological agents in moderate to severe pediatric inflammatory bowel disease: a case series and review of the literature", Pediatric Drugs, vol. 22, No. 4, May 7, 2020, pp. 409-416.

Taku Kobayashi "Golimumab." IBD Research vol. 12, No. 3, 2018; pp. 147-150; Presented by Medical Online.

| mab treatment | Day -1 | Day 0 | Day 1 | Day 2 | Day 3 | Day 4 | Day 5 | Day 6 | Day 7 |
|---|---|---|---|---|---|---|---|---|---|
| vehicle | 0.9999 | 0.9999 | 0.9994 | 0.6627 | *0.0286* | *0.0094* | *0.0053* | *0.0061* | 0.1302 |
| 0.15mg aIL-23 | 0.9999 | 0.9999 | 0.9995 | 0.9962 | 0.6460 | 0.2901 | 0.8859 | 0.9963 | 0.9997 |
| 0.5µg aIL-23 | 0.9999 | 0.9999 | 0.9994 | 0.8608 | 0.0733 | *0.0315* | *0.0262* | *0.0240* | *0.0488* |
| 1.5µg aIL-23 | 0.9999 | 0.9295 | 0.9804 | 0.2940 | *0.0001* | *0.0001* | *0.0005* | *0.0400* | 0.7572 |
| 5.0µg aIL-23 | 0.9999 | 0.9996 | 0.9995 | 0.2940 | *0.0002* | *0.0001* | *0.0013* | *0.0023* | 0.1064 |
| 15µg aIL-23 | 0.9999 | 0.9968 | 0.6920 | *0.0197* | *0.0001* | *0.0001* | *0.0001* | *0.0001* | *0.0001* |
| 50µg aIL-23 | 0.9999 | 0.8692 | 0.8394 | *0.0294* | *0.0001* | *0.0001* | *0.0001* | *0.0001* | *0.0021* |
| 15µg aTNFα | 0.9999 | 0.9996 | *0.0001* | *0.0001* | *0.0001* | *0.0001* | *0.0001* | *0.0012* | 0.2235 |
| 150µg aTNFα | 0.9999 | 0.9999 | *0.0001* | *0.0001* | *0.0001* | *0.0001* | *0.0001* | *0.0001* | *0.0001* |

FIG. 4D

| mab treatment | Day -1 | Day 0 | Day 1 | Day 2 | Day 3 | Day 4 | Day 5 | Day 6 | Day 7 |
|---|---|---|---|---|---|---|---|---|---|
| PBS | 0.9999 | 0.9999 | 0.5254 | 0.1832 | 0.0129 | 0.0034 | 0.0427 | 0.1373 | 0.9994 |
| 500μg aTNFα | 0.9999 | 0.9997 | 0.0001 | 0.0001 | 0.0001 | 0.0001 | 0.0001 | 0.0001 | 0.0001 |
| 1.5μg aIL-23 | 0.9999 | 0.9938 | 0.1213 | 0.0021 | 0.0001 | 0.0001 | 0.0001 | 0.0001 | 0.0004 |
| 5μg aIL-23 | 0.9999 | 0.8053 | 0.9996 | 0.1182 | 0.0001 | 0.0001 | 0.0001 | 0.0001 | 0.0009 |
| 25μg aIL-23 | 0.9999 | 0.9938 | 0.8811 | 0.0368 | 0.0001 | 0.0001 | 0.0001 | 0.0001 | 0.0001 |
| 500μg aTNFα + 1.5μg aIL-23 | 0.9999 | 0.9999 | 0.0001 | 0.0001 | 0.0001 | 0.0001 | 0.0001 | 0.0001 | 0.0001 |
| 500μg aTNFα + 5μg aIL-23 | 0.9999 | 0.8191 | 0.0001 | 0.0001 | 0.0001 | 0.0001 | 0.0001 | 0.0001 | 0.0001 |
| 500μg aTNFα + 25μg aIL-23 | 0.9999 | 0.9977 | 0.0001 | 0.0001 | 0.0001 | 0.0001 | 0.0001 | 0.0001 | 0.0001 | time (days)

FIG. 6E

SEQUENCE LISTING

```
<160> NUMBER OF SEQ ID NOS: 20

<210> SEQ ID NO 1
<211> LENGTH: 5
<212> TYPE: PRT
<213> ORGANISM: Homo sapiens

<400> SEQUENCE: 1

Asn Tyr Trp Ile Gly
1               5

<210> SEQ ID NO 2
<211> LENGTH: 17
<212> TYPE: PRT
<213> ORGANISM: Homo sapiens

<400> SEQUENCE: 2

Ile Ile Asp Pro Ser Asn Ser Tyr Thr Arg Tyr Ser Pro Ser Phe Gln
1               5                   10                  15

Gly

<210> SEQ ID NO 3
<211> LENGTH: 8
<212> TYPE: PRT
<213> ORGANISM: Homo sapiens

<400> SEQUENCE: 3

Trp Tyr Tyr Lys Pro Phe Asp Val
1               5

<210> SEQ ID NO 4
<211> LENGTH: 14
<212> TYPE: PRT
<213> ORGANISM: Homo sapiens

<400> SEQUENCE: 4

Thr Gly Ser Ser Ser Asn Ile Gly Ser Gly Tyr Asp Val His
1               5                   10

<210> SEQ ID NO 5
<211> LENGTH: 7
<212> TYPE: PRT
<213> ORGANISM: Homo sapiens

<400> SEQUENCE: 5
```

```
Gly Asn Ser Lys Arg Pro Ser
1               5

<210> SEQ ID NO 6
<211> LENGTH: 11
<212> TYPE: PRT
<213> ORGANISM: Homo sapiens

<400> SEQUENCE: 6

Ala Ser Trp Thr Asp Gly Leu Ser Leu Val Val
1               5                   10

<210> SEQ ID NO 7
<211> LENGTH: 117
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 8
<211> LENGTH: 111
<212> TYPE: PRT
<213> ORGANISM: Homo sapiens

<400> SEQUENCE: 8

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 9
<211> LENGTH: 447
```

<212> TYPE: PRT
<213> ORGANISM: Homo sapiens

<400> SEQUENCE: 9

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
                35                  40                  45

Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 217
<212> TYPE: PRT
<213> ORGANISM: Homo sapiens

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 11
<211> LENGTH: 5
<212> TYPE: PRT
<213> ORGANISM: Homo sapiens

<400> SEQUENCE: 11

Ser Tyr Ala Met His
1               5

<210> SEQ ID NO 12
<211> LENGTH: 17
<212> TYPE: PRT
<213> ORGANISM: Homo sapiens

<400> SEQUENCE: 12
```

Phe Met Ser Tyr Asp Gly Ser Asn Lys Lys Tyr Ala Asp Ser Val Lys
1               5                   10                  15

Gly

<210> SEQ ID NO 13
<211> LENGTH: 17
<212> TYPE: PRT
<213> ORGANISM: Homo sapiens

<400> SEQUENCE: 13

Asp Arg Gly Ile Ala Ala Gly Gly Asn Tyr Tyr Tyr Gly Met Asp
1               5                   10                  15

Val

<210> SEQ ID NO 14
<211> LENGTH: 11
<212> TYPE: PRT
<213> ORGANISM: Homo sapiens

<400> SEQUENCE: 14

Arg Ala Ser Gln Ser Val Tyr Ser Tyr Leu Ala
1               5                   10

<210> SEQ ID NO 15
<211> LENGTH: 7
<212> TYPE: PRT
<213> ORGANISM: Homo sapiens

<400> SEQUENCE: 15

Asp Ala Ser Asn Arg Ala Thr
1               5

<210> SEQ ID NO 16
<211> LENGTH: 10
<212> TYPE: PRT
<213> ORGANISM: Homo sapiens

<400> SEQUENCE: 16

Gln Gln Arg Ser Asn Trp Pro Pro Phe Thr
1               5                   10

<210> SEQ ID NO 17
<211> LENGTH: 126
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Gly
            100                 105                 110

```
Met Asp Val Trp Gly Gln Gly Thr Thr Val Thr Val Ser Ser
            115                 120                 125
```

<210> SEQ ID NO 18
<211> LENGTH: 111
<212> TYPE: PRT
<213> ORGANISM: Homo sapiens

<400> SEQUENCE: 18

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val
            100                 105                 110
```

<210> SEQ ID NO 19
<211> LENGTH: 456
<212> TYPE: PRT
<213> ORGANISM: Homo sapiens

<400> SEQUENCE: 19

```
Gln Val Gln Leu Val Glu Ser Gly Gly Gly Val Val Gln Pro Gly Arg
1               5                  10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

-continued

```
Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
450                 455

<210> SEQ ID NO 20
<211> LENGTH: 215
<212> TYPE: PRT
<213> ORGANISM: Homo sapiens

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
```

-continued

```
            115                 120                 125
Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

METHOD OF TREATING INFLAMMATORY BOWEL DISEASE WITH A COMBINATION THERAPY OF ANTIBODIES TO IL-23 AND TNF ALPHA

CROSS-REFERENCE TO RELATED APPLICATIONS

This application claims priority to U.S. Provisional Application Nos. 63/028,219, filed 21 May 2020 and 63/116,383, filed 20 Nov. 2020. The entire contents of each of the aforesaid applications are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI6317USNP1SEQLIST.txt", creation date of 20 May 2021 and having a size of 18 kb. The sequence listing submitted via EFS-Web is part of the specification and is herein incorporated by reference in its entirety.

BACKGROUND

Inflammatory bowel diseases (IBD), including Crohn's disease (CD) and ulcerative colitis (UC), are characterized by idiopathic intestinal inflammation, disruption of the epithelial barrier, and microbial dysbiosis. While the use of biologic agents, such as anti-TNFα antibody therapies, has revolutionized the clinical management of IBD, many patients do not achieve a clinical response with induction therapy and biologic therapies used as monotherapies have short term remission rates <20%. (2)

The role of IL-23 in promoting intestinal inflammation has been demonstrated in several mouse models where attenuated colitis was exhibited in mice treated with neutralizing anti-IL-23p19 antibodies or in mice with a genetic deletion of the p19 subunit of IL-23. (1, 3-5) Genome-wide association studies (GWAS) have identified polymorphisms in the IL-23 receptor gene (IL23R) associated with both risk and protection for IBD. (6) In patients with moderate to severe Crohn's disease, two anti-IL-23 agents, risankizumab (BI 655066) and brazikumab (MEDI2070, AMG-139), have recently reported Phase 2 results demonstrating efficacy. While there may be a role for anti-IL-23 therapies in the treatment of IBD, it is anticipated that a population of patients may not fully respond to IL-23 alone as observed with anti-TNFα therapies.

There is a need for improved treatment of IBD, particularly of patients that do not respond to therapies based on either an anti-TNFα antibody or an anti-IL-23 antibody alone.

SUMMARY OF THE INVENTION

One aspect of the invention is a method of treating an inflammatory disease, for example, an inflammatory bowel disease in a patient (subject). The method comprises administering a first co-therapeutically effective and clinically safe amount of an IL-23 inhibitor and administering a second co-therapeutically effective and clinically safe amount of a TNF-α inhibitor. The method is effective to treat the inflammatory bowel disease, and the first and second co-therapeutically effective and clinically safe amounts are the same or different.

In some embodiments, the inflammatory bowel disease is ulcerative colitis (UC). In some embodiments, the inflammatory bowel disease is Crohn's disease. In some embodiments, the inflammatory bowel disease is indeterminate colitis. In some embodiments, the subject was previously treated with a TNF-α inhibitor alone and the inflammatory bowel disease did not undergo remission after the previous treatment. In some embodiments, the subject was previously treated with IL-23 inhibitor alone and the inflammatory bowel disease did not undergo remission after the previous treatment.

In various embodiments, the IL-23 inhibitor comprises a pharmaceutical composition of an anti-IL-23p19 antibody (also referred to herein as anti-p19 or anti-IL-23) or an antigen-binding fragment thereof. In various embodiments, the TNF-α inhibitor comprises a pharmaceutical composition of an anti-TNF-α antibody or an antigen-binding fragment thereof. In some embodiments, the anti-IL-23p19 antibody comprises a human antibody or a humanized antibody. In some embodiments, the anti-TNF-α antibody comprises a human antibody or a humanized antibody.

In some embodiments, the IL-23 inhibitor comprises the guselkumab antibody (also referred to as CNTO1959) (marketed by Janssen Biotech, Inc. as Tremfya®) or an antigen-binding fragment thereof comprising the guselkumab CDR sequences of: (i) the heavy chain CDR amino acid sequences of SEQ ID NO: 1 (CDRH1), SEQ ID NO: 2 (CDRH2), and SEQ ID NO: 3 (CDRH3); and (ii) the light chain CDR amino acid sequences of SEQ ID NO: 4 (CDRL1), SEQ ID NO: 5 (CDRL2), and SEQ ID NO: 6 (CDRL3) at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

Another aspect of the method of the invention comprises administering a pharmaceutical composition comprising an isolated anti-IL-23 specific antibody having the guselkumab heavy chain variable region amino acid sequence of SEQ ID NO: 7 and the guselkumab light chain variable region amino acid sequence of SEQ ID NO: 8 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

A further aspect of the method of the invention comprises administering a pharmaceutical composition comprising an isolated anti-IL-23 specific antibody having the guselkumab heavy chain amino acid sequence of SEQ ID NO: 9 and the guselkumab light chain amino acid sequence of SEQ ID NO: 10 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

The guselkumab sequences are as follows:

| SEQ ID NO: | Description | Sequence |
|---|---|---|
| 1 | HCDR1 | NYWIG |
| 2 | HCDR2 | IIDPSNSYTR YSPSFQG |
| 3 | HCDR3 | WYYKPFDV |
| 4 | LCDR1 | TGSSSNIGSG YDVH |
| 5 | LCDR2 | GNSKRPS |
| 6 | LCDR3 | ASWTDGLSLV V |
| 7 | VH | EVQLVQSGAE VKKPGESLKI SCKGSGYSFS NYWIGWVRQM PGKGLEWMGI IDPSNSYTRY SPSFQGQVTI SADKSISTAY LQWSSLKASD TAMYYCARWY YKPFDVWGQG TLVTVSS |
| 8 | VL | QSVLTQPPSV SGAPGQRVTI SCTGSSSNIG SGYDVHWYQQ LPGTAPKLLI YGNSKRPSGV PDRFSGSKSG TSASLAITGL QSEDEADYYC ASWTDGLSLV VFGGGTKLTV L |
| 9 | Heavy Chain | EVQLVQSGAE VKKPGESLKI SCKGSGYSFS NYWIGWVRQM PGKGLEWMGI IDPSNSYTRY SPSFQGQVTI SADKSISTAY LQWSSLKASD TAMYYCARWY YKPFDVWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 10 | Light Chain | QSVLTQPPSV SGAPGQRVTI SCTGSSSNIG SGYDVHWYX LPGTAPKLLI YGNSKRPSGV PDRFSGSKSG TSASLAITGL QSEDEADYYC ASWTDGLSLV VFGGGTKLTV LGQPKAAPSV TLFPPSSEEL QANKATLVCL ISDFYPGAVT VAWKADSSPV KAGVETTTPS KQSNNKYAAS SYLSLTPEQW KSHRSYSCQV THEGSTVEKT VAPTECS |

In various embodiments, the TNF-α inhibitor comprises the golimumab antibody (marketed by Janssen Biotech, Inc. as Simponi®) or an antigen-binding fragment thereof comprising the sequences shown in SEQ ID NOS:

Example Anti-TNF-α Antibody Sequences—SIMPONI® (Golimumab)

CDRs Determined by Kabat

Amino acid sequence of anti-TNF-α antibody complementarity determining region heavy chain 1 (CDRH1): (SEQ ID NO:11)

SYAMH

Amino acid sequence of anti-TNF-α antibody complementarity determining region heavy chain 2 (CDRH2): (SEQ ID NO:12)

FMSYDGSNKKYADSVKG

Amino acid sequence of anti-TNF-α antibody complementarity determining region heavy chain 3 (CDRH3): (SEQ ID NO:13)

DRGIAAGGNYYYYGMDV

Amino acid sequence of anti-TNF-α antibody complementarity determining region light chain 1 (CDRL1): (SEQ ID NO:14)

RASQSVYSYLA

Amino acid sequence of anti-TNF-α antibody complementarity determining region light chain 2 (CDRL2): (SEQ ID NO:15)

DASNRAT

Amino acid sequence of anti-TNF-α antibody complementarity determining region light chain 3 (CDRL3): (SEQ ID NO:16)

QQRSNWPPFT

Amino acid sequence of anti-TNF-α antibody heavy chain variable region (CDRs underlined): (SEQ ID NO:17)

```
  1  QVQLVESGGG VVQPGRSLRL SCAASGFIFS SYAMHWVRQA PGNGLEWVAF MSYDGSNKKY
 61  ADSVKGRFTI SRDNSKNTLY LQMNSLRAED TAVYYCARDR GIAAGGNYYY YGMDVWGQGT
121  TVTVSS
```

Amino acid sequence of anti-TNF-α antibody light chain variable region (CDRs underlined): (SEQ ID NO:18)

```
  1  EIVLTQSPAT LSLSPGERAT LSCRASQSVY SYLAWYQQKP GQAPRLLIYD ASNRATGIPA
 61  RFSGSGSGTD FTLTISSLEP EDFAVYYCQQ RSNWPPFTFG PGTKVDIKRT V
```

Amino acid sequence of anti-TNF-α antibody heavy chain (CDRs underlined): (SEQ ID NO:19)

```
  1  QVQLVESGGG VVQPGRSLRL SCAASGFIFS SYAMHWVRQA PGNGLEWVAF MSYDGSNKKY
 61  ADSVKGRFTI SRDNSKNTLY LQMNSLRAED TAVYYCARDR GIAAGGNYYY YGMDVWGQGT
121  TVTVSSASTK GPSVFPLAPS SKSTSGGTAA LGCLVKDYFP EPVTVSWNSG ALTSGVHTFP
181  AVLQSSGLYS LSSVVTVPSS SLGTQTYICN VNHKPSNTKV DKKVEPKSCD KTHTCPPCPA
241  PELLGGPSVF LFPPKPKDTL MISRTPEVTC VVVDVSHEDP EVKFNWYVDG VEVHNAKTKP
301  REEQYNSTYR VVSVLTVLHQ DWLNGKEYKC KVSNKALPAP IEKTISKAKG QPREPQVYTL
361  PPSRDELTKN QVSLTCLVKG FYPSDIAVEW ESNGQPENNY KTTPPVLDSD GSFFLYSKLT
421  VDKSRWQQGN VFSCSVMHEA LHNHYTQKSL SLSPGK                        456
```

Amino acid sequence of anti-TNF-α antibody light chain (CDRs underlined): (SEQ ID NO:20)

```
  1  EIVLTQSPAT LSLSPGERAT LSCRASQSVY SYLAWYQQKP GQAPRLLIYD ASNRATGIPA
 61  RFSGSGSGTD FTLTISSLEP EDFAVYYCQQ RSNWPPFTFG PGTKVDIKRT VAAPSVFIFP
121  PSDEQLKSGT ASVVCLLNNF YPREAKVQWK VDNALQSGNS QESVTEQDSK DSTYSLSSTL
181  TLSKADYEKH KVYACEVTHQ GLSSPVTKSF NRGEC
```

In some embodiments, the TNF-α inhibitor comprises the golimumab antibody or an antigen-binding fragment thereof comprising the golimumab CDR sequences shown above, variable regions sequences shown above or heavy and light chain sequences shown above at 100 mg/mL in an aqueous solution in a pharmaceutical composition at 100 mg/mL; 4.1% (w/v) sorbitol, 5.6 mM L-Histidine and L-Histidine monohydrochloride monohydrate; 0.015% (w/v) Polysorbate 80 of the composition.

In alternative embodiments, the IL-23 inhibitor is an anti-IL-23p19 antibody, including, without limitation, risankizumab or risankizumab-rzaa (Skyrizi® of Abbvie Inc.), tildrakizumab or tildrakizumab-asmn (Ilumya® of Sun Pharma) and mirakizumab (Eli Lilly and Co.), and the TNF-α inhibitor is the anti-TNF-α antibody adalimumab (Humira® of Abbvie Inc.), the anti-TNF-α antibody infliximab (Remicade® of Janssen Biotech, Inc.), certolizumab pegol (Cimzia® of UCB Inc.) and etanercept (Enbrel® of Amgen and Immunex Corporation). Included as potential TNF-α inhibitors that are part of the present invention are products comprising antibodies that are biosimilar products of the aforementioned TNF-α inhibitors, for example, products approved under provisions of 42 U.S.C. § 262(f) or comparable laws and regulations worldwide. Examples of biosimilar TNF-α inhibitors are the infliximab biosimilars marketed as Inflectra® and Renflexis® and the etanercept biosimilar SB4 (Benepali®).

In some embodiments, the anti-TNFα antibody and the anti-IL-23p19 antibody are administered in a ratio of from 1:2 to 2:1 (w/w). In some embodiments, the anti-TNFα antibody and the anti-IL-23p19 antibody are administered in a ratio of from 15:1 to 400:1 (w/w), or a range of from 2:1 to 14:1.

In some embodiments, the anti-IL-23p19 antibody and the anti-TNFα antibody are administered simultaneously or on the same day for the initial dose and administration is staggered between the two antibodies by two or more weeks for subsequence doses. In some embodiments, the anti-IL-23p19 antibody and the anti-TNFα antibody are administered sequentially. In some embodiments, the anti-IL-23p19 antibody and the anti-TNFα antibody are administered within one day of one another.

In another aspect is provided a method of reducing inflammation of the colon in a subject who has inflammatory bowel disease. The method comprises administering a first co-inflammation reducing effective amount of an anti-IL- 23p19 antibody and administering a second co-inflammation reducing effective amount of an anti-TNFα antibody. The method is effective to reduce inflammation of the colon of the subject to a level comparable to the colon of a normal patient. The first and second co-inflammation reducing effective amounts are the same or different.

In some embodiments, the inflammation is very minimal or normal in a tissue sample from the colon of the subject after administration of the anti-IL-23p19 antibody and the anti-TNFα antibody. In some embodiments, the gland loss is very minimal or normal in a tissue sample from the colon of the subject after administration of the anti-IL-23p19 antibody and the anti-TNFα antibody. In some embodiments, the erosion is very minimal or normal in a tissue sample from the colon of the subject after administration of the anti-IL-23p19 antibody and the anti-TNFα antibody. In some embodiments, the mucosal thickness and hyperplasia are independently very minimal or normal in a tissue sample from the colon of the subject after administration of the anti-IL-23p19 antibody and the anti-TNFα antibody. In some embodiments, after administration of the anti-IL-23p19 antibody and the anti-TNFα antibody, the histopathology of the colon is about identical (or identical) to that of normal tissue.

In another aspect is provided a method of both treating inflammatory bowel disease in a subject and reducing weight loss in the subject. The method comprises: (a) administering a first co-therapeutically and weight loss reducing effective amount of an anti-IL-23p19 antibody or an antigen-binding fragment thereof; and (b) administering a second co-therapeutically and weight loss reducing effective amount of an anti-TNF-α antibody or an antigen-binding fragment thereof; wherein said first and second co-therapeutically and weight loss reducing effective amount are the same or different.

In another aspect is provided a method of treating inflammatory bowel disease in a human subject. The method comprises: (a) administering 0.0005 to 0.002 mg/kg of an anti-IL-23p19 antibody or an antigen-binding fragment thereof; and (b) administering 0.020 to 0.125 mg/kg of an anti-TNF-α antibody or an antigen-binding fragment thereof.

In various embodiments, the method is effective to treat the inflammatory bowel disease. In some embodiments, the inflammatory bowel disease is ulcerative colitis. In some embodiments, the inflammatory bowel disease is Crohn's disease. In some embodiments, the inflammatory bowel disease is indeterminate colitis. In some embodiments, the method is effective to inhibit weight loss (e.g., weight loss associated with the inflammatory bowel disease).

In another aspect is provided a method of preventing inflammation of the colon in a subject who has inflammatory bowel disease, the method comprising: (a) administering a first co-inflammation reducing effective amount of an IL-23 inhibitor; and (b) administering a second co-inflammation reducing effective amount of a TNF-α inhibitor. The method is effective to reduce inflammation of the colon of the subject to a level comparable to the colon of a normal patient. The first and second co-inflammation reducing effective amounts are the same or different.

In one embodiment, guselkumab is administered to UC patients in an initial intravenous dose of 200 mg, intravenous doses of 200 mg at weeks 4 and 8 and subsequent subcutaneous doses of 100 mg every 8 weeks; golimumab is administered in an initial subcutaneous dose of 200 mg and subsequent subcutaneous doses of 100 mg at weeks 2, 6 and 10. The UC patient will be evaluated by Mayo Score to determine clinical response or remission. Clinical response measured at Week 12 is defined as a decrease from baseline in the Mayo score≥30% and ≥3 points with either a decrease in rectal bleeding subscore (RBS)≥1 or a RBS of 0 or 1. Clinical remission measured at Week 12 is defined as a Mayo score≤2 with no individual subscore>1. Additional measures of clinical response are used within the scope of the invention.

In a further embodiment, a patient with inflammatory bowel disease (e.g., UC) treated with the combination of anti-IL-23p19 antibody and anti-TNF-α antibody responds to the combination therapy by meeting one or more clinical endpoints as described herein (e.g., decrease from baseline in Mayo score), but was predicted to be a non-responder to either or both monotherapy of an anti-IL-23p19 antibody or an anti-TNF-α antibody, for example, by baseline biomarker measurements.

In yet a further embodiment, the present invention comprises a pharmaceutical product comprising the combination of an anti-IL-23 inhibitor (e.g., anti-IL-23p19 antibody) and an anti-TNF-α inhibitor (e.g., anti-TNF-α antibody) administered according to the methods described herein.

BRIEF DESCRIPTION OF THE DRAWINGS

FIG. 3A shows the overlap between genes present in the anti-TNFα and anti-IL-23p19 subnetworks as illustrated by a Venn diagram.

FIGS. 4A, 4B, 4C and 4D show the results of a body weight loss analysis performed on female RAG2$^{-/-}$ mice dosed ip with isotype control antibody (FIG. 4A), or anti-IL-23p19 antibody (FIG. 4B) at 50, 15, 5, 1.5, 0.5, 0.15 μg/mouse, or an anti-TNFα antibody (FIG. 4C) at 150 and 15 μg/mouse. Disease was induced by administration of anti-CD40 antibody. As shown in FIG. 4D, statistics were generated comparing each group to the isotype control.

Figure 5A:
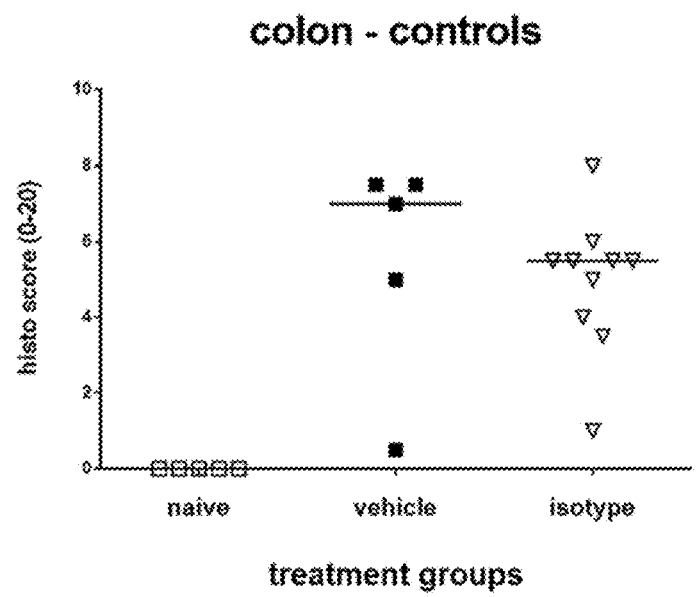
FIGS. 5A, 5B and 5C show the results of a histopathology study performed on the colon of female RAG2$^{-/-}$ mice dosed ip with isotype control antibody (FIG. 5A), anti-IL-23p19 antibody at 50, 15, 5, 1.5, 0.5, 0.15 μg/mouse (FIG.
Figure 5B:
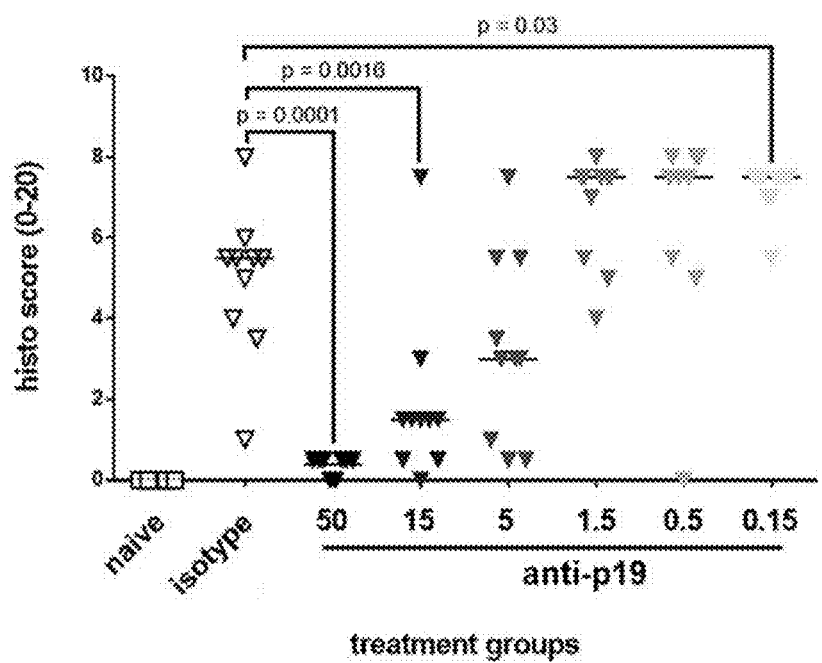
Figure 5C:
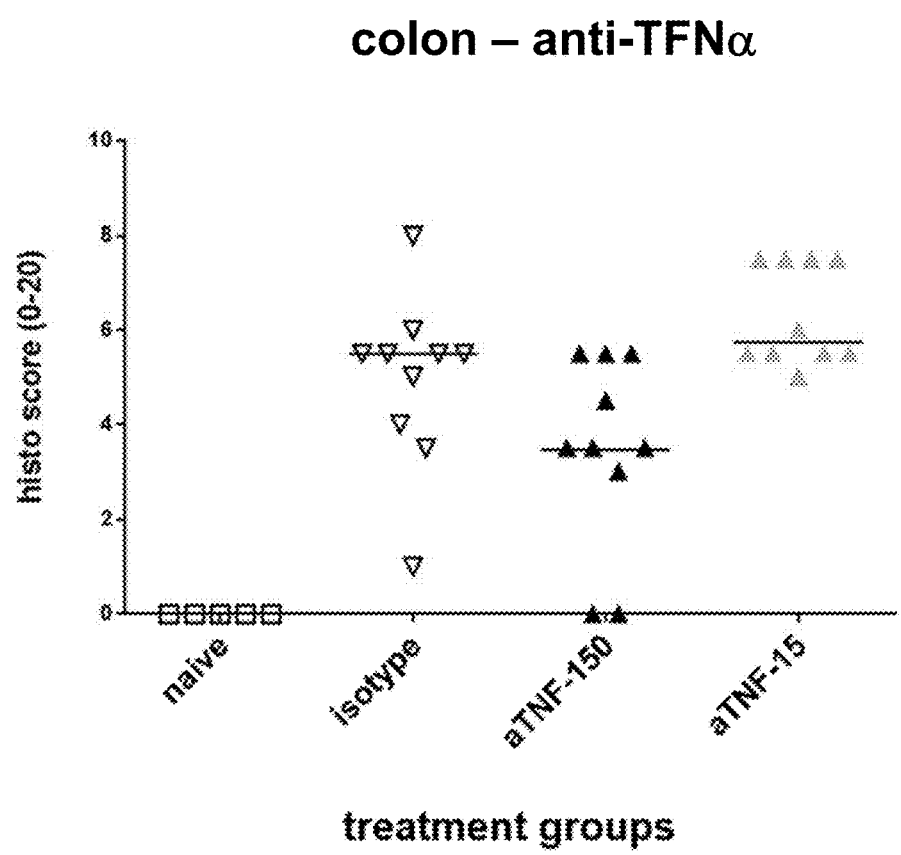

5B), or an anti-TNFα antibody at 150 and 15 µg/mouse (FIG. 5C). Disease was induced by administration of anti-CD40 antibody.

Figure 6A:
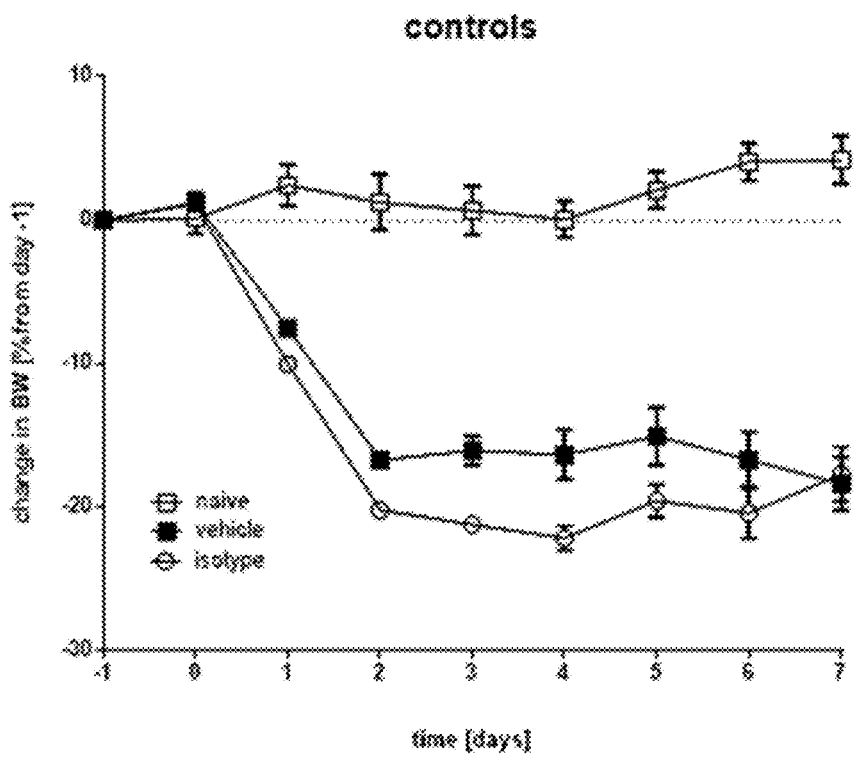
Figure 6B:
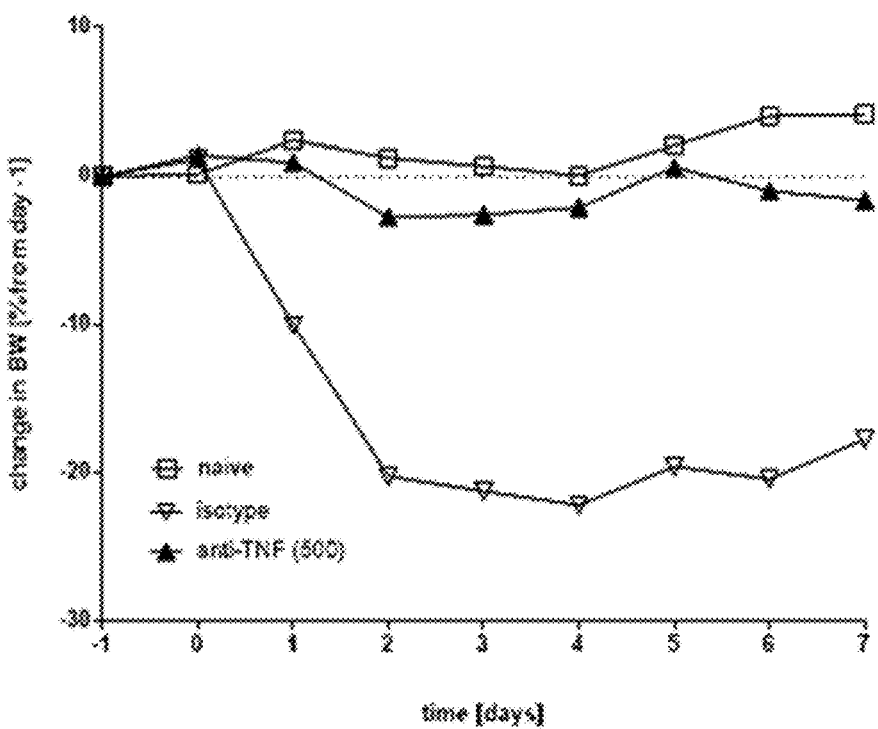
Figure 6C:
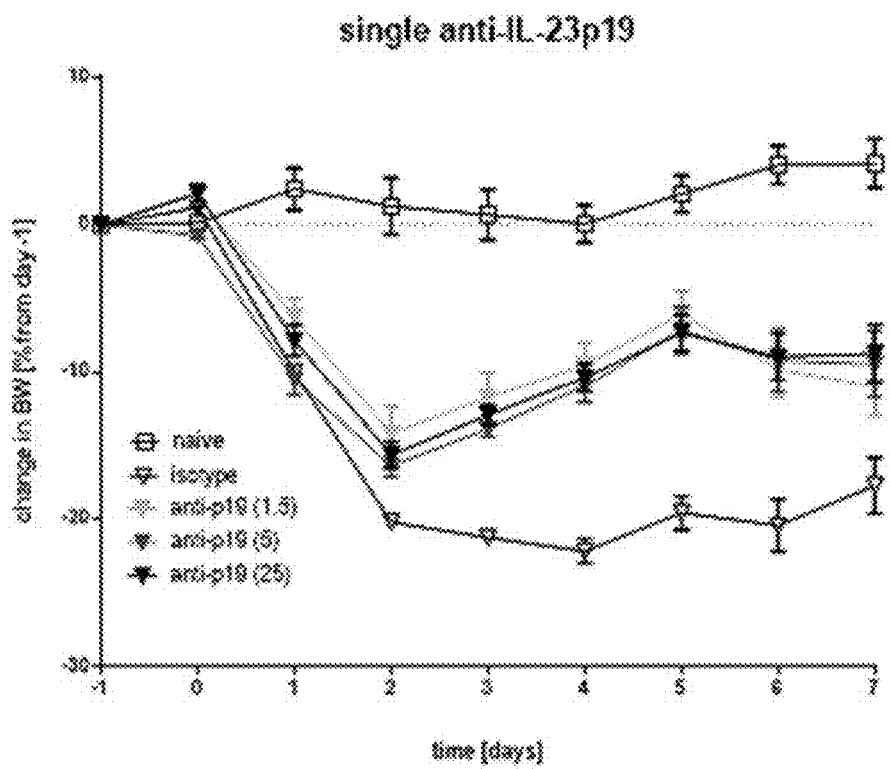
Figure 6D:
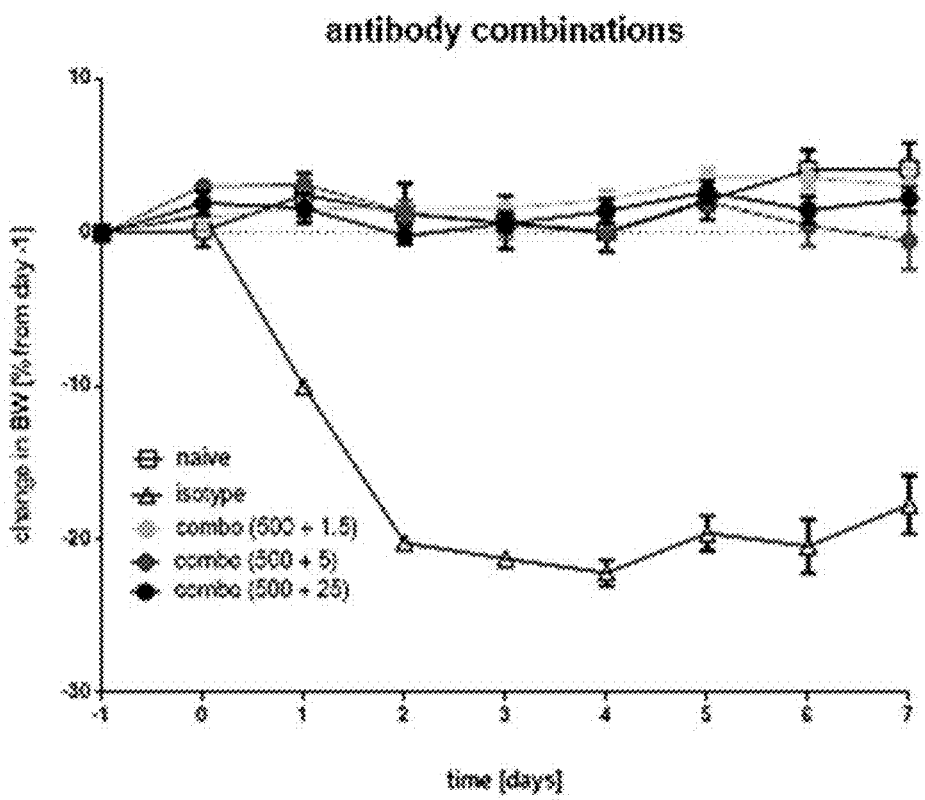

FIGS. 6A, 6B, 6C and 6D show the results of a body weight loss analysis performed on mice dosed with control antibody (FIG. 6A), 500 µg/mouse anti-TNFα antibody alone (FIG. 6B), 1.5, 5, or 25 µg/mouse anti-IL-23p19 antibody alone (FIG. 6C), or a combination of 500 µg/mouse anti-TNFα antibody with 1.5, 5, or 25 µg/mouse anti-IL-23p19 antibody (FIG. 6D). Disease was induced by administration of anti-CD40 antibody. FIG. 6E shows a compilation of the data from the different groups.

Figure 7A:
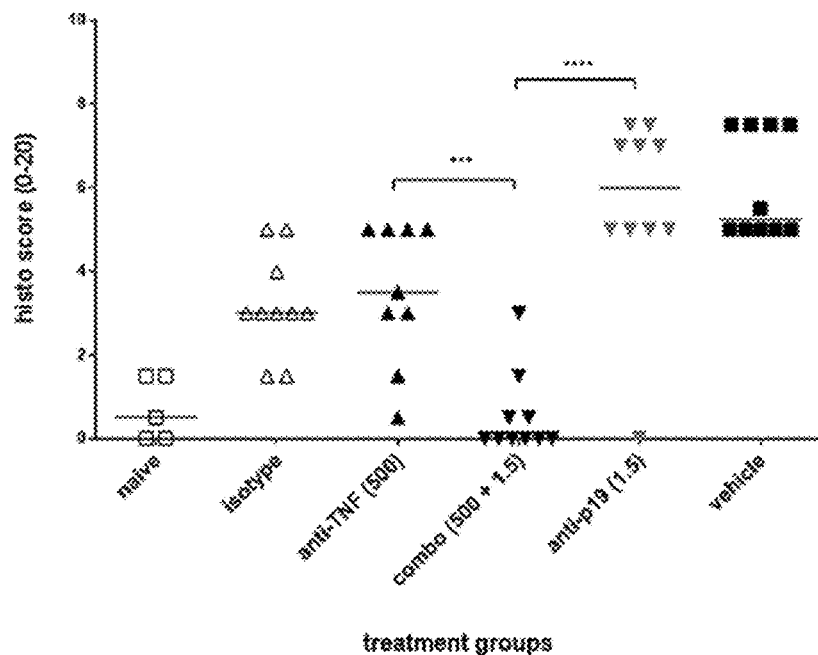
Figure 7B:
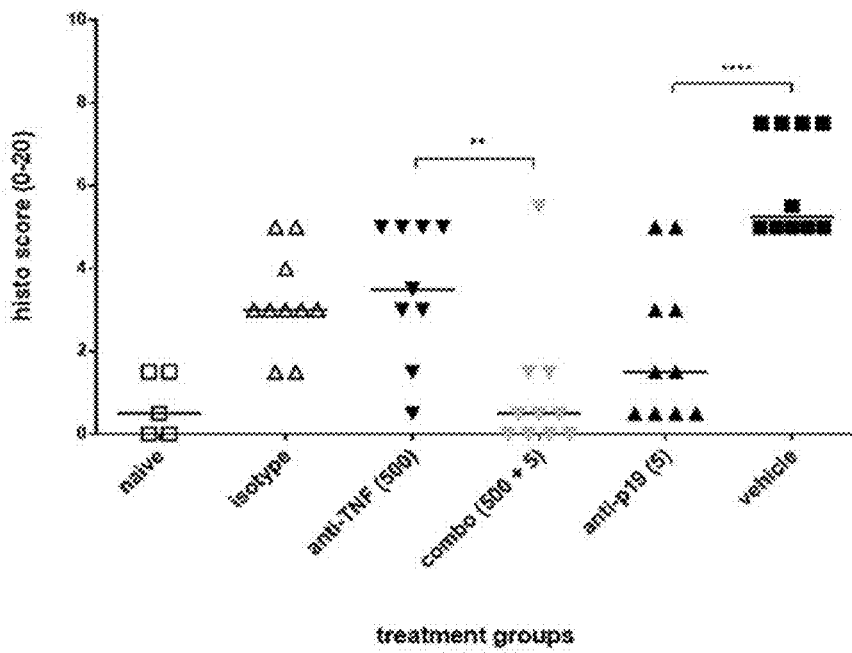
Figure 7C:
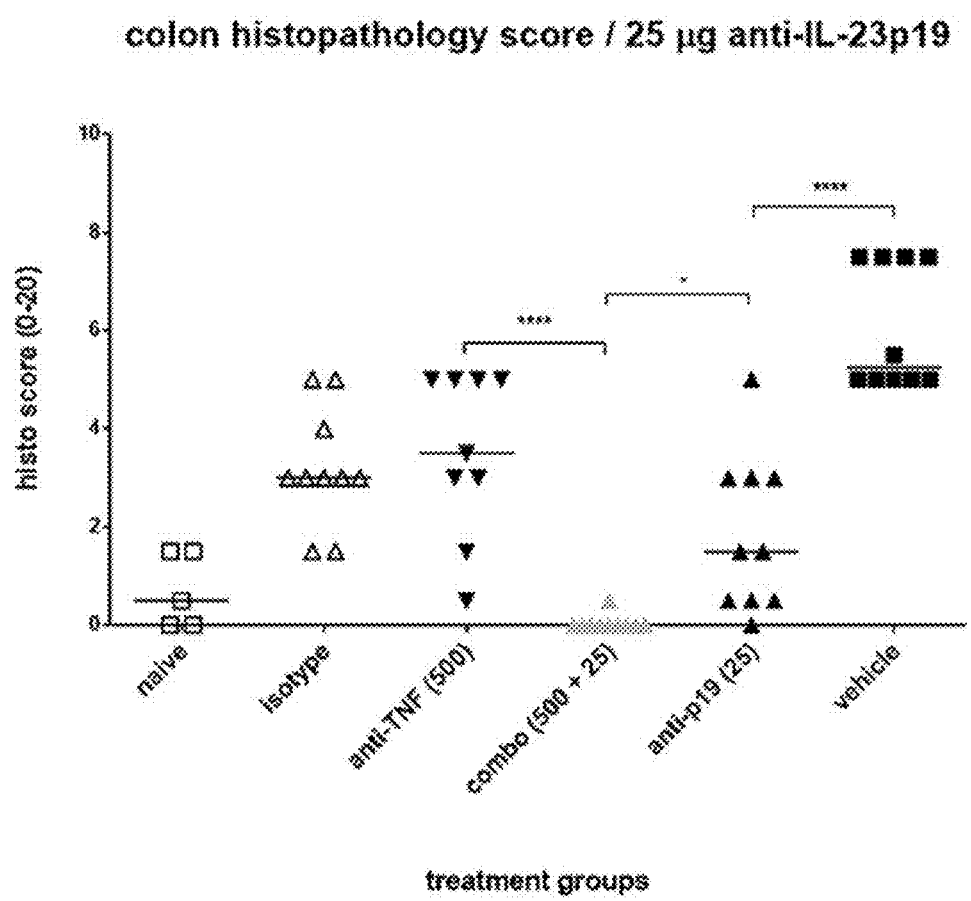

FIGS. 7A, 7B and 7C show the results of a histopathology study performed on the colon of mice dosed with 500 µg/mouse anti-TNFα antibody alone, mouse anti-IL-23p19 antibody alone, or a combination of 500 µg/mouse anti-TNFα antibody with mouse anti-IL-23p19 antibody at an anti-IL23p19 antibody concentration of: 1.5 µg (FIG. 7A), 5 µg (FIG. 7B), or 25 µg (FIG. 7C). Disease was induced by administration of anti-CD40 antibody.

Figure 8:
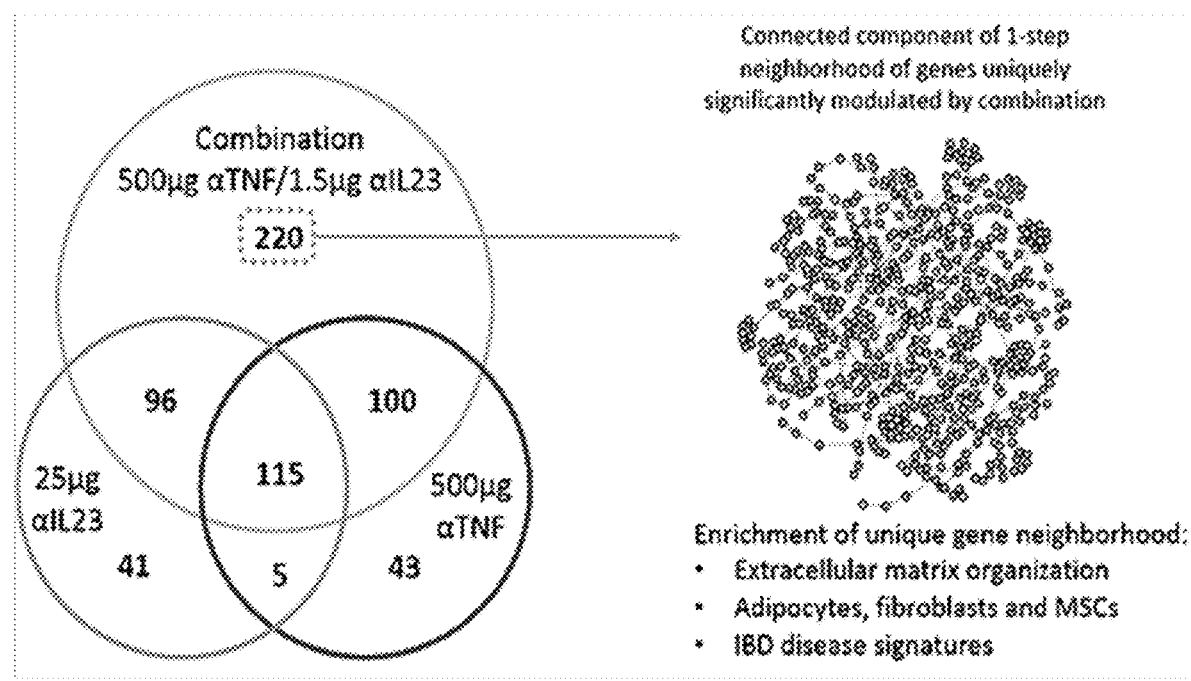

FIG. 8 shows the results of a network analysis based on humanized colonic gene expression signatures of anti-TNFα (500 µg) or high dose anti-IL-23p19 (25 µg) monotherapies that were intersected with a gene expression signature from the combination therapy (500 µg anti-TNFα with 1.5 µg anti-IL-23p19). The analysis was performed to determine whether the molecular response to anti-TNFα and low dose anti-IL-23p19 antibody combination treatment was additive or unique compared with either therapy alone. A unique subnetwork was identified of about 200 genes; the subnetwork was enriched in fibroblasts and extracellular matrix organization, cell types and pathways involved in wound repair and mucosal healing.

DETAILED DESCRIPTION

Definitions:

Unless defined otherwise, technical and scientific terms used herein have the same meaning as commonly understood by one of ordinary skill in the art to which this invention belongs.

As used herein, including the appended claims, the singular forms of words such as "a," "an," and "the," include their corresponding plural references unless the context clearly dictates otherwise.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts a target, such as IL-23 receptor, e.g., in the fluid phase or colloidal phase, but also situations where the agonist or antagonist does not contact the cell or the receptor.

"Treat" or "treating" may also refer to administration of a therapeutic agent, such as a composition described herein, internally or externally to a patient in need of the therapeutic agent. Typically, the agent is administered in an amount effective to prevent or alleviate one or more disease symptoms, or one or more adverse effects of treatment with a different therapeutic agent, whether by preventing the development of, inducing the regression of, or inhibiting the progression of such symptom(s) or adverse effect(s) by any clinically measurable degree. The amount of a therapeutic agent that is effective to alleviate any particular disease symptom or adverse effect (also referred to as the "therapeutically effective amount") may vary according to factors such as the disease state, age, and weight of the patient, the ability of the therapeutic agent to elicit a desired response in the patient, the overall health of the patient, the method, route and dose of administration, and the severity of side effects.

An "inhibitor," as used herein, is any agent that reduces the activity of a targeted molecule. Specifically, an antagonist of IL-23 or TNF-α is an agent that reduces the biological activity of IL-23 or TNF-α, for example by blocking binding of IL-23 or TNF-α to its receptor or otherwise reducing its activity (e.g. as measured in a bioassay).

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof.

Functional fragments include antigen-binding fragments that bind to a mammalian IL-23. For example, antibody fragments capable of binding to IL-23 or portions thereof, include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

"Humanized antibody" refers to an antibody in which the antigen binding sites are derived from non-human species and the variable region frameworks are derived from human immunoglobulin sequences. Humanized antibody may include substitutions in the framework so that the framework may not be an exact copy of expressed human immunoglobulin or human immunoglobulin germline gene sequences.

"Human antibody" refers to an antibody having heavy and light chain variable regions in which both the framework and the antigen binding site are derived from sequences of human origin. If the antibody contains a constant region or a portion of the constant region, the constant region also is derived from sequences of human origin.

"Subject" or "patient" as used interchangeably includes any human or nonhuman animal "Nonhuman animal" includes all vertebrates, e.g., mammals and non-mammals, such as nonhuman primates, sheep, dogs, cats, horses, cows, chickens, amphibians, reptiles, etc.

"Tumor necrosis factor," "TNF" or "TNF-α" refers to the well-known human tumor necrosis factor-α (TNF-α), a multifunctional pro-inflammatory cytokine. TNF-α triggers pro-inflammatory pathways that result in tissue injury, such as degradation of cartilage and bone, induction of adhesion molecules, induction of pro-coagulant activity on vascular endothelial cells, an increase in the adherence of neutrophils and lymphocytes, and stimulation of the release of platelet activating factor from macrophages, neutrophils and vascular endothelial cells.

TNF-α is found as a soluble protein as well as a precursor form called transmembrane TNF-α that is expressed as a cell surface type II polypeptide. Transmembrane TNF-α is processed by metalloproteinases such as TNF-α-converting enzyme (TACE) between residues Ala76 and Val77, resulting in the release of the soluble form of TNF-α of 157 amino acid residues. Soluble TNF-α is a homotrimer of 17-kDa cleaved monomers. Transmembrane TNF-α also exists as a homotrimer of 26-kD uncleaved monomers.

In a first aspect is provided a method of treating an inflammatory bowel disease in a subject. The method comprises administering a first co-therapeutically effective amount of an IL-23 inhibitor and administering a second co-therapeutically effective amount of a TNF-α inhibitor. The method is effective to treat the inflammatory bowel disease, and the first and second co-therapeutically effective amounts are the same or different.

The combination of an anti-TNFα antibody and an anti-IL-23p19 antibody may provide a systemic impact as well as a local impact on the bowel or colon. The combination may provide a greater systemic impact than by treatment with either anti-TNFα antibody or an anti-IL-23p19 antibody alone. The combination can provide for superior anti-inflammatory activity in treating IBD in a human. An anti-IL-23p19 antibody can be highly efficacious in blocking the development of IBD (e.g., colitis and Crohn's disease), but not in blocking anti-CD40-induced body weight loss, while an anti-TNFα antibody can provide substantial protection against anti-CD40-induced body weight loss with some degree of protection against IBD. Each antibody, and the combination, may provide for a differential effect on local versus systemic inflammation.

Various anti-IL-23 antibodies may be used, such as any of the anti-IL-23 antibodies described in U.S. Pat. No. 7,491,391, issued on Feb. 17, 2009, and U.S. Patent Publication No. 2018/0094052, published on Apr. 5, 2018, both of which are incorporated by reference herein.

Various anti-TNFα antibodies may be used. For example, any of the anti-IL-23 antibodies described in U.S. Pat. No. 7,250,165, issued on Jul. 31, 2007, and U.S. Patent Publication No. 2017/0218092, published on Aug. 3, 2017, both of which are incorporated by reference herein, may be used.

Various host animals may be used to produce anti-TNF-α antibodies. For example, Balb/c mice may be used to generate mouse anti-human TNF-α antibodies. The antibodies made in Balb/c mice and other non-human animals may be humanized using various technologies to generate more human-like sequences.

Anti-IL-23 antibodies can optionally be characterized by high affinity binding to IL-23 and, optionally, having low toxicity. Anti-TNFα antibodies can optionally be characterized by high affinity binding to TNFα and, optionally, having low toxicity. In particular, an antibody, specified fragment or variant of the antibody may be used in where the individual components, such as the variable region, constant region and framework, individually and/or collectively, optionally and preferably possess low immunogenicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (less than about 300, preferably less than about 100 measured with a double antigen enzyme immunoassay) (Elliott et al., Lancet 344:1125-1127 (1994), entirely incorporated herein by reference). For the anti-IL-23 antibodies, "low immunogenicity" can also be defined as the incidence of titrable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period. For the anti-TNFα antibodies, "low immunogenicity" can also be defined as the incidence of titratable levels of antibodies to the anti-TNFα antibody in patients treated with anti-TNFα antibody as occurring in less than 25% of patients treated, preferably, in less than 10% of patients treated with the recommended dose for the recommended course of therapy during the treatment period.

At least one anti-IL-23 antibody and anti-TNFα used in the methods described herein can be produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY (1997-2001), each entirely incorporated herein by reference herein.

An anti-IL-23 antibody and/or an anti-TNF-α antibody can also be generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

The anti-IL-23 antibodies used in the methods described herein can also be prepared using at least one anti-IL-23 antibody encoding nucleic acid to provide transgenic animals or mammals, such as goats, cows, horses, sheep, rabbits, and the like, that produce such antibodies in their milk. The anti-TNF-α antibodies used in the methods described herein can also be prepared using at least one anti-TNF-α antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

The anti-IL-23 antibodies can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The anti-TNF-α antibodies can bind human TNF-α with a wide range of affinities ($K_D$). In a preferred embodiment, a human mAb can optionally bind human TNF-α with high affinity. For example, a human mAb can bind human TNF-α with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The anti-IL-23 antibodies may be an IgG1, IgG2, IgG3 or IgG4 isotype. The anti-TNF-α antibodies may be an IgG1, IgG2, IgG3 or IgG4 isotype.

Without wishing to be bound by theory, the benefits of combining an anti-IL-23p19 antibody with an anti-TNFα antibody can arise from distinct gene expression changes induced by each antibody. As described in the Example 1 and at least in FIGS. 2A and 2B, at doses where each antibody provided similar protection against colonic inflammation (FIG. 2, 50 μg anti-IL-23p19 and 500 μg anti-TNFα), distinct intestinal gene expression changes were observed in mice when blocking IL-23p19 compared to blocking TNFα. These gene expression changes may apply to human disease as well. Integration of 'humanized' murine anti-TNFα and anti-IL-23p19 gene signatures with a human intestinal biopsy gene network can allow for focus only on genes that were expressed and varied in human intestinal tissues. Additional context for the potential molecular impact of each antibody on human IBD can be obtained by generating treatment subnetworks that included genes one step removed in the network (i.e. strongly correlated) from genes within each signature. Individual anti-TNFα and anti-IL-23p19 subnetworks show unique single antibody gene signatures, allowing for insight into the biology targeted by both mechanisms.

Effectiveness of treatment according to the methods described herein can be determined, for example, by assessing the degree of weight loss, nutrient absorption, and histopathological studies of tissue samples. Histopathological studies can include measurement of one or more of submucosal edema, inflammation, gland loss, erosion, mucosal thickness, and hyperplasia. Submucosal edema can be quantified by measuring thickness from the muscularis mucosa to the internal border of the outer muscle layer (e.g., in a nontangential area thought to best represent the severity of this change). Inflammation scoring can reflect the extent of macrophage, lymphocyte, and neutrophil infiltration into the colon. Gland loss of the crypt epithelium and remaining gland epithelium can be quantitated by assessing the percentage of the mucosa affected. Erosion reflects a loss of surface epithelium and can be scored by assessing the percentage of mucosa that is affected (e.g., by mucosal hemorrhage). Mucosal thickness can be assessed by measuring a non-tangential area of the section that best represents the overall mucosal thickness. Increased thickness reflects gland elongation and mucosal hyperplasia.

An overall histopathology score can be derived from measurements of one or more of submucosal edema, inflammation, gland loss, erosion, mucosal thickness, and hyperplasia. An exemplary scoring system for mice is described in Example 1. A similar system can be used for human and other mammalian subjects.

In some embodiments, the inflammatory bowel disease is colitis, e.g., ulcerative colitis. Colitis can involve irritation, swelling and other signs of inflammation of the colon. Sores and ulcers are present in ulcerative colitis.

In some embodiments, the inflammatory bowel disease is Crohn's disease. Crohn's disease may be confined to the colon, but may also be present in other tissues such as the small intestine. Crohn's disease can involve inflammation of the colon and small intestine. There may even be inflammation of the mouth, anus, skin, eyes, joints, and/or liver.

In some embodiments, the subject was previously treated with a TNF-α inhibitor alone and the inflammatory bowel disease did not undergo remission after the previous treatment. In some embodiments, the subject was previously treated with IL-23 inhibitor alone and the inflammatory bowel disease did not undergo remission after the previous treatment. The methods described herein may be beneficial for subjects who did not respond to monotherapy treatments with either TNF-α inhibitor (e.g., an anti-TNF-α antibody) or IL-23 inhibitor (e.g., an anti-IL-23p19 antibody). Based on results described herein showing substantial improvement in histopathology of the colon when administering both an anti-TNF-α antibody and an anti-IL-23p19 antibody (as compared to either antibody alone), subjects may respond much better to the combination of a TNF-α inhibitor (e.g., an anti-IL-23p19 antibody) and an IL-23 inhibitor (e.g., an anti-IL-23p19 antibody).

In various embodiments, the IL-23 inhibitor comprises an anti-IL-23p19 antibody or an antigen-binding fragment thereof. These can bind to the p19 subunit of IL-23.

In various embodiments, the TNF-α inhibitor comprises an anti-TNF-α antibody or an antigen-binding fragment thereof. In some embodiments, the anti-IL-23p19 antibody comprises a human antibody or a humanized antibody. In some embodiments, the anti-TNF-α antibody comprises a human antibody or a humanized antibody.

Anti-IL-23 antibodies and/or anti-TNFα antibodies can also be humanized or prepared as human antibodies engineered with retention of high affinity for the antigen and other favorable biological properties. Humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), and U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference.

In another aspect is provided a method of reducing inflammation of the colon in a subject who has inflammatory bowel disease. The method comprises administering a first co-inflammation reducing effective amount of an IL-23 inhibitor and administering a second co-inflammation reducing effective amount of a TNF-α inhibitor. The method is effective to reduce inflammation of the colon of the subject to a level comparable to the colon of a normal patient. The first and second co-inflammation reducing effective amounts are the same or different. Prevention or reduction of inflammation can be measured by histopathological analysis, degree of weight loss, and degree of inflammation.

In some embodiments, in a histopathology study of a tissue sample from the colon of the subject after administration of the IL-23 inhibitor and the TNF-α inhibitor, the inflammation score is very minimal or normal. Very minimal inflammation may reflect the presence of just one or two small foci, with mononuclear inflammatory cells (MNIC) likely background mucosal lymphoid aggregates.

In some embodiments, in a histopathology study of a tissue sample from the colon of the subject after administration of the IL-23 inhibitor and the TNF-α inhibitor, the gland loss score is very minimal or normal. Very minimal gland loss may involve only one or two small focal areas of gland loss.

In some embodiments, in a histopathology study of a tissue sample from the colon of the subject after administration of the IL-23 inhibitor and the TNF-α inhibitor, the erosion score is very minimal or normal. Very minimal erosion may involve only one or two small focal areas of mucosal erosion.

In some embodiments, in a histopathology study of a tissue sample from the colon of the subject after administration of the IL-23 inhibitor and the TNF-α inhibitor, the mucosal thickness and hyperplasia score are independently very minimal or normal. Very minimal mucosal thickness may involve less than a 25% increase in mucosal thickness as compared to the thickness of normal mucosal tissue.

In some embodiments, after administration of the IL-23 inhibitor and the TNF-α inhibitor, the histopathology of the colon is about identical (or identical) to that of normal tissue. The histopathology can be assessed by measuring one or more of submucosal edema, inflammation, gland loss, erosion, mucosal thickness, and hyperplasia. Any or all of these parameters may be measured and scored. An exemplary scoring system is described in Example 1.

In various embodiments, the IL-23 inhibitor is an anti-IL-23p19 antibody or an antigen-binding fragment thereof. Exemplary anti-IL-23p19 antibodies and fragments are described in U.S. Pat. No. 7,491,391, issued on Feb. 17, 2009 and incorporated by reference herein in its entirety. In various embodiments, the TNF-α inhibitor is an anti-TNF-α antibody or an antigen-binding fragment thereof.

In some embodiments, the anti-TNFα antibody and the anti-IL-23p19 antibody are administered in a ratio of from 1:2 to 2:1 (w/w). The ratio may be calculated from the dosage of one antibody in a patient in mg/kg and the dosage of the other antibody in the same patient in mg/kg. In some embodiments, the anti-TNFα antibody and the anti-IL-23p19 antibody are administered in a ratio of from 15:1 to 400:1 (w/w). The ratio may be calculated from the dosage of one antibody in a patient in mg/kg and the dosage of the other antibody in the same patient in mg/kg.

Administration to a subject (e.g., human patient) of anti-TNFα antibody and an anti-IL-23p19 antibody in a ratio of from 1:2 to 2:1 (w/w) can provide for enhanced treatment of IBD (e.g., colitis and Crohn's disease) in the subject. In some embodiments, the ratio of anti-TNFα antibody to anti-IL-23p19 antibody is from 1:2 to 1:1.8 (w/w). In some embodiments, the ratio of anti-TNFα antibody to anti-IL-23p19 antibody is from 1:1.9 to 1:1.7 (w/w). In some embodiments, the ratio of anti-TNFα antibody to anti-IL-23p19 antibody is from 1:1.8 to 1:1.6 (w/w). In some embodiments, the ratio of anti-TNFα antibody to anti-IL-23p19 antibody is from 1:1.7 to 1:1.5 (w/w). In some embodiments, the ratio of anti-TNFα antibody to anti-IL-23p19 antibody is from 1:1.6 to 1:1.4 (w/w). In some embodiments, the ratio of anti-TNFα antibody to anti-IL-23p19 antibody is from 1:1.5 to 1:1.3 (w/w). In some embodiments, the ratio of anti-TNFα antibody to anti-IL-23p19 antibody is from 1:1.4 to 1:1.2 (w/w). In some embodiments, the ratio of anti-TNFα antibody to anti-IL-23p19 antibody is from 1:1.3 to 1:1.1 (w/w). In some embodiments, the ratio of anti-TNFα antibody to anti-IL-23p19 antibody is from 1:1.2 to 1:1 (w/w). In some embodiments, the ratio of anti-TNFα antibody to anti-IL-23p19 antibody is from 1:1.1 to 1.1:1 (w/w). In some embodiments, the ratio of anti-TNFα antibody to anti-IL-23p19 antibody is from 1:1 to 1.2:1 (w/w). In some embodiments, the ratio of anti-TNFα antibody to anti-IL-23p19 antibody is from 1.1:1 to 1.3:1 (w/w). In some embodiments, the ratio of anti-TNFα antibody to anti-IL-23p19 antibody is from 1.2:1 to 1.4:1 (w/w). In some embodiments, the ratio of anti-TNFα antibody to anti-IL-23p19 antibody is from 1.3:1 to 1.5:1

(w/w). In some embodiments, the ratio of anti-TNFα antibody to anti-IL-23p19 antibody is from 1.4:1 to 1.6:1 (w/w). In some embodiments, the ratio of anti-TNFα antibody to anti-IL-23p19 antibody is from 1.5:1 to 1.7:1 (w/w). In some embodiments, the ratio of anti-TNFα antibody to anti-IL-23p19 antibody is from 1.6:1 to 1.8:1 (w/w). In some embodiments, the ratio of anti-TNFα antibody to anti-IL-23p19 antibody is from 1.7:1 to 1.9:1 (w/w). In some embodiments, the ratio of anti-TNFα antibody to anti-IL-23p19 antibody is from 1.8:1 to 2:1 (w/w). In some embodiments, the ratio of anti-IL-23p19 antibody to anti-TNFα antibody is about 1:2, 1:1.8, 1:1.5, 1:1.2, 1:1, 1.2:1, 1.5:1, 1.8:1 or 2:1 (w/w).

A minimally active dose of an anti-IL-23p19 antibody can be administered to the subject (e.g., human patient) with a larger dose of anti-TNFα antibody to prevent development of inflammatory bowel disease (e.g., colitis and Crohn's disease). The ratio of the minimally active dose of anti-IL-23p19 to the ratio of the larger dose of anti-TNFα antibody can range from 1:400 to 1:15 (w/w). In some embodiments, the ratio of anti-IL-23p19 antibody to anti-TNFα antibody is from 1:400 to 1:350 (w/w). In some embodiments, the ratio of anti-IL-23p19 antibody to anti-TNFα antibody is from 1:370 to 1:320 (w/w). In some embodiments, the ratio of anti-IL-23p19 antibody to anti-TNFα antibody is from 1:350 to 1:300 (w/w). In some embodiments, the ratio of anti-IL-23p19 antibody to anti-TNFα antibody is from 1:300 to 1:250 (w/w). In some embodiments, the ratio of anti-IL-23p19 antibody to anti-TNFα antibody is from 1:280 to 1:230 (w/w). In some embodiments, the ratio of anti-IL-23p19 antibody to anti-TNFα antibody is from 1:250 to 1:200 (w/w). In some embodiments, the ratio of anti-IL-23p19 antibody to anti-TNFα antibody is from 1:220 to 1:170 (w/w). In some embodiments, the ratio of anti-IL-23p19 antibody to anti-TNFα antibody is from 1:170 to 1:120 (w/w). In some embodiments, the ratio of anti-IL-23p19 antibody to anti-TNFα antibody is from 1:150 to 1:100 (w/w). In some embodiments, the ratio of anti-IL-23p19 antibody to anti-TNFα antibody is from 1:120 to 1:80 (w/w). In some embodiments, the ratio of anti-IL-23p19 antibody to anti-TNFα antibody is from 1:100 to 1:60 (w/w). In some embodiments, the ratio of anti-IL-23p19 antibody to anti-TNFα antibody is from 1:80 to 1:40 (w/w). In some embodiments, the ratio of anti-IL-23p19 antibody to anti-TNFα antibody is from 1:60 to 1:30 (w/w). In some embodiments, the ratio of anti-IL-23p19 antibody to anti-TNFα antibody is from 1:50 to 1:25 (w/w). In some embodiments, the ratio of anti-IL-23p19 antibody to anti-TNFα antibody is from 1:40 to 1:20 (w/w). In some embodiments, the ratio of anti-IL-23p19 antibody to anti-TNFα antibody is from 1:35 to 1:15 (w/w). In some embodiments, the ratio of anti-IL-23p19 antibody to anti-TNFα antibody is about 1:400, 1:300, 1:200, 1:150, 1:100, 1:75, 1:50, 1:25, or 1:15 (w/w).

In some embodiments, the anti-TNFα antibody and the anti-IL-23p19 antibody are administered in a ratio of from 15:1 to 400:1 (w/w). In some embodiments, the a) anti-IL-23p19 antibody or the antigen-binding fragment thereof and the b) anti-TNF-α antibody or the antigen-binding fragment thereof are administered simultaneously. In some embodiments, the a) anti-IL-23p19 antibody or the antigen-binding fragment thereof and the b) anti-TNF-α antibody or the antigen-binding fragment thereof are administered sequentially. The a) anti-IL-23p19 antibody or the antigen-binding fragment thereof and the b) anti-TNF-α antibody or the antigen-binding fragment thereof may be administered within one hour, two hours, three hours, six hours, 12 hours, one day, two days, three days, or four days of one another.

In some embodiments, the combination of the a) anti-IL-23p19 antibody or the antigen-binding fragment thereof and the b) anti-TNF-α antibody or the antigen-binding fragment is effective to treat a subject who was previously treated with an anti-TNF-α antibody alone without significant remission of the inflammatory bowel disease. In some embodiments, the combination of the a) anti-IL-23p19 antibody or the antigen-binding fragment thereof and the b) anti-TNF-α antibody or the antigen-binding fragment is effective to treat a subject who was previously treated with an anti-IL-23p19 antibody alone without significant remission of the inflammatory bowel disease.

In another aspect is provided a method of treating inflammatory bowel disease in a human subject. The method comprises: (a) administering 0.0005 to 0.002 mg/kg of an anti-IL-23p19 antibody or an antigen-binding fragment thereof; and (b) administering 0.020 to 0.125 mg/kg of an anti-TNF-α antibody or an antigen-binding fragment thereof. In various embodiments, the method is effective to treat the inflammatory bowel disease. In some embodiments, the inflammatory bowel disease is colitis. In some embodiments, the inflammatory bowel disease is Crohn's disease. In some embodiments, the method is effective to inhibit weight loss (e.g., weight loss associated with the inflammatory bowel disease.)

The (a) anti-IL-23p19 antibody or the antigen-binding fragment thereof and the (b) anti-TNF-α antibody or the antigen-binding fragment thereof may be administered simultaneously, sequentially, or within one day of one another.

In various embodiments, administration to a subject (e.g., human patient) of 0.020 to 0.125 mg/kg anti-TNFα antibody and 0.020 to 0.125 mg/kg of an anti-IL-23p19 antibody can provide for enhanced treatment of IBD (e.g., colitis and Crohn's disease) in the subject. Initial results from evaluating the combination of 50 μg each anti-TNFα and anti-IL-23p19 in mice suggest that the combination provides enhanced protection against colitis versus single treatments at the same dose. See Example 1. In some embodiments, 0.020 to 0.040 mg/kg anti-TNFα antibody and 0.020 to 0.040 mg/kg of an anti-IL-23p19 antibody are administered to a human subject. In some embodiments, 0.030 to 0.050 mg/kg anti-TNFα antibody and 0.030 to 0.050 mg/kg of an anti-IL-23p19 antibody are administered to a human subject. In some embodiments, 0.040 to 0.060 mg/kg anti-TNFα antibody and 0.040 to 0.060 mg/kg of an anti-IL-23p19 antibody are administered to a human subject. In some embodiments, 0.050 to 0.070 mg/kg anti-TNFα antibody and 0.050 to 0.070 mg/kg of an anti-IL-23p19 antibody are administered to a human subject. In some embodiments, 0.060 to 0.080 mg/kg anti-TNFα antibody and 0.060 to 0.080 mg/kg of an anti-IL-23p19 antibody are administered to a human subject. In some embodiments, 0.070 to 0.090 mg/kg anti-TNFα antibody and 0.070 to 0.090 mg/kg of an anti-IL-23p19 antibody are administered to a human subject. In some embodiments, 0.080 to 0.100 mg/kg anti-TNFα antibody and 0.080 to 0.100 mg/kg of an anti-IL-23p19 antibody are administered to a human subject. In some embodiments, 0.090 to 0.110 mg/kg anti-TNFα antibody and 0.090 to 0.110 mg/kg of an anti-IL-23p19 antibody are administered to a human subject. In some embodiments, 0.100 to 0.125 mg/kg anti-TNFα antibody and 0.100 to 0.125 mg/kg of an anti-IL-23p19 antibody are administered to a human subject.

In various embodiments, the anti-IL-23p19 antibody is administered to the subject (e.g., human patient) daily, every two days, every three days, every four days, every five days, every six days, or once every week. In various embodiments, the anti-TNFα antibody is administered to the subject (e.g., human patient) daily, every two days, every three days, every four days, every five days, every six days, or once every week. In some embodiments, both the anti-IL-23p19 antibody and the anti-TNFα antibody are administered daily, every two days, every three days, every four days, every five days, every six days, or once every week.

The anti-IL-23p19 antibody and the anti-TNFα antibody can be administered conjointly to the subject (e.g., human patient). Alternatively, the anti-IL-23p19 antibody and the anti-TNFα antibody can be administered separately to the subject. If administered separately, the antibodies may be administered within three hours, six hours, twelve hours, one day, two days, three days, or four days of one another.

In some embodiments, the combination of the a) anti-IL-23p19 antibody or the antigen-binding fragment thereof and the b) anti-TNF-α antibody or the antigen-binding fragment is effective to treat a subject who was previously treated with an anti-TNF-α antibody alone without significant remission of the inflammatory bowel disease. In some embodiments, the combination of the a) anti-IL-23p19 antibody or the antigen-binding fragment thereof and the b) anti-TNF-α antibody or the antigen-binding fragment is effective to treat a subject who was previously treated with an anti-IL-23p19 antibody alone without significant remission of the inflammatory bowel disease.

In another aspect, a minimally active dose of an anti-IL-23p19 antibody can be administered with a larger dose of anti-TNFα antibody to prevent relapse of inflammatory bowel disease (e.g., ulcerative colitis, indeterminate colitis and/or Crohn's disease) when the subject is in remission from inflammatory bowel disease. The ratio of the minimally active dose of anti-IL-23p19 to the ratio of the larger dose of anti-TNFα antibody can range from 1:400 to 1:15 (w/w). In some embodiments, the ratio of anti-IL-23p19 antibody to anti-TNFα antibody is from 1:400 to 1:350 (w/w). In some embodiments, the ratio of anti-IL-23p19 antibody to anti-TNFα antibody is from 1:370 to 1:320 (w/w). In some embodiments, the ratio of anti-IL-23p19 antibody to anti-TNFα antibody is from 1:350 to 1:300 (w/w). In some embodiments, the ratio of anti-IL-23p19 antibody to anti-TNFα antibody is from 1:300 to 1:250 (w/w). In some embodiments, the ratio of anti-IL-23p19 antibody to anti-TNFα antibody is from 1:280 to 1:230 (w/w). In some embodiments, the ratio of anti-IL-23p19 antibody to anti-TNFα antibody is from 1:250 to 1:200 (w/w). In some embodiments, the ratio of anti-IL-23p19 antibody to anti-TNFα antibody is from 1:220 to 1:170 (w/w). In some embodiments, the ratio of anti-IL-23p19 antibody to anti-TNFα antibody is from 1:170 to 1:120 (w/w). In some embodiments, the ratio of anti-IL-23p19 antibody to anti-TNFα antibody is from 1:150 to 1:100 (w/w). In some embodiments, the ratio of anti-IL-23p19 antibody to anti-TNFα antibody is from 1:120 to 1:80 (w/w). In some embodiments, the ratio of anti-IL-23p19 antibody to anti-TNFα antibody is from 1:100 to 1:60 (w/w). In some embodiments, the ratio of anti-IL-23p19 antibody to anti-TNFα antibody is from 1:80 to 1:40 (w/w). In some embodiments, the ratio of anti-IL-23p19 antibody to anti-TNFα antibody is from 1:60 to 1:30 (w/w). In some embodiments, the ratio of anti-IL-23p19 antibody to anti-TNFα antibody is from 1:50 to 1:25 (w/w). In some embodiments, the ratio of anti-IL-23p19 antibody to anti-TNFα antibody is from 1:40 to 1:20 (w/w). In some embodiments, the ratio of anti-IL-23p19 antibody to anti-TNFα antibody is from 1:35 to 1:15 (w/w). In some embodiments, the ratio of anti-IL-23p19 antibody to anti-TNFα antibody is about 1:400, 1:300, 1:200, 1:150, 1:100, 1:75, 1:50, 1:25, or 1:15 (w/w).

In various embodiments, the anti-IL-23p19 antibody is administered daily, every two days, every three days, every four days, every five days, every six days, or once every week. In various embodiments, the anti-TNFα antibody is administered daily, every two days, every three days, every four days, every five days, every six days, or once every week. In some embodiments, both the anti-IL-23p19 antibody and the anti-TNFα antibody are administered daily, every two days, every three days, every four days, every five days, every six days, or once every week.

The anti-IL-23p19 antibody and the anti-TNFα antibody can be administered conjointly. Alternatively, the anti-IL-23p19 antibody and the anti-TNFα antibody can be administered separately.

Combining anti-TNFα antibody (500 μg/mouse) treatment with minimally active doses of anti-IL-23p19 antibody can provide superior efficacy in preventing development of colitis when compared to either single antibody treatment at these doses. See, e.g., Example 5. An analysis of colonic gene signatures of this combination therapy versus anti-TNFα or anti-IL-23p19 monotherapy identified a unique set of genes modulated by combination therapy enriched in fibroblasts and extracellular matrix organization, cell types and pathways involved in wound repair. This novel finding indicates that a combination treatment of antibodies against TNFα and IL-23p19 can provide for superior efficacy in treating colitis and inflammatory bowel syndrome. Further, a combination treatment of antibodies against TNFα and IL-23p19 may have synergistic effects due to modulation of specific gene networks implicated in mucosal healing.

The data in Example 5 demonstrates that combination treatment with antibodies against TNFα and IL-23p19 can provide superior protection against colitis, as compared to treatment with either antibody as monotherapy. The colitis may be acute colitis. Without wishing to be bound by theory, transcriptomics and gene network analyses identified both overlapping and distinct molecular effects for each monotherapy and revealed a unique set of genes influenced by the combination treatment that are implicated in wound repair processes. Taken together, these findings suggest that combination therapy with anti-TNFα and anti-IL-23p19 antibodies can provide a synergistic impact on alleviating intestinal inflammation. The synergistic impact may arise through the targeting of common inflammatory pathways. The synergistic impact may arise from treatment of distinct cell types implicated in IBD pathogenesis with an impact on genes involved in tissue restoration.

In some embodiments, the combination of the a) anti-IL-23p19 antibody or the antigen-binding fragment thereof and the b) anti-TNF-α antibody or the antigen-binding fragment is effective to treat a subject who was previously treated with an anti-TNF-α antibody alone without significant remission of the inflammatory bowel disease. In some embodiments, the combination of the a) anti-IL-23p19 antibody or the antigen-binding fragment thereof and the b) anti-TNF-α antibody or the antigen-binding fragment is effective to treat a subject who was previously treated with an anti-IL-23p19 antibody alone without significant remission of the inflammatory bowel disease.

Formulations

Each of the anti-TNFα and anti-IL-23 (e.g., anti-IL-23p19) antibodies may be present in stable formulations. The stable formulations may comprise a phosphate buffer with saline or a chosen salt, as well as preserved solutions and formulations containing a preservative as well as multi-use preserved formulations suitable for pharmaceutical or veterinary use, comprising an anti-IL-23 (e.g., anti-IL-23p19) antibody in a pharmaceutically acceptable formulation. Preserved formulations may contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, polymers, or mixtures thereof in an aqueous diluent. Any suitable concentration or mixture can be used, such as about 0.0015%, or any range, value, or fraction therein. Non-limiting examples include, without preservative, about 0.1-2% m-cresol (e.g., 0.2, 0.3, 0.4, 0.5, 0.9, 1.0%), about 0.1-3% benzyl alcohol (e.g., 0.5, 0.9, 1.1, 1.5, 1.9, 2.0, 2.5%), about 0.001-0.5% thimerosal (e.g., 0.005, 0.01), about 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

The aqueous diluent may further comprise a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or nonionic surfactants, such as polysorbate 20 or 80 or poloxamer 184 or 188, Pluronic® polyls, other block co-polymers, and chelators, such as EDTA and EGTA, can be added to the formulations or compositions to reduce aggregation. These additives may be useful if a pump or plastic container is used to administer the formulation. The presence of pharmaceutically acceptable surfactant can reduce any propensity for an antibody to aggregate.

The formulations of the present invention can be prepared by a process that comprises mixing at least one anti-IL-23 antibody or anti-TNFα antibody with a selected buffer. The buffer can be a phosphate buffer containing saline or a chosen salt. Mixing the at least one anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

Stable or preserved formulations comprising one or both of anti-IL-23 antibody and anti-TNFα antibody can be provided to patients as clear solutions or as dual vials comprising a vial of lyophilized at least one antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

For parenteral administration, the anti-IL-23 antibody or anti-TNFα antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and about 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Many known and developed modes can be used according to the present invention for administering pharmaceutically effective amounts of at least one anti-IL-23 antibody or anti-TNFα antibody. While pulmonary administration is used in the following description, other modes of administration can be used according to the present invention with suitable results. IL-23p19 antibodies of the present invention can be delivered in a carrier, as a solution, emulsion, colloid, or suspension, or as a dry powder, using any of a variety of devices and methods suitable for administration by inhalation or other modes described here within or known in the art.

Formulations for parenteral administration may comprise a common excipient. Exemplary common excipients include, but are not limited to, sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides.

Formulations for oral administration may include the co-administration of adjuvants (e.g., resorcinols and non-ionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and antibodies and a combination of at least two surfactants intended for oral, buccal, mucosal, nasal, pulmonary, vaginal trans-membrane, or rectal administration are taught in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, α-tocopherol, antioxidant such as cysteine, disintegrator, binder, thickener, buffering agent, sweetening agent, flavoring agent, perfuming agent, etc.

It can be desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the compounds of the present invention or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Dose Range Determination for Single Treatments with Antibody Against TNFα or IL-23p19 and Combination Studies in the CD40 Antibody-Induced Colitis Model Three separate studies were conducted. In all three studies, animals were randomized by weight, assigned to treatment groups and labeled by a specific number from 1-10 for each group. Vehicle (PBS) and mAb treatments were administered as a single intraperitoneal (ip) injection one day before (day −1) disease was induced by injecting 0.2 mg CD40 agonist antibody in 0.2 ml PBS per animal ip (day 0).

Naive control mice were not treated and were kept in a separate cage until termination at day 7. Observations for clinical signs of disease were conducted daily. Body weights were measured and recorded daily from day −1 until termination at day 7. At study termination (day 7), the animals were euthanized by $CO_2$ overdose and colon tissues removed and processed accordingly for histological analysis.

Following euthanasia, the colon, defined as the intestinal segment between cecum and rectum, was excised and flushed with ice cold PBS to remove fecal content. One centimeter of the proximal colon was placed in histology cassettes and submerged into a fixative solution (10% Neutral Buffered Formalin, NBF). After 24 hours the cassettes were removed from the fixative and transferred to 70% ethanol and stored refrigerated until processing. The remaining colon tissue was divided into three equal parts; the first third snap frozen in liquid nitrogen for PK analysis, the second third snap frozen in liquid nitrogen for cytokine analysis, and the last third (distal, close to rectum) stored in 1 ml RNAlater (Ambion™) on ice until all animals had been euthanized and tissues removed accordingly and then frozen for RNA extraction and gene expression analysis. All frozen samples were stored at −80° C. until further processing.

In all three studies, animals were randomized by weight, assigned to treatment groups and labeled by a specific number from 1-10 for each group. Vehicle (PBS) and mAb treatments were administered as a single intraperitoneal (ip) injection one day before (day −1) disease was induced by injecting 0.2 mg CD40 agonist antibody in 0.2 ml PBS per animal ip (day 0). Naïve control mice were not treated and were kept in a separate cage until termination at day 7. Observations for clinical signs of disease were conducted daily. Body weights were measured and recorded daily from day −1 until termination at day 7. The animals were euthanized at day 7 by $CO_2$ overdose and colon tissues removed and processed accordingly for histological analysis.

In the first study (Study 1), anti-TNFα or anti-IL-23p19 mAbs were evaluated in a CD40 colitis model. These antibodies were evaluated individually at doses of 500 μg or 50 μg per mouse, or in combination (i.e., 500 μg+500 μg/mouse each or 50+50 μg/mouse each). The protocol is summarized in Table 1 below.

TABLE 1

Evaluation of single antibody treatment against TNFα and IL-23p19 versus combination (at equal high and low doses) in the CD40 colitis model/Study 1, ELN: Immunopharmacology WC-2018-00034

| Test article | Route | Dose | Number of animals |
|---|---|---|---|
| Naïve | | None | 3 |
| Vehicle (PBS) | ip | 10 ml/kg, day −1 | 5 |
| CNTO 6601 | ip | 1000 µg/mouse, day −1 | 9 |
| CNTO 5048 | ip | 50 µg/mouse, day −1 | 9 |
| CNTO 5048 | ip | 500 µg/mouse, day −1 | 9 |
| CNTO 3723 | ip | 50 µg/mouse, day −1 | 9 |
| CNTO 3723 | ip | 500 µg/mouse, day −1 | 9 |
| CNTO 3723 + CNTO 5048 | ip | 50 + 50 µg/mouse, day −1 | 10 |
| CNTO 3723 + CNTO 5048 | ip | 500 + 500 µg/mouse, day −1 | 10 |

CNTO 3723 is a murine anti-IL-23p19 monoclonal antibody (neutralizing IL-23p19 mAb). CNTO 5048 is a murine anti-TNFα monoclonal antibody (neutralizing TNFα mAb). CNTO 6601 refers to the isotype control used throughout the experiments. CNTO 6601 does not specifically bind to either TNFα or IL-23p19.

Anti-inflammatory activity of anti-TNFα and anti-IL-23p19 antibody treatment, alone or in combination, was assessed in the anti-CD40 antibody induced colitis model. Ligation of the co-stimulatory receptor CD40 via an agonist antibody causes an acute innate systemic and colonic inflammatory response in lymphopenic (T and B cell-deficient) RAG2$^{−/−}$ mice where the inflammatory response in the colon peaks around day 7, followed by resolution (ELN Immunopharmacology WC-2015-00008). IL-23 drives local colonic inflammation in this model.

While the expression of TNFα controls manifestations of systemic disease (e.g., body weight loss), TNFα has only modest effects on colitis development. (1) The inventors sought to investigate the distinct molecular impact of anti-TNFα versus anti-IL-23p19 antibody treatment on intestinal gene expression and determine whether combination treatment of anti-TNFα and anti-IL-23p19 exhibited enhanced efficacy over either monotherapy. At day −1, RAG2$^{−/−}$ mice were dosed once ip with 0.5 mg or 0.05 mg anti-TNFα antibody (CNTO5048), 0.5 mg or 0.05 mg anti-IL-23p19 antibody (CNTO3732), a combination of both antibodies (0.5 mg or 0.05 mg each), 1.0 mg isotype control antibody (CNTO6601), or 10 ml/kg PBS. (The RAG2$^{−/−}$ mice used in all examples herein are 8-10 week old female mice sourced from Taconic Farms.) One day later, at day 0, all animals were challenged ip with anti-CD40 antibody (0.2 mg) to induce inflammation.

Body weight loss analysis was performed after low dose (50 µg) and high dose (500 µg) antibody treatment. Body weight was monitored from day −1, when the mice were injected with antibody or PBS, until termination on day 7.

Figure 1A:
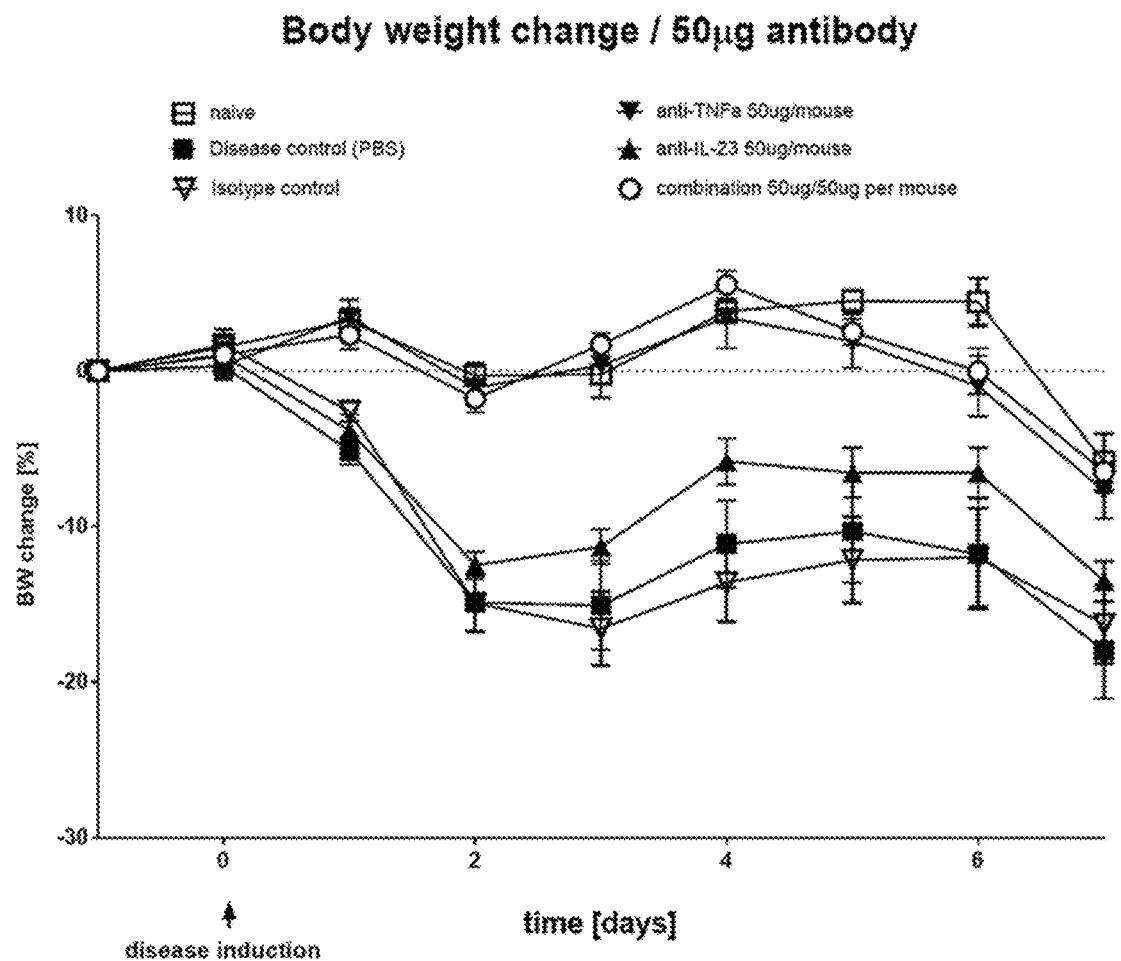
FIGS. 1A and 1B show the results of a body weight loss analysis performed on mice after low dose (FIG. 1A at 50 μg) and high dose (FIG. 1B at 500 μg) anti-TNF-α and anti-IL-23p19 antibody treatment alone or in combination. Each line represents the group mean with error bars for standard error (n=9 antibody treatment; n=5 PBS control; n=3 naïve control) and is shown as percent change from day −1 (dotted line). Some error bars are within the size of the symbol and are not depicted. Disease was induced by administration of anti-CD40 antibody (BioXCell, Cat. No. BE0016-2, Agonist CD40 Ab clone FGK4.55, lot#5345/0515).
Figure 1B:
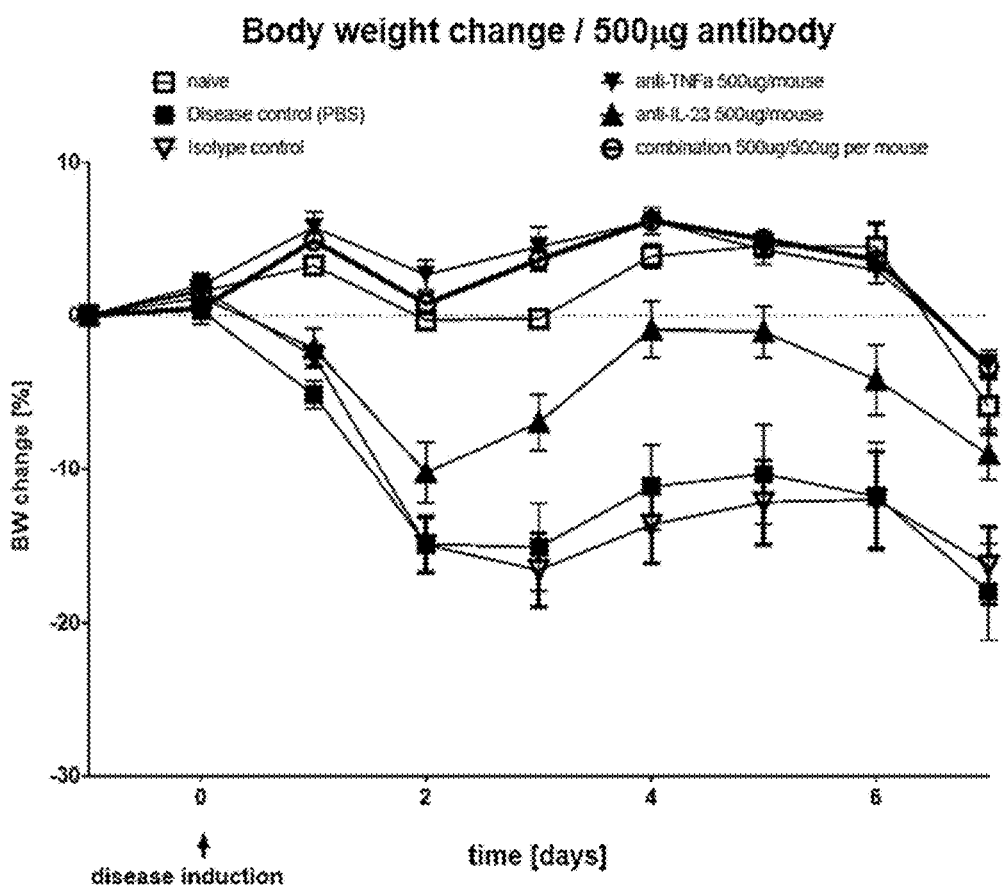

The data are shown in FIGS. 1A and 1B. Each line represents the group mean with error bars for standard error (n=9 antibody treatment; n=5 PBS control; n=3 naïve control) and is shown as percent change from day −1 (dotted line). Some error bars are within the size of the symbol and are not depicted. FIG. 1A shows the low dose (50 µg/mouse) and FIG. 1B shows the high dose antibody treatment (500 µg/mouse). Statistical significance of differences in body weight loss between antibody treatment groups and the isotype control group as comparator were analyzed by 2-way ANOVA with Dunnett's multiple comparison test and P-values for each time point are shown in the table. P-values indicating significance are highlighted in bold/italic. ELN: Immunopharmacology WC-2018-00034, Immunopharmacology WC-2018-00033.

The CD40 mAb-induced colitis model is characterized by a biphasic weight loss with an initial rapid body weight loss within 24-48 hours after the CD40-agonist antibody dosing followed by recovery and a second weight loss phase at days 5-7. Single treatment with anti-IL-23p19 antibody (0.5 mg and 0.05 mg) did not protect mice from the initial rapid body weight loss but promoted a faster recovery after day 2 with an overall dose-dependent partial protection against body weight loss during the second phase of the disease, as shown in FIGS. 1A and 1B.

In contrast, single treatments with anti-TNFα antibody (0.5 mg and 0.05 mg) completely protected mice from body weight loss during the entire duration of the study for both doses. Similar to the single antibody treatments against TNFα, the combination treatment resulted in complete protection from body weight loss at both doses (FIGS. 1A and 1B). No adverse effects were observed for the low-dose or high-dose combination treatments of anti-TNFα/IL-23p19.

At termination (day 7), colon histopathology scores were determined for low and high dose antibody treatment groups. The proximal colon sections were stained with H&E and examined for histopathological changes by a blinded pathologist using a severity score from 0-20 according to the following protocol.

For proximal colons, two (2) pieces were cut and embedded in paraffin. Sections (5 µm) were cut and stained with hematoxylin & eosin (H&E). The two colon segments from each animal were evaluated for histopathology individually and average values per animal were used in group analysis. For each H&E stained section, submucosal edema was quantitated by measuring the thickness from the muscularis mucosa to the internal border of the outer muscle layer in a nontangential area thought to best represent the severity of this change.

Figure 2A:
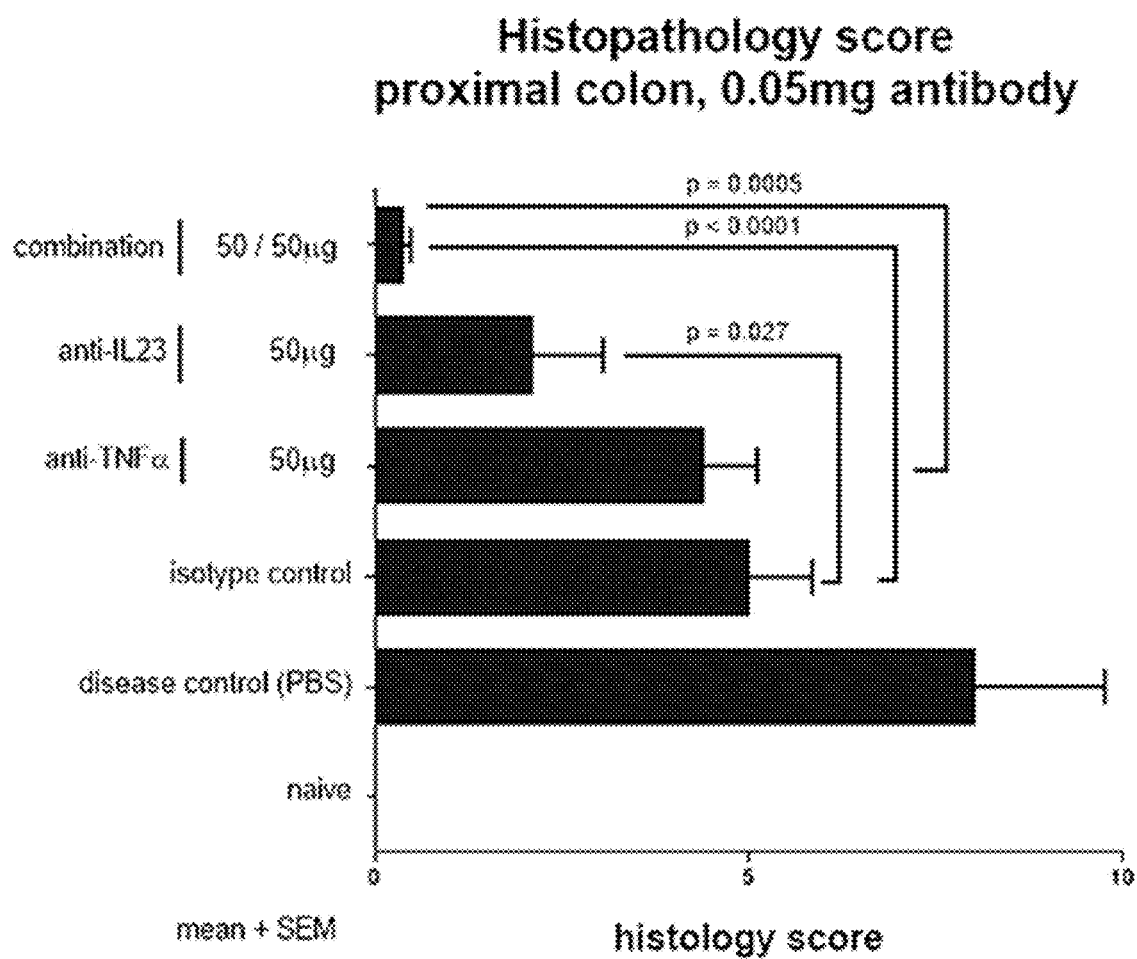
FIGS. 2A and 2B show the results of a histopathology study performed on the colon of mice treated with low dose (FIG. 2B at 50 μg/mouse) anti-TNF-α and/or anti-IL-23p19 antibody and high dose (FIG. 2B at 500 μg/mouse) anti-TNF-α and/or anti-IL-23p19 antibody, respectively. Disease was induced by administration of anti-CD40 antibody.
Figure 2B:
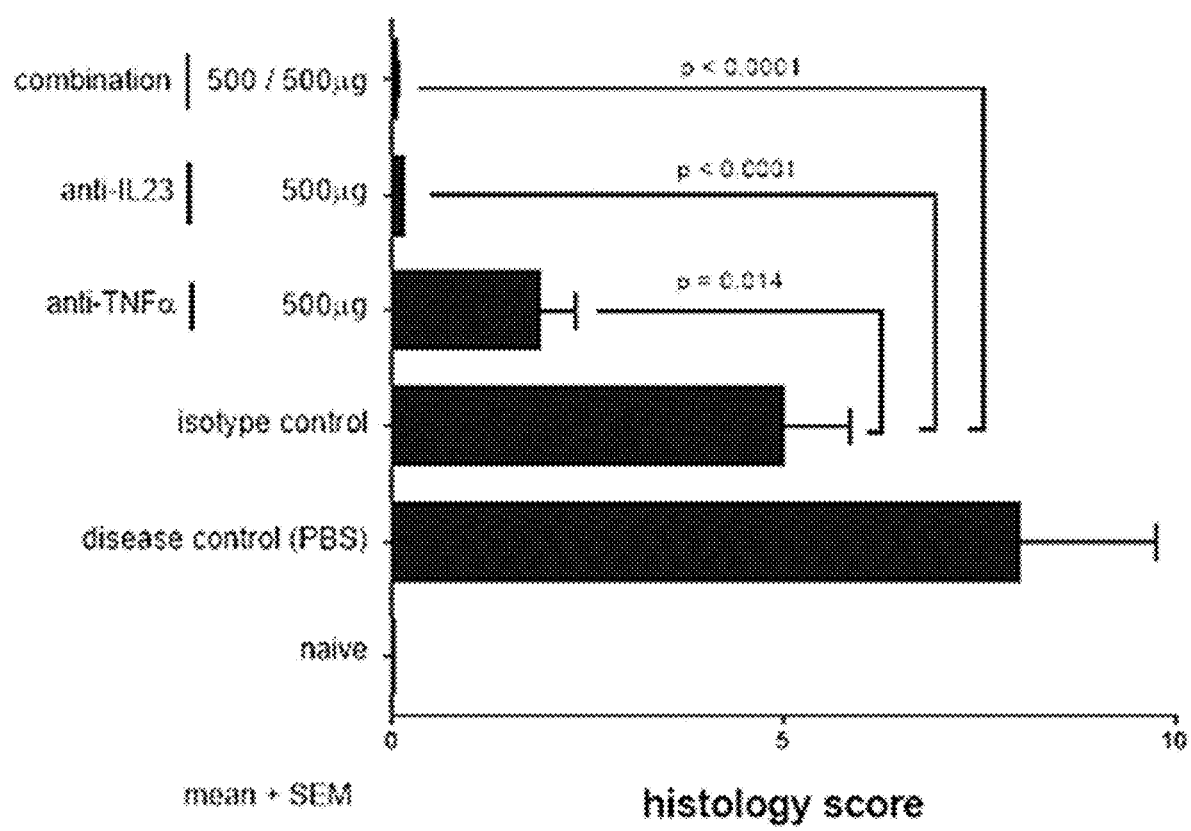

The Inflammation Score reflected the extent of macrophage, lymphocyte, and neutrophil (PMN) infiltrate. A severity score was assigned according to the following criteria:

0=Normal;
0.5=Very Minimal; one or two small foci, mononuclear inflammatory cells (MMIC) likely background mucosal lymphoid aggregates. However, if aggregates are Peyer's patches, then they are not scored as abnormal
1=Minimal, larger focal area with MNIC and neutrophils or minimal diffuse, no separation of glands, may be mostly in areas of submucosal edema or mesentery
2=Mild, diffuse mild, or multifocal affecting 11-25% of mucosa with minor focal or multifocal gland separation, no separation in most areas
3=Moderate, 26-50% of mucosa affected with minimal to mild focal or multifocal separation of glands by inflammatory cell infiltrate, milder in remaining areas of mucosa with some areas having no gland separation by inflammation
4=Marked, 51-75% of mucosa affected with mild to moderate separation of glands by inflammatory cell infiltrate, minimal to mild in remaining areas of mucosa but all glands have some separation by infiltrate
5=Severe, 76-100% of mucosa affected with moderate to marked areas of gland separation by inflammatory cell infiltrate, mild to moderate in remaining areas of mucosa A gland loss score was determined. Crypt epithelial and remaining gland epithelial loss is scored based on the approximate percent of the mucosa that was affected as follows:

0=None
0.5=Very Minimal, 1 or 2 small focal areas of gland loss or mucosal erosion
1=Minimal, 1-10% of the mucosa affected
2=Mild, 11-25% of the mucosa affected
3=Moderate, 26-50% of the mucosa affected
4=Marked, 51-75% of the mucosa affected
5=Severe, 76-100% of the mucosa affected An erosion score was determined. The loss of surface epithelium was scored based on the approximate percent of the mucosa that was affected as follows. This is generally associated with mucosal hemorrhage (reflective of the bleeding seen clinically and at necropsy):

0=None
0.5=Very Minimal, 1 or 2 small focal areas of gland loss or mucosal erosion
1=Minimal, 1-10% of the mucosa affected
2=Mild, 11-25% of the mucosa affected
3=Moderate, 26-50% of the mucosa affected
4=Marked, 51-75% of the mucosa affected
5=Severe, 76-100% of the mucosa affected A mucosal thickness and hyperplasia score was determined. Mucosal thickness was measured in a non-tangential area of the section that best represents the overall mucosal thickness. This parameter is indicative of gland elongation and mucosal hyperplasia. A hyperplasia score is derived from the measurement as follows:

0=≤200 µm=normal
0.5=201-250 µm=very minimal
1=251-350 µm=minimal
2=351-450 µm=mild
3=451-550 µm=moderate
4=551-650 µm=marked
5=>650 µm=severe The histopathology score is a sum of inflammation, gland loss, erosion, and hyperplasia scores. The range is from 0 to 20. The histopathology scores are shown in FIGS. 2A and 2B. In these figures, each bar represents the group mean with standard error. No histopathological findings were observed in naïve animals. FIG. 2A shows the results for low dose antibody (50 µg/mouse). FIG. 2B depicts the results for the high dose treatment group (500 µg/mouse). Differences between treatment groups and respective vehicle and isotype controls were analyzed for significance by One-way ANOVA and Sidak's multiple comparisons test. ELN: Immunopharmacology WC-2018-00034, Immunopharmacology WC-2018-00033.

In the proximal colon, treatment with isotype antibody (1000 µg/mouse) showed a trend toward reduced histopathology when compared to the disease control (PBS), but this did not reach statistical significance. Monotreatment with anti-TNFα antibody significantly reduced colon inflammation at the high dose (500 µg, FIG. 2B) when compared to isotype control, but not at the low dose (50 µg, FIG. 2A).

A single dose of anti-IL-23p19 antibody was highly efficacious at the high dose (500 µg, FIG. 2B), completely preventing the development of colitis. At the low dose (50 µg, FIG. 2A), the monotreatment significantly reduced histopathology compared to the isotype group but did not completely prevent colitis. The high dose combination of both antibodies (500 µg anti-TNFα+500 µg anti-IL-23p19/mouse, FIG. 2B) completely prevented colitis in the disease model, similar to the high dose of a single anti-IL-23p19 treatment.

The low dose combination treatment (50 µg anti-TNFα+ 50 µg anti-IL-23p19/mouse, FIG. 2A) was significantly more efficacious than the single anti-TNFα treatment and showed a trend for improved protection compared to monotreatment against IL-23p19, indicating potential superior efficacy for the combination.

Example 2: Anti-TNFα and Anti-IL-23p19 Treatments Impact Unique Genes in the Intestine The anti-TNFα and anti-IL-23p19 treatments show differential effects on readouts of systemic and local inflammation. In this example, an assessment was made whether the treatments of Example 1 above had distinct molecular effects on intestinal gene expression. To generate intestinal gene signatures, mRNA was isolated from the distal colon and submitted for microarray analysis.

For RNA extraction, tissue samples were thawed on ice and transferred into new tubes containing 900 µl of Qiazol (Qiagen) and one metal bead, followed by lysis using the TissueLyser II for disruption and homogenization of the tissue by running it 1 min at a frequency of 30 $S^{-1}$. 180 µl of chloroform were added to each sample, vortexed for 30 seconds, incubated for two minutes at room temperature, and centrifuged at 14,000 rpm for 15 minutes at 4° C. to separate the mix into an organic and an aqueous phase. 150 µl of the aqueous phase was used for RNA extraction using the RNeasy 96 well plate kit (Qiagen) including an on-column DNase digestion step all according to the manufacturer's protocols. Quality and quantity of the isolated RNA was determined by Nanodrop at a Nanodrop 8000 instrument (ThermoScientific) and by LabChip GX (DNA 5K/RNA/CZE Chip for use with GXTouch/GXII Touch HT) on Caliper instrument (Life Science) according to the manufacturer's protocols. For Caliper analysis the colon RNA aliquots were diluted 1:4 with molecular grade water.

The following exclusion criteria were used to determine which samples would be accepted for gene expression analysis by microarray. Nanodrop absorbance 260/280 (protein amount to nucleic acid) should be >1.8. Nanodrop absorbance 260/230 (salt amount to nucleic acid) should be close to 2. If nanodrop absorbance 260/230 was less than 1.5, then repurification was performed. Caliper RIN (RNA integrity number) should be 5-10. If less than 5, the accuracy of microarray analysis may be affected. RNA was shipped to BioStorage Technologies (Indianapolis, IN) for microarray analysis.

Differential gene expression analysis was performed by comparing the effect of anti-TNFα or anti-IL-23p19 to that of isotype control treatment. Because treatment with either the 50 ug anti-IL-23p19 or 500 ug anti-TNFα doses resulted in similar levels of reduction in histological inflammation (FIG. 2), the inventors chose these colonic gene expression signatures for further evaluation to mitigate potential confounding effects of differential cellular infiltrates gene expression.

Murine gene signatures for each treatment were evaluated for overlap and enrichment in biological pathways (Enrichr: http://amp.pharm.mssm.edu/Enrichr/). The overlap of the individual gene signatures generated from anti-TNFα or anti-IL-23p19 treatment was relatively small, with only 11% of genes shared between the signatures, and did not show any specific pathway enrichment. The gene signature for anti-TNFα treatment (267 genes, FDR<0.05, FC>1.2) was enriched in metabolic pathways and cytokine-cytokine receptor interactions while the anti-IL-23p19 gene signature (765 genes, FDR<0.05, FC>1.2) was enriched in circadian rhythm and p53 signaling.

Example 3: Anti-TNFα and Anti-IL-23p19 Single Antibody Treatments Impact Overlapping and Distinct Portions of Human IBD Networks In collaboration with the Mount Sinai School of Medicine (New York, NY), a predictive Bayesian network model was generated for integrating transcriptional and genetic data derived from intestinal biopsy samples from the Crohn's disease CERTIFI clinical trial (847 IBD biopsies, 28 non-IBD control biopsies; 7,796 gene nodes). (7, 10) This type of molecular integrative network provides a data-driven framework for studying gene-gene interactions in the context of disease. To translate the anti-TNFα and anti-IL-23p19 monotherapy gene signatures generated in murine colitis models to clinical disease, murine gene signatures were integrated with a human IBD patient gene network. As stated above, the 50 µg anti-IL-23p19 and 500 µg anti-TNFα doses were selected for evaluation based on their similar impact on histological inflammation.

To bridge the murine model data to the human IBD network, a 'humanized' version of each treatment gene signature was first generated by mapping the murine genes to their human orthologues (767 genes for anti-IL-23p19 and 274 genes for anti-TNFα). The murine genes were mapped to their human orthologs using NCBI HomoloGene (https://www.ncbi.nlm.nih.gov/homologene) database (Build 68, 04/14/2014). Each NCBI Gene Id for each murine gene profiled was matched to all corresponding human members of the same cluster of putative orthologs.

A database term was considered significant if its one-sided Fisher's Exact test E-value (Bonferroni corrected p-value) was less than 0.05.

A hypergeometric test was performed in Excel (HY-PGEOM.DIST function) to determine the enrichment of IBD GWAS loci genes in gene subnetworks. The gene list used for IBD GWAS loci enrichment was derived from Jostins et al, *Nature* 2012(8) and Liu et al, *Nature Genetics* 2015(9).

Using these humanized gene signatures, the enrichment analysis of the individual treatment signatures was extended to human pathways. The gene signature for anti-TNFα treatment was enriched in cellular response to stress and lipids, reactive oxygen species metabolism, inflammatory response genes and genes upregulated in patient biopsies. The anti-IL-23p19 treatment signature was enriched in cellular metabolism, regulation of proliferation and genes down-regulated in IBD patient biopsies.

Next, these humanized gene signatures were mapped onto the CERTIFI Bayesian network and generated treatment subnetworks using a web-based network visualization tool. Gene lists were generated as tab delimited text files and imported. Gene lists were applied to the T26 Pan-Intestine Bayesian Network (CERTIFI network(7)) and genes within the network and their first neighbors (genes within 1 step of a selected gene, either incoming or outgoing) were used to create a subnetwork.

These treatment subnetworks contain genes modified by anti-TNFα or anti-IL-23p19 treatment in the mouse model that are reflected in human IBD tissue and their immediate neighboring genes in the network. Thus, enrichment analysis of these subnetworks may provide insights into the biological pathways targeted by each therapeutic in the context of human disease tissue.

Figure 3A:
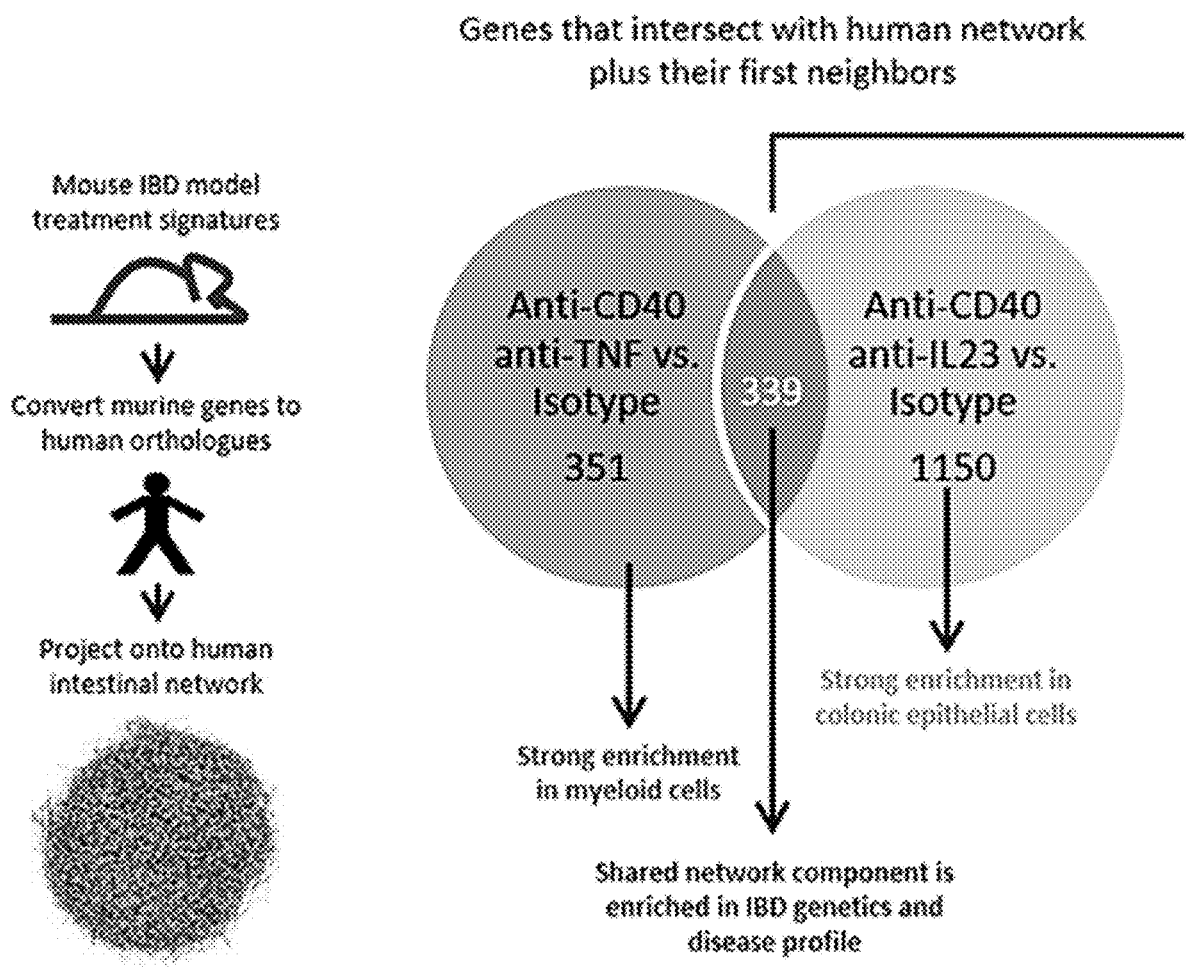
FIG. 3A shows humanized treatment signatures of anti-TNFα or anti-IL-23p19 monotherapy from the anti-CD40 model of murine colitis projected onto the Crohn's Evaluation of Response to Ustekinumab Anti-Interleukin-12/23 for Induction (CERTIFI) human IBD gene expression network.
Figure 3B:
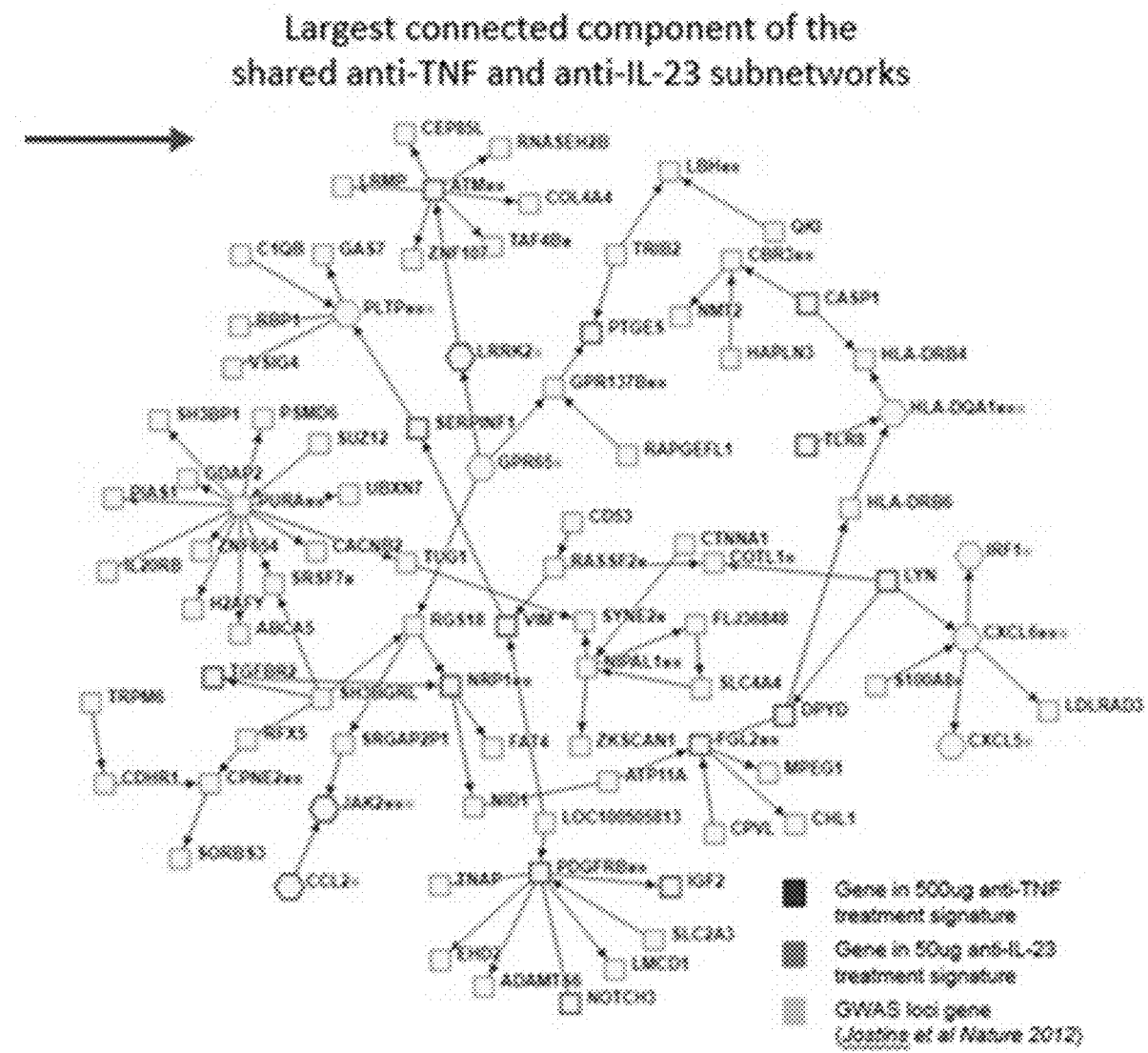
FIG. 3B illustrates the largest connected component of the shared anti-TNFα and anti-IL-23p19 subnetworks.

FIGS. 3A and 3B show humanized treatment signatures of anti-TNFα or anti-IL-23p19 monotherapy from the anti-CD40 model of murine colitis projected onto the CERTIFI human IBD gene expression network. First neighbors of genes within the human IBD network were extracted to produce treatment subnetworks. The overlap between genes present in the anti-TNFα and anti-IL-23p19 subnetworks is illustrated by the Venn diagram in the center. The largest connected component of the shared subnetwork of anti-TNFα and anti-IL-23p19 is shown in FIG. 3B.

While no specific biology was enriched in analysis of the intersection of the original gene signatures, focused analysis of the largest connected component of the network neighborhood shared by both anti-TNFα and anti-IL-23p19 revealed enrichment in genes dysregulated in IBD patient tissues as well as IBD GWAS loci genes, suggesting that efficacy of these distinct mechanisms could be mediated, in part, through targeting of shared core inflammatory pathways. The intersection of these two therapeutic subnetworks was significantly enriched in IBD GWAS loci genes ($p=0.001$) and genes up-regulated in IBD patient tissue (multiple signatures; top signature E-value 7.25e-27) (FIG. 3). The unique portion of the anti-TNF subnetwork was highly enriched in neutrophil and CD11b$^+$ macrophage gene signatures (E-values 8.28e-10 and 2.41e-06, respectively) while the unique portion of the anti-IL-23p19 subnetwork was highly enriched for colonic epithelial cells (E-value 1.27e-32), consistent with the role of IL-23 in promoting the expression of cytokines, such as IL-17A and IL-22, that impact epithelial cell biology. The relative enrichment in myeloid cells and epithelial cells in the anti-TNFα and anti-IL-23p19 unique regions of the network, respectively, raised an additional hypothesis that combination therapy with both antibodies could provide benefit by targeting distinct cell types involved in IBD pathogenesis. Remarkably similar results were observed when performing the same type of network analyses using gene signatures derived from anti-TNFα or anti-IL-23p19 therapeutic treatments in an orthogonal murine model of intestinal inflammation, the T cell transfer model of colitis (ELN: jperrigo-2016-00002). Taken together, these network analyses suggest that the anti-TNFα and anti-IL-23p19 mechanisms of action are distinct, but converge on the molecular drivers of intestinal inflammation.

Example 4: Expanded Dose Range Analysis for Anti-TNFα and Anti-IL-23p19 Antibody Treatments in Anti-CD40 Antibody Induced Colitis (Study 2)

To enable further evaluation of the effects of combination therapy, an extended dose response study in the CD40-antibody induced colitis model was conducted to determine the minimal effective dose for each antibody. One day before disease induction with anti-CD40 agonistic antibody, female RAG2$^{-/-}$ mice were dosed ip with anti-IL-23p19 antibody (CNTO 3723 at 50, 15, 5, 1.5, 0.5, 0.15 µg/mouse), anti-TNFα antibody (CNTO 5048 at 150 and 15 µg/mouse) or isotype control (50 µg/mouse). The protocol is summarized in Table 2 below.

TABLE 2

Evaluation of lower dose range for single antibody
against TNFα and IL-23p19 in the CD40 colitis
model/Study 2, ELN: Immunopharmacology WC-2016-00038

| Test article | Route | Dose | Number of animals |
|---|---|---|---|
| Naïve | | None | 5 |
| Vehicle (PBS) | ip | 10 ml/kg, day −1 | 5 |
| CNTO 6601 | ip | 50 µg/mouse, day −1 | 10 |
| CNTO 3723 | ip | 50 µg/mouse, day −1 | 10 |
| CNTO 3723 | ip | 15 µg/mouse, day −1 | 10 |
| CNTO 3723 | ip | 5 µg/mouse, day −1 | 10 |
| CNTO 3723 | ip | 1.5 µg/mouse, day −1 | 10 |
| CNTO 3723 | ip | 0.5 µg/mouse, day −1 | 10 |
| CNTO 3723 | ip | 0.15 µg/mouse, day −1 | 10 |
| CNTO 5048 | ip | 150 µg/mouse, day −1 | 10 |
| CNTO 5048 | ip | 15 µg/mouse, day −1 | 10 |

Body weight was monitored from day −1, when the mice were injected with antibody or PBS, until termination on day 7. The data is shown in FIGS. 4A-4D. Each line represents the group mean with standard error (n=10 antibody treatment; n=5 PBS control; n=3 naïve control) and is shown as percent change from day −1 (dotted line). The significance of differences to the isotype control group was analyzed for each treatment group by 2-way ANOVA with Dunnett's multiple comparison test and the resulting p-values for each study day are shown in the table. P-values indicating significant differences are highlighted in bold/italic. ELN: Immunopharmacology WC-2016-00038, Immunopharmacology WC-2018-00033.

Figure 4A:
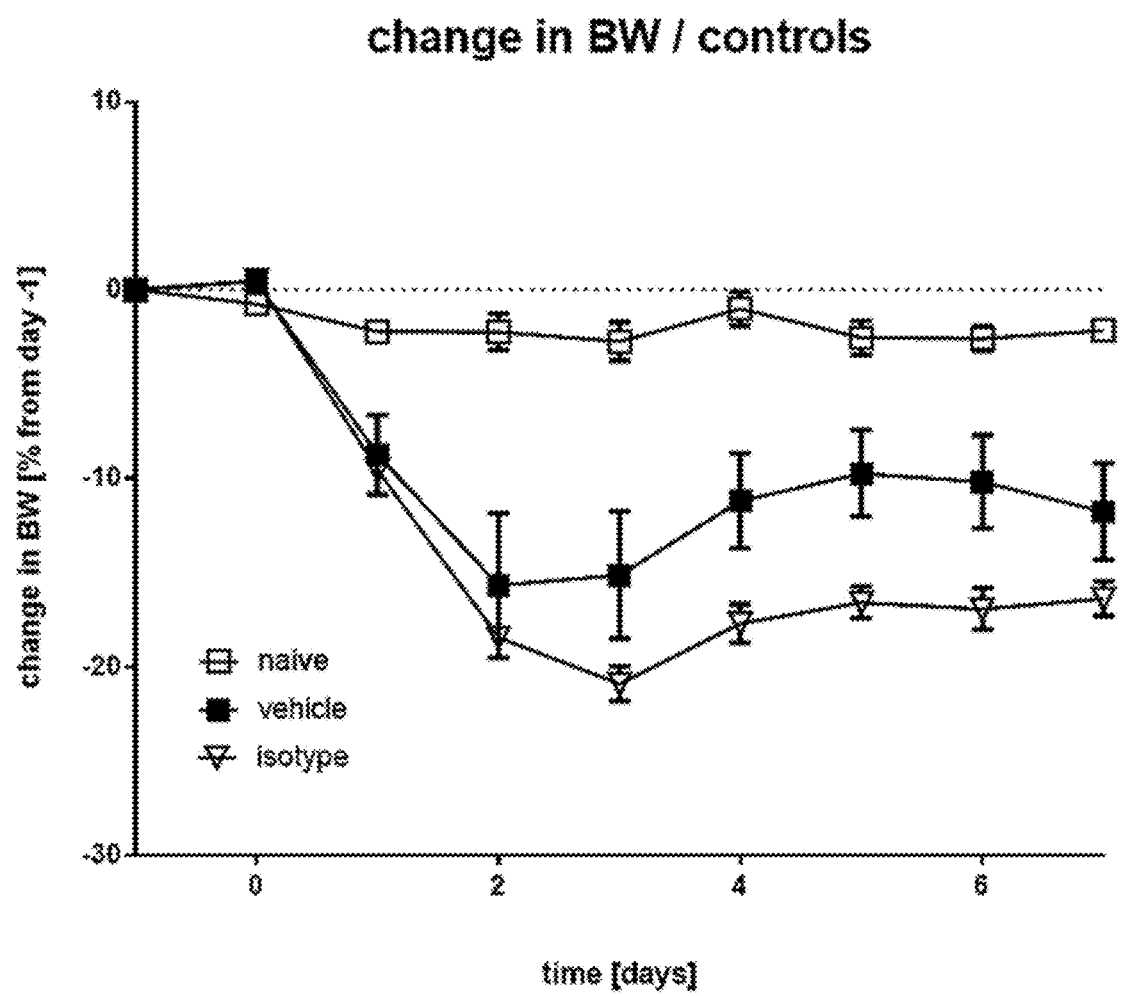
Figure 4B:
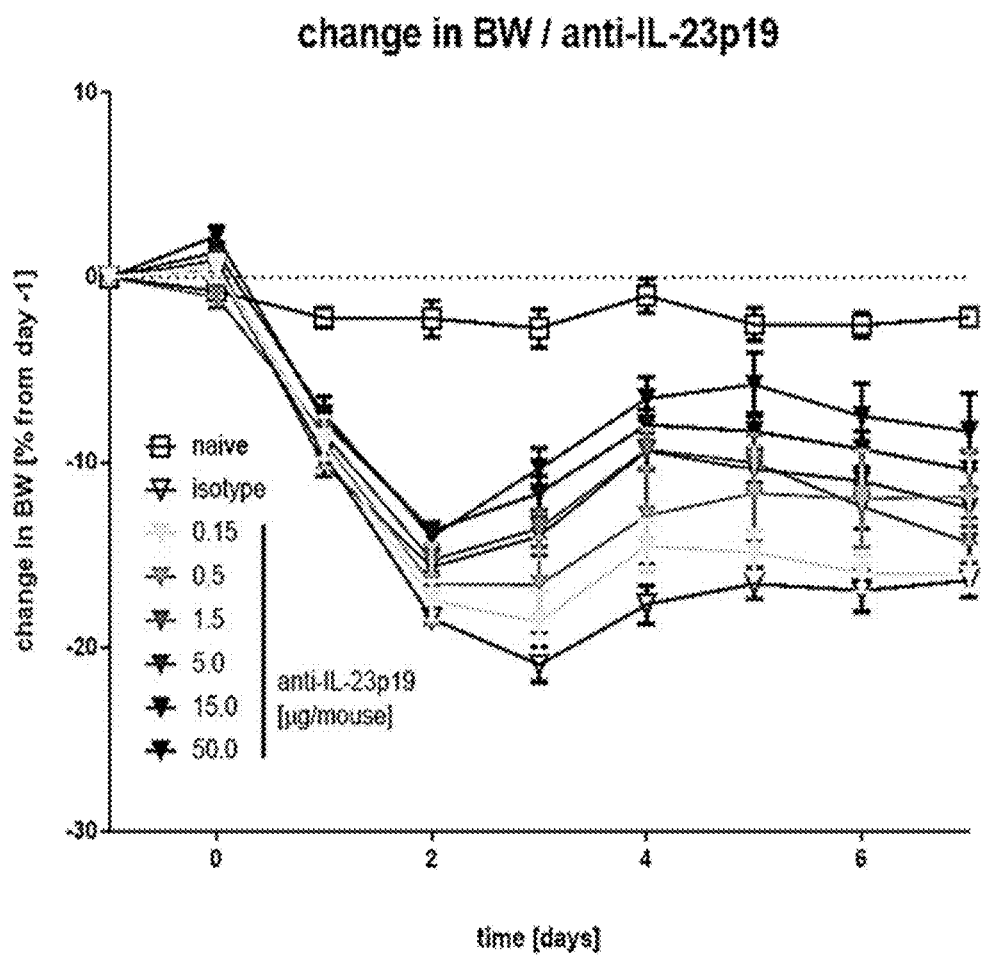
Figure 4C:
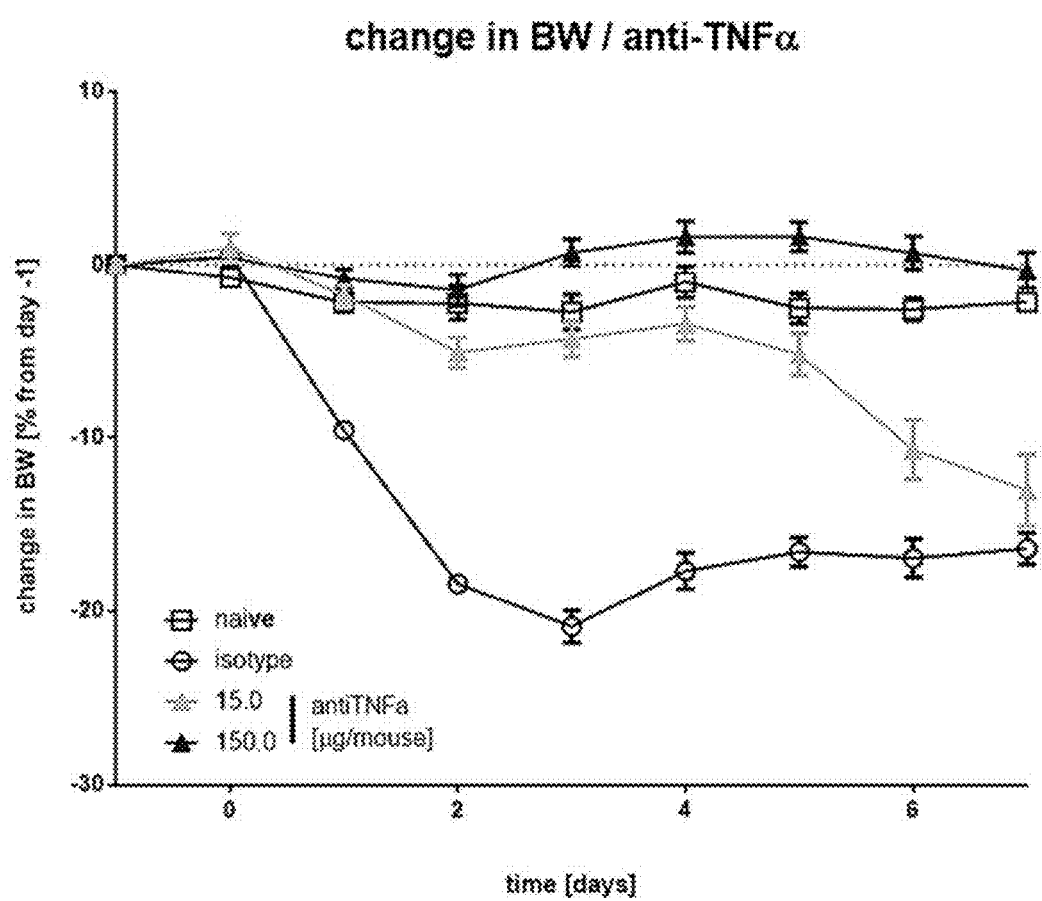

A partially significant increase in body weight loss was observed in the isotype control group when compared to vehicle control. Treatment with anti-IL-23p19 antibody showed partial dose-dependent protection against body weight loss starting at day 2 at the two highest doses (15, 50 µg/mouse). Only at the lowest dose of anti-IL-23p19 antibody (0.15 µg/mouse), no protection from body weight loss was observed, as shown in FIG. 4B. Treatment with anti-TNFα antibody completely protected against the body weight loss at the higher dose (150 µg/mouse), but at the lower dose (15 µg/mouse), only a partial protection was noted. See FIG. 4C.

A histopathology analysis of the proximal colon was performed as follows, after single antibody treatments for dose range determination. At termination (day 7), proximal colon sections were removed, flushed, fixed and then stained with H&E. The stained samples were examined for histopathological changes by a blinded pathologist using a severity score from 0-20 using the protocol in Example 1 above. The data is shown in FIGS. 5A-C. No histopathological findings were observed in naïve animals. Differences between antibody treatment groups and respective isotype controls were analyzed for significance by a one-way ANOVA-Sidak's multiple comparisons test. The line depicts the group median. ELN: Immunopharmacology WC-2016-00038, Immunopharmacology WC-2018-00033.

Colon histopathology demonstrated dose-dependent protection from colitis by anti-IL-23p19 antibody treatment, as shown in FIG. 5B. At the 50 µg/mouse dose, anti-IL-23p19 antibody treatment provided near complete protection. Partial protection was detected at antibody doses of 15 µg and 5 µg, and no protection was observed at doses of 1.5 µg and lower. In contrast, no significant treatment effects were detected for the two dose levels of anti-TNFα antibody (150, 15 µg) on colon histopathology. See FIG. 5C. These results confirm that blocking IL-23 signaling is highly efficacious against colitis in this model. Inhibition of TNFα, although efficacious against systemic inflammation (as measured by the amelioration of body weight loss), only offers moderate protection against colitis in this model.

Example 5: Determination of Anti-Inflammatory Activity of a Combination of Fixed Dose Anti-TNFα Antibody and Varying Doses of Anti-IL-23p19 Antibody in the CD40 Colitis Model (Study 3)

A combination study was performed in the CD40 colitis model using a fixed dose of anti-TNFα antibody (500 µg/mouse) in combination with varying doses of anti-IL-23p19 antibody (1.5, 5, 25 µg/mouse). Corresponding single doses of anti-IL-23p19 antibody were also included. The protocol is summarized in Table 3 below.

TABLE 3

Evaluation of single high dose TNFα antibody
treatment and low doses of IL-23p19 alone versus
in combination in the CD40 colitis model/Study
3, ELN: Immunopharmacology WC-2016-00066

| Test article | Route | Dose | Number of animals |
|---|---|---|---|
| Naïve | | None | 5 |
| Vehicle (PBS) | ip | 10 ml/kg, day −1 | 10 |
| CNTO 6601 | ip | 525 µg/mouse, day −1 | 10 |
| CNTO 5048 | ip | 500 µg/mouse, day −1 | 10 |
| CNTO 3723 | ip | 1.5 µg/mouse, day −1 | 10 |
| CNTO 3723 | ip | 5 µg/mouse, day −1 | 10 |
| CNTO 3723 | ip | 25 µg/mouse, day −1 | 10 |
| CNTO 3723 + CNTO 5048 | ip | 1.5 + 500 µg/mouse, day −1 | 10 |
| CNTO 3723 + CNTO 5048 | ip | 5 + 500 µg/mouse, day −1 | 10 |
| CNTO 3723 + CNTO 5048 | ip | 25 + 500 µg/mouse, day −1 | 10 |

An assay of body weight loss after single and combination treatment with high dose anti-TNFα and low dose anti-IL-23p19 antibody was undertaken as follows.

Body weight was monitored from day −1, when the mice were injected with antibody (isotype control: 525 µg; anti-TNFα: 500 µg; anti-IL-23p19: 25, 5, 1.5 µg) or PBS (10 ml/kg), until termination on day 7. The data are shown in FIG. 6. Each line represents the group mean (n=10 antibody treatment and vehicle; n=5 naïve control) and is shown as percent change from day −1 (dotted line). The significance of differences to isotype control group was analyzed by for each treatment group by 2-way ANOVA with Dunnett's multiple comparison test. P-values for each study day are shown in the table and highlighted in bold/italic if they indicate significance. ELN: Immunopharmacology WC-2016-00066, Immunopharmacology WC-2018-00033.

Consistent with previous studies, high dose anti-TNFα antibody completely protected against body weight loss, as shown in FIG. 6B. In contrast, monotreatment with anti-IL-23p19 antibody, at all doses, provided partial protection from body weight loss, particularly during the late phase of anti-CD40 antibody induced disease. See FIG. 6C. The combination of anti-TNFα antibody and anti-IL-23p19 antibody provided no additional detectable benefit on inhibition of weight loss as compared to the monotherapy (FIG. 6D). Without wishing to be bound by theory, this effect may be due to the robust efficacy of monotherapy of anti-TNFα antibody on this parameter.

Histopathology analysis for proximal colon was performed after single and combination antibody treatments with high dose anti-TNFα and low dose anti-IL-23p19 antibody. At termination (day 7), proximal colon tissue samples were removed, flushed, fixed and then stained with H&E and examined for histopathological changes by a blinded pathologist using a severity score from 0-20, as described in Example 1 above. The data are shown in FIGS. 7A-7C. No histopathological findings were observed in naïve animals. Differences between antibody treatment groups and respective isotype controls were analyzed for significance by One-way ANOVA-Sidak's multiple comparisons test. The line depicts the group median. ELN: Immunopharmacology WC-2016-00066, Immunopharmacology WC-2018-00033.

As shown in FIGS. 7A-7C, anti-TNFα antibody (500 μg/mouse) did not offer significant protection against colon histopathology as compared to the isotype control. The anti-IL-23p19 antibody (1.5, 5 and 25 μg/mouse) treatment demonstrated dose-dependent protection from colitis, with no protection seen at the lowest dose (1.5 μg/mouse). Partial protection from colitis was observed with the two higher doses (5 and 25 μg/mouse).

Due to the low amount of antibody used for anti-IL-23p19, the statistical significance for the single anti-IL23p19 treatments were calculated against the vehicle control, but not against the high dose (525 μg/mouse) isotype control. All combination treatments showed significant protection from colon inflammation compared with single anti-TNFα treatment. See FIGS. 7A-7C. Of note, in the case of the lowest combination dose evaluated (500 μg/mouse TNFα+1.5 μg/mouse anti-IL-23p19), both monotherapy treatments failed to provide any protection from colonic histopathology but showed significant improvement in histopathology when given in combination. See FIG. 7A. It was unexpected that the relatively small amount of anti-IL-23p19 antibody in combination with anti-TNFα antibody (e.g., as a ratio of 1:333 (w/w)) provided such a substantial improvement in colon histopathology. It was also unexpected that the colon histopathology score observed in the group receiving 500 μg/mouse TNFα+1.5 μg/mouse anti-IL-23p19 is not statistically different from that observed in the isotype control group. These results indicate that a combination treatment of fixed high dose TNFα mAb and a sub-optimal low dose of IL-23p19 provides superior protection compared to the monotherapies against the two cytokines.

Example 5: Combination Anti-TNFα and Anti-IL-23p19 Treatment Impacts a Unique Subnetwork Enriched in Wound Healing Pathways The molecular impact of combination therapy with anti-TNFα and anti-IL-23p19 antibodies versus monotherapy was determined. Humanized colonic gene expression signatures of anti-TNFα (500 μg) or high dose anti-IL-23p19 (25 μg) monotherapies were intersected with a gene expression signature from the combination therapy (500 μg anti-TNFα/1.5 μg anti-IL-23p19) to determine whether the molecular response to anti-TNFα and low dose anti-IL-23p19 antibody combination treatment was additive or unique compared with either therapy alone.

The 25 μg dose of anti-IL-23p19 treatment was selected for comparison so as to compare the effect of combination treatment of anti-TNFα with a sub-optimal dose of anti-IL-23p19 to that of a monotherapy dose of anti-IL-23p19 that had efficacy in the model.

As in Study 1, humanized colonic gene signatures were generated for each single and combination therapy treatment group for evaluating signature overlap, generating treatment subnetworks and performing enrichment analyses. The data is shown in FIG. 8, left panel. Two hundred twenty genes were found to be uniquely differentially-regulated after combination therapy (500 μg anti-TNFα/1.5 μg anti-IL-23p19) versus either monotherapy (500 μg anti-TNFα or 25 μg anti-IL-23p19). These genes were projected onto the CERTIFI intestinal Bayesian network. The largest connected component of the resulting induced 1-step subnetwork was subjected to enrichment analysis, with results shown in FIG. 8, right panel. A network analysis of these 220 genes identified a unique subnetwork (shown in FIG. 8) for the combination treatment that was enriched in fibroblasts and extracellular matrix organization, cell types and pathways involved in wound repair and mucosal healing. Thus, anti-TNFα and anti-IL-23p19 therapies may provide added benefit when used in combination by targeting both shared and unique disease relevant pathways.

Example 6: Clinical Study of Anti-TNFα and Anti-IL-23p19 Treatment in UC

A Phase 2a Randomized, Double-blind, Active-controlled, Parallel-group, Multicenter, Proof-of-concept Clinical Study to Evaluate the Efficacy and Safety of Combination Therapy With Guselkumab and Golimumab in Participants With Moderately to Severely Active Ulcerative Colitis Guselkumab (CNTO 1959 or TREMFYA®) is a fully human immunoglobulin G1 lambda monoclonal antibody (mAb) that binds to the p19 subunit of human interleukin (IL)-23 with high specificity and affinity. The binding of guselkumab to IL-23 blocks the binding of extracellular IL-23 to the cell surface IL-23 receptor, inhibiting IL-23-specific intracellular signaling and subsequent activation and cytokine production. Guselkumab is currently approved in the United States, European Union, Canada, and several other countries for the treatment of moderate to severe plaque psoriasis. In addition, guselkumab is also being evaluated in psoriatic arthritis (PsA) and Crohn's disease globally.

Golimumab (CNTO 148 or SIMPONI®) is a fully human anti-tumor necrosis factor alpha (TNFα) mAb that binds to TNFα with high affinity. This interaction prevents the binding of TNFα to its receptors, thereby inhibiting the biological activity of TNFα. Golimumab is approved for treatment of moderately to severely active ulcerative colitis (UC) in over 90 countries worldwide. Additionally, golimumab is approved for 1 or more of the following indications around the world: rheumatoid arthritis (RA), PsA, ankylosing spondylitis (AS), nonradiographic axial spondyloarthritis (nr-Axial SpA), and polyarticular juvenile idiopathic arthritis (pJIA).

Objectives and Endpoints

This study will consist of 2 distinct phases: a 12-week combination comparison phase followed by a 26-week monotherapy phase.

Objectives

Primary Objectives

Combination Comparison Phase

To evaluate the clinical efficacy of combination therapy with guselkumab and golimumab in participants with moderately to severely active UC.

To evaluate the safety of combination therapy with guselkumab and golimumab in participants with moderately to severely active UC.

Secondary Objectives
Combination Comparison Phase
    To evaluate the effect of combination therapy with guselkumab and golimumab on endoscopic improvement.
    To evaluate the impact of combination therapy with guselkumab and golimumab on disease-specific health-related quality of life (HRQOL), including fatigue.
    To evaluate the efficacy of combination therapy with guselkumab and golimumab by negative response signature status at baseline.
    To evaluate the pharmacokinetics (PK), immunogenicity, and pharmacodynamics (PD) of combination therapy with guselkumab and golimumab, including changes in C-reactive protein (CRP), fecal calprotectin, and other PD biomarkers.
Monotherapy Phase
    To evaluate the clinical efficacy of combination therapy followed by guselkumab monotherapy.
    To evaluate the safety of combination therapy followed by guselkumab monotherapy.
    To evaluate the effect of combination therapy followed by guselkumab monotherapy on endoscopic improvement.
    To evaluate the impact of combination therapy followed by guselkumab monotherapy on disease-specific HRQOL, including fatigue.
    To evaluate the efficacy of combination therapy followed by guselkumab monotherapy by negative response signature status at baseline.
    To evaluate the PK, immunogenicity, and PD of combination therapy followed by guselkumab monotherapy, including changes in CRP, fecal calprotectin, and other PD biomarkers.
Exploratory Objectives
    To explore the effect of combination therapy on patient-reported outcome (PRO) instruments (e.g., Bristol Stool Form Scale [BSFS] and Patient's Global Impression of Change [PGIC] of Severity of UC).
Endpoints
Primary Endpoint
    Clinical response at Week 12, defined as a decrease from baseline in the Mayo score≥30% and ≥3 points with either a decrease in rectal bleeding subscore (RBS)≥1 or a RBS of 0 or 1.
Major Secondary Endpoint
    Clinical remission at Week 12, defined as a Mayo score≤2 with no individual subscore>1. Note: Other remission definitions may be considered and will be fully described in the Statistical Analysis Plan (SAP).
Hypothesis
    Combination therapy with guselkumab and golimumab will result in a rate of clinical response at Week 12 that is superior to both monotherapy arms.
Overall Design
    This is a Phase 2a, randomized, double-blind, active-controlled, parallel-group, multicenter, interventional proof-of-concept (POC) clinical study designed to evaluate the efficacy and safety of combination therapy with guselkumab and golimumab in adults with moderately to severely active UC. The target population is men or women 18 to 65 years old with moderately to severely active UC, as defined by a Mayo score of 6 to 12, inclusive, at baseline, including an endoscopy subscore≥2 as obtained during the central review of the video endoscopy. Participants must be naïve to TNF antagonists and have failed or not tolerated conventional therapy with oral or intravenous (IV) corticosteroids or immunomodulators (6-mercaptopurine [6-MP] or azathioprine [AZA]).

Immunomodulators (6-MP, AZA, and methotrexate [MTX]) must be discontinued for at least 2 weeks before the first dose of study intervention. For participants who are receiving oral corticosteroids at baseline, the investigator must begin tapering the daily dose of corticosteroids at Week 6. All participants will be evaluated for clinical worsening of UC throughout the study. In general, doses of concomitant therapies for UC should remain stable through Week 38 (except for oral corticosteroid tapering beginning at Week 6), and concomitant therapies for UC should not be initiated unless considered medically necessary by the investigator. Initiation of prohibited therapies will result in discontinuation of study intervention.

Endoscopy with central read is planned for screening/baseline, Week 12, and Week 38. Consenting participants will have an additional endoscopy at Week 4, which will also be assessed by a central reader. Efficacy, PK and PD parameters, biomarkers, and safety will be assessed according to the Schedule of Activities (SoA). A pharmacogenomic blood sample will be collected from participants who consent to this component of the protocol (where local regulations permit). Participation in pharmacogenomic research is optional.

An interim analysis is planned to inform future clinical development. Database locks (DBLs) are planned at Weeks 12 and 38, and a final DBL is planned after all participants complete the safety follow-up visit. An independent Data Monitoring Committee (DMC) will be commissioned for this study.

Number of Participants
    A target of 210 participants will be enrolled in this study with 70 participants planned per intervention group.
Intervention Groups and Duration
    This study will consist of 2 distinct phases: a 12-week combination comparison phase followed by a 26-week monotherapy phase. At Week 0, a target of 210 participants will be randomized in a 1:1:1 ratio to either combination therapy with guselkumab and golimumab, guselkumab monotherapy, or golimumab monotherapy, stratified by the concomitant use of corticosteroids at baseline (Y/N). Participants randomized to combination therapy will receive guselkumab monotherapy after Week 12. Participants randomized to a monotherapy group will continue on their originally randomized monotherapy after Week 12. The combination therapy arm will employ the same dose regimens of guselkumab and golimumab being used in the respective monotherapy intervention groups to facilitate scientific interpretation of the results. The following is a description of the 3 intervention groups:
    Combination therapy: guselkumab 200 mg IV and golimumab 200 mg subcutaneous (SC) at Week 0; golimumab 100 mg SC at Weeks 2, 6, and 10; guselkumab 200 mg IV at Weeks 4 and 8 followed by guselkumab 100 mg SC q8w
    Guselkumab monotherapy: guselkumab 200 mg IV at Weeks 0, 4, and 8 followed by guselkumab 100 mg SC q8w
    Golimumab monotherapy: golimumab 200 mg SC injection at Week 0, followed by golimumab 100 mg at Week 2 and then golimumab 100 mg every 4 weeks (q4w)
In addition, placebo administrations (IV or SC) will be given, as appropriate, to maintain the blind throughout the duration of the study.
    Overall participant duration will be up to 58 weeks total (screening: up to 8 weeks; treatment duration: 38 weeks [12 weeks for the combination comparison phase; 26 weeks for the monotherapy phase]; safety follow-up: approximately 16 weeks after the last administration of study intervention at Week 34). The end of the study will be defined as when the last participant completes his or her final safety follow-up visit.

Efficacy Evaluations (Endpoints)
Efficacy evaluations will include the following:
  Mayo score and Partial Mayo score
  Ulcerative Colitis Endoscopic Index of Severity (UCEIS)
  Inflammatory PD markers including CRP and fecal calprotectin
  Patient-reported outcome measures to assess HRQOL outcomes and fatigue (ie, Inflammatory Bowel Disease Questionnaire [IBDQ], Patient-Reported Outcomes Measurement Information System [PROMIS]-29, and PROMIS Fatigue 7-item Short Form [7a])
  Exploratory patient-reported symptom measures including BSFS and PGIC of Severity of UC Other Efficacy Evaluations (Endpoints)
Efficacy evaluations will include the following:
Combination Comparison Phase (i.e., Through Week 12)
  Endoscopic healing at Week 12 (Mayo endoscopic subscore of 0 or 1).
  Normalization of endoscopic appearance of the mucosa (Mayo endoscopic subscore of 0).
  Histologic healing at Week 12.
  Mucosal healing at Week 12 (Composite Mayo endoscopic healing and histologic healing).
  Change from baseline in the total score of the Inflammatory Bowel Disease Questionnaire (IBDQ) at Weeks 6 and 12.
  A >20-point improvement in the IBDQ score at Weeks 6 and 12.
  Change from baseline in the 7 domains and the abdominal pain numerical rating scale of Patient-Reported Outcomes Measurement Information System (PROMIS)-29 at Weeks 6 and 12.
  Fatigue response at Weeks 6 and 12 (based on the PROMIS Fatigue Short Form 7a; to be defined in the SAP).
  Clinical response, clinical remission, and endoscopic healing at Week 12 by negative response signature status at baseline.
  Change from baseline in the Mayo score at Week 12.
  Change from baseline in the partial Mayo score through Week 12.
  Change from baseline in CRP through Week 12.
  Change from baseline in fecal calprotectin concentration through Week 12.
  Normalization of CRP concentration at Week 12 among participants with abnormal CRP concentration at baseline.
  Normalization of fecal calprotectin concentration at Week 12 among participants with abnormal fecal calprotectin concentration at baseline.
  Ulcerative Colitis Endoscopic Index of Severity (UCEIS) score at Weeks 0 and 12 by the level of Mayo endoscopy score at the corresponding visit.
  Change from baseline in the UCEIS score at Week 12.
  UCEIS score≤4 at Week 12.
  UC-related emergency department visits, hospitalizations, and surgeries through Week 12.
Monotherapy Phase (i.e., after Week 12)
  Clinical remission at Week 38.
  Clinical response at Week 38.
  Maintenance of clinical response at Week 38 among participants who achieved clinical response at Week 12.
  Endoscopic healing at Week 38.
  Normalization of endoscopic appearance of the mucosa at Week 38.
  Histologic healing at Week 38.
  Mucosal healing at Week 38.
  Clinical remission and not receiving concomitant corticosteroids at Week 38.
  Maintenance of clinical remission at Week 38 among participants who achieved clinical remission at Week 12.
  Change from baseline in the total score of the IBDQ at Weeks 24 and 38.
  A >20-point improvement in the IBDQ score at Weeks 24 and 38.
  Change from baseline in the 7 domains and the abdominal pain numerical rating scale of PROMIS-29 at Weeks 24 and 38.
  Fatigue response at Weeks 24 and 38.
  Clinical response, clinical remission, and endoscopic healing at Week 38 by negative response signature status at baseline.
  Change from baseline in the Mayo score at Week 38.
  Change from baseline in the partial Mayo score through Week 38.
  Change from baseline in CRP through Week 38.
  Change from baseline in fecal calprotectin concentration through Week 38.
  Normalization of CRP concentration at Week 38 among participants with abnormal CRP concentration at baseline.
  Normalization of fecal calprotectin concentration at Week 38 among participants with abnormal fecal calprotectin concentration at baseline.
  UCEIS score at Week 38 by the level of Mayo endoscopy score at Week 38.
  Change from baseline in the UCEIS score at Week 38.
  UCEIS score≤4 at Week 38.
  UC-related emergency department visits, hospitalizations, and surgeries through Week 38.
Exploratory Endpoints
  BSFS score over time.
  The distribution of the PGIC of Severity of UC over time.
Pharmacokinetic and Immunogenicity Evaluations
  Serum samples will be analyzed to determine concentrations of guselkumab and golimumab and detection of anti-guselkumab and anti-golimumab antibodies, respectively, using validated, specific, and sensitive immunoassay methods by or under the supervision of the sponsor.
Pharmacodynamic and Biomarker Evaluations
  Biomarker assessments will be made to examine the biologic response to treatment and to identify biomarkers that are relevant to guselkumab and/or golimumab in the treatment of UC. Assessments will include the evaluation of relevant biomarkers in serum, stool, whole blood, and mucosal biopsy samples (RNA [ribonucleic acid], histology, and single cell isolation).
Pharmacogenomic (DNA) Evaluations
  A pharmacogenomic whole blood sample of approximately 5 mL will be collected (where local regulations permit) for genetic analyses as specified in the SoA. Only participants who sign the consent form to participate in the genetic assessment will have whole blood deoxyribonucleic acid (DNA) samples collected. Participation in the pharmacogenomic sub-study is optional.
Safety Evaluations
  Safety evaluations conducted at each study visit will include the assessment of adverse events (AEs, at the visit and those occurring between evaluation visits), a tuberculosis (TB) evaluation and other infection assessment, clinical laboratory blood tests (hematology and chemistry), vital signs, suicidality assessment, concomitant medication review, observations for injection-site reactions, AEs temporally associated with infusion, and/or hypersensitivity reactions.

Statistical Methods

Sample Size Determination

A sample size of 210 participants (70 per intervention group) was determined by the power to detect a significant difference in the proportion of participants in clinical response at Week 12 (primary endpoint) between the combination therapy and both monotherapies using a 1-sided chi-square test with 0.1 significance level for each comparison. The study is sized such that the combination therapy has approximately 80% power based on simulations to achieve both comparisons to monotherapy for the primary endpoint. The proportion of participants in clinical response at Week 12 is assumed to be 75% for the combination therapy, which is based on the additive effect from both monotherapies (20% improvement from each monotherapy relative to a historical placebo response of 35%).

Efficacy Analyses

All randomized participants who receive at least 1 dose of study intervention will be included in the efficacy analyses. Participants will be analyzed according to the treatment group to which they were randomized regardless of the treatment they received.

For testing of the primary endpoint, the efficacy of combination therapy versus each monotherapy will be compared. For both statistical comparisons of the primary endpoint, a Cochran-Mantel-Haenszel (CMH) chi-square test stratified by concomitant use of corticosteroids at baseline (Y/N) will be used. The testing will be done simultaneously at the 1-sided 0.1 level of significance for each comparison. The study will be considered positive if the combination therapy group is significantly different from both monotherapy groups for the primary endpoint.

If both tests of the primary endpoint are positive, a CMH chi-square test (1-sided) stratified by concomitant use of corticosteroids at baseline (Y/N) will be used to compare the efficacy of the combination therapy to each monotherapy for the major secondary endpoint. The testing will be done simultaneously at the 1-sided 0.1 level of significance for each comparison.

Analyses for other efficacy endpoints will be performed with no adjustments made for multiple comparisons and nominal p-values will be provided.

Safety Analyses

Safety data, including but not limited to, AEs, serious adverse events (SAEs), infections, serious infections, changes in laboratory assessments, and changes in vital signs will be summarized. Treatment-emergent AEs will be summarized by treatment group and Medical Dictionary for Regulatory Activities (MedDRA) system organ class and preferred terms.

Other Analyses

Pharmacokinetic Analyses

Serum guselkumab and golimumab concentrations over time will be summarized for each treatment group over time using descriptive statistics.

Population PK modeling may be conducted when appropriate. If these population PK analyses are conducted, the results of these analyses will be presented in a separate report.

Immunogenicity Analyses

The incidence of antibodies to guselkumab and to golimumab will be summarized for all participants who receive at least 1 dose of guselkumab or golimumab and have appropriate samples for detection of antibodies to guselkumab and to golimumab (i.e., participants with at least 1 sample obtained after their first dose of guselkumab or golimumab, respectively).

Pharmacokinetic/Pharmacodynamic Analyses

The relationship between serum concentrations of guselkumab and golimumab and the efficacy measures and/or relevant biomarker(s) may be explored graphically when appropriate. Additional analysis may be conducted if deemed necessary.

Biomarkers Analyses

Changes in serum protein analytes, fecal biomarkers, and biopsy and whole blood RNA obtained over time will be summarized by treatment group. Associations between baseline levels and changes from baseline in select markers and response to treatment will be explored. Biomarker analyses will be summarized in a separate technical report.

Pharmacogenomic Analyses

Genetic (DNA) analyses will be conducted only in participants who sign the consent form to participate in the pharmacogenomic sub-study. These analyses are considered exploratory and will be summarized in a separate technical report.

Clinical Results

The study population included 214 randomized participants with moderate-severely active UC (~70 per group). The study population comprises participants who are TNF-naïve and have failed or not tolerated conventional therapy with oral or intravenous (IV) corticosteroids or immunomodulators (6-MP or AZA). The study comprise 12 weeks of combination induction, followed by 26 weeks of monotherapy maintenance. The combination induction doses of guselkumab (GUS) 200 mg IV at Weeks 0, 4, and 8 and golimumab (GOL) 200 mg subcutaneous (SC) at Weeks 0, followed by 100 mg SC at Weeks 2, 6, and 10. Following combination induction, GUS monotherapy is administered as 100 mg SC q8. The same dose regimens as above are used for GUS and GOL monotherapy arms, respectively.

Primary and Major Secondary Endpoints

The primary endpoint of clinical response at Week 12 is defined as a decrease from baseline in the Mayo score≥30% and ≥3 points, with either a decrease in rectal bleeding subscore (RBS)≥1 or RBS of 0 or 1. A major secondary endpoint was clinical remission at Week 12, defined as a Mayo score≤2, with no individual subscore>1. Other efficacy endpoints included (select endpoints with available data noted): (i) endoscopic healing at Week 12 (Mayo endoscopic subscore of 0 or 1), (ii) normalization of endoscopic appearance of the mucosa (Mayo endoscopic subscore of 0), (iii) change from baseline in Mayo score at Week 12, (iv) change from baseline partial Mayo score through Week 12, (v) change from baseline in CRP through Week 12, (vi) change from baseline in fecal calprotectin through Week 12, and normalization of CRP at Week 12 among participants with abnormal CRP concentrations at baseline (same for fecal calprotectin).

Mayo score is incorporated into various definitions of clinical response and remission and is calculated as the sum of 4 subscores (stool frequency, rectal bleeding [RBS], endoscopy, and the Physician's Global Assessment). Clinical response is defined as a decrease from baseline in the Mayo score≥30% and ≥3 points, with a decrease from baseline in the rectal bleeding subscore (RBS) of ≥1 or a RBS of 0 or 1. Clinical remission is defined as a Mayo score≤2, with no individual subscore>1. Clinical remission (Health Authority definition) is defined as a stool frequency subscore of 0 or 1, RBS of 0, and an endoscopy subscore of 0 or 1 with no friability present on endoscopy, where the stool frequency subscore has not increased from baseline. Symptomatic remission is defined as a stool frequency subscore of 0 or 1 and a RBS of 0. Endoscopic healing (i.e., improvement in the endoscopic appearance of the mucosa) is defined as an endoscopy subscore of 0 or 1. Endoscopic healing will be evaluated based on the presence of friability when an endoscopy subscore of 1 is observed.

Conclusions

The 12-week and 24-week data is shown in Tables 4-18 below. This data suggests that combination therapy is superior to either monotherapy. The rates of clinical remission by Health Authority definition (more stringent) and endoscopic healing at Week 12 were nearly double with combination therapy than that observed with either monotherapy. Rapid improvement in multiple parameters was seen with combination therapy. In the context of other currently available advanced therapies in similar biologic-naïve populations, combination therapy confers a numerically higher rate of clinical remission following induction (with numerous caveats re: comparing across studies). At the point of analysis, combination therapy has an acceptable safety profile.

TABLE 4

Summary of Demographics at Baseline; Primary Analysis Set (CNTO1959UCO2002)

|  | Golimumab Monotherapy | Guselkumab Monotherapy | Combination Therapy | Total |
| --- | --- | --- | --- | --- |
| N, Primary Analysis Set | 72 | 71 | 71 | 214 |
| Mean age (SD), years | 38.1 (10.47) | 39.1 (13.67) | 37.8 (11.69) | 38.4 (11.96) |
| Sex, n (%) | | | | |
| Female | 30 (41.7%) | 31 (43.7%) | 37 (52.1%) | 98 (45.8%) |
| Male | 42 (58.3%) | 40 (56.3%) | 34 (47.9%) | 116 (54.2%) |
| Race, White, n (%) | 67 (93.1%) | 71 (100.0%) | 70 (98.6%) | 208 (97.2%) |
| Ethnicity, Not Hispanic or Latino, n (%) | 68 (94.4%) | 65 (91.5%) | 66 (93.0%) | 199 (93.0%) |
| Region [a] n (%) | | | | |
| Eastern Europe [a] | 61 (84.7%) | 58 (81.7%) | 60 (84.5%) | 179 (83.6%) |
| Latin America | 4 (5.6%) | 6 (8.5%) | 7 (9.9%) | 17 (7.9%) |
| Rest of World | 7 (9.7%) | 7 (9.9%) | 4 (5.6%) | 18 (8.4%) |
| Mean weight (SD), kg | 73.9 (17.11) | 69.6 (16.72) | 69.8 (18.79) | 71.1 (17.59) |
| Mean BMI (SD), kg/m$^2$ | 25.0 (5.07) | 23.5 (4.71) | 23.5 (5.05) | 24.0 (4.97) |

[a] Eastern Europe: Poland, Russia, Ukraine; Latin America: Argentina, Mexico, Brazil; Rest of World: United States, Germany, Australia

TABLE 5

Summary of UC Disease Characteristics at Baseline (Mayo Score); Primary Analysis Set (CNTO1959UCO2002)

|  | Golimumab Monotherapy | Guselkumab Monotherapy | Combination Therapy | Total |
| --- | --- | --- | --- | --- |
| N | 72 | 71 | 71 | 214 |
| UC Duration, years (mean [SD]) | 4.7 (4.48) | 5.4 (5.70) | 4.6 (4.61) | 4.9 (4.95) |
| Mayo Score (0-12) (mean [SD]) | 8.7 (1.44) | 8.9 (1.33) | 8.8 (1.37) | 8.8 (1.38) |
| Partial Mayo Score (0-9) (mean [SD]) | 6.2 (1.24) | 6.3 (1.21) | 6.2 (1.13) | 6.2 (1.19) |
| Severity of UC Disease, n (%) | | | | |
| Moderately Active (6 ≤ Mayo Score ≤ 10) | 63 (87.5%) | 64 (90.1%%) | 62 (87.3%) | 189 (88.3%) |
| Severely Active (Mayo Score > 10) | 9 (12.5%) | 7 (9.9%) | 9 (12.7%) | 25 (11.7%) |
| Mayo Endoscopy Subscore (0-3), n (%) | | | | |
| Subscore of 2 (moderate) | 35 (48.6%) | 24 (33.8%) | 28 (39.4%) | 87 (40.7%) |
| Subscore of 3 (severe) | 37 (51.4%) | 47 (66.2%) | 43 (60.6%) | 127 (59.3%) |
| Mayo Stool Frequency Subscore (0-3), n (%) | | | | |
| Subscore of 1 | 12 (16.7%) | 7 (9.9%) | 8 (11.3%) | 27 (12.6%) |
| Subscore of 2 | 27 (37.5%) | 31 (43.7%) | 24 (33.8%) | 82 (38.3%) |
| Subscore of 3 | 33 (45.8%) | 33 (46.4%) | 39 (54.9%) | 105 (49.1%) |

TABLE 6

Number of Participants in Clinical Response at Week 12 (Primary Endpoint); Primary Analysis Set (CNTO1959UCO2002)

|  | Golimumab Monotherapy | Guselkumab Monotherapy | Combination Therapy |
| --- | --- | --- | --- |
| N | 72 | 71 | 71 |
| Participants in clinical response [a,b,c] | 44 (61.1%) | 53 (74.6%) | 59 (83.1%) |
| Adjusted treatment difference (80% 2-sided CI) [d] | 22.1 (12.9, 31.3) | 8.5 (−0.2, 17.1) | |
| p-value [e] | 0.003 | 0.215 | |

[a] Clinical response is defined as a decrease from baseline in the Mayo score ≥30% and ≥3 points with either decrease from baseline in the rectal bleeding subscore (RBS) of ≥1 or a RBS of 0 or 1.
[b] Participants who had an intercurrent event (had an ostomy or colectomy (partial or total), discontinued study intervention due to lack of therapeutic effect or due to an AE of worsening of UC, had a protocol-prohibited change in concomitant UC medication(s), discontinued study intervention for reasons other than lack of efficacy or an AE of worsening of UC, death) prior to the Week 12 visit were considered to not have achieved clinical response at Week 12.
[c] After accounting for intercurrent events, participants who are missing any or all of the Mayo subscores at Week 12 will be considered to not have achieved clinical response at Week 12.
[d] The confidence intervals for the treatment difference in the proportion of participants achieving clinical response between combination therapy versus each monotherapy were based on the Wald statistic.
[e] The p-values were based on the 1-sided Cochran-Mantel-Haenszel (CMH) test, stratified by concomitant use of corticosteroids at baseline (Yes/No).

TABLE 7

Number of Participants in Clinical Remission at Week 12; Primary Analysis Set (CNTO1959UCO2002)

|  | Golimumab Monotherapy | Guselkumab Monotherapy | Combination Therapy |
| --- | --- | --- | --- |
| N | 72 | 71 | 71 |
| Participants in clinical remission [a,b,c] | 16 (22.2%) | 15 (21.1%) | 26 (36.6%) |
| Adjusted treatment difference (80% 2-sided CI) [d] | 14.5 (4.9, 24.0) | 15.5 (6.0, 25.0) | |
| η-value [e] | 0.058 | 0.041 | |

[a] Clinical remission is defined as the Mayo score ≤2 with no individual subscore >1.
[b] Participants who had an intercurrent event (had an ostomy or colectomy (partial or total), discontinued study intervention due to lack of therapeutic effect or due to an AE of worsening of UC, had a protocol-prohibited change in concomitant UC medication(s), discontinued study intervention for reasons other than lack of efficacy or an AE of worsening of UC, death) prior to the Week 12 visit were considered to not have achieved clinical remission at Week 12.
[c] After accounting for intercurrent events, participants who are missing any or all of the Mayo subscores will be considered to not have achieved clinical remission at Week 12.
[d] The confidence intervals for the treatment difference in the proportion of participants achieving clinical remission between combination therapy versus each monotherapy were based on the Wald statistic.
[e] The p-values were based on the 1-sided Cochran-Mantel-Haenszel (CMH) test, stratified by concomitant use of corticosteroids at baseline (Yes/No).

TABLE 8

Number of Participants With Endoscopic Healing at Week 12; Primary Analysis Set (CNTO1959UCO2002)

|  | Golimumab Monotherapy | Guselkumab Monotherapy | Combination Therapy |
| --- | --- | --- | --- |
| N | 72 | 71 | 71 |
| Participants with endoscopic healing [a,b,c] | 18 (25.0%) | 21 (29.6%) | 35 (49.3%) |
| Adjusted treatment difference (80% 2-sided CI) [d] | 24.4 (14.5, 34.3) | 19.7 (9.6, 29.9) | |
| p-value [e] | 0.003 | 0.016 | |

[a] Endoscopic healing is defined as an endoscopy subscore of 0 or 1.

[b] Participants who had an intercurrent event (had an ostomy or colectomy (partial or total), discontinued study intervention due to lack of therapeutic effect or due to an AE of worsening of UC, had a protocol-prohibited change in concomitant UC medication(s), discontinued study intervention for reasons other than lack of efficacy or an AE of worsening of UC, death) prior to the Week 12 visit were considered to not have achieved endoscopic healing at Week 12.

[c] After accounting for intercurrent events, participants who had a missing endoscopy subscore at Week 12 were considered to not have achieved endoscopic healing at Week 12.

[d] The confidence intervals for the treatment difference in the proportion of participants achieving endoscopic healing between combination therapy versus each monotherapy were based on the Wald statistic.

[e] The p-values were based on the 1-sided Cochran-Mantel-Haenszel (CMH) test, stratified by concomitant use of corticosteroids at baseline (Yes/No).

TABLE 9

Number of Participants in Modified Mayo Response at
Week 12; Primary Analysis Set (CNTO1959UCO2002)

|  | Golimumab Monotherapy | Guselkumab Monotherapy | Combination Therapy |
|---|---|---|---|
| N [a] | 42 | 43 | 41 |
| Participants with modified Mayo response [b,c,d] | 24 (57.1%) | 28 (65.1%) | 33 (80.5%) |
| Adjusted treatment difference (80% 2-sided CI) [e] | 23.1 (10.8, 35.4) | 15.4 (3.1, 27.6) |  |
| p-value [f] | 0.023 | 0.119 |  |

[a] Interim data from a subset of participants.
[b] The modified Mayo response is defined as a decrease from baseline in the modified Mayo score of ≥2 and ≥30%, plus a decrease in rectal bleeding subscore of ≥1 or an absolute rectal bleeding subscore of ≤1. The modified Mayo score, which is the Mayo score without the PGA subscore, is calculated as the sum of the stool frequency, rectal bleeding, and endoscopy subscores, and may range from 0 to 9.
[c] Participants who had an intercurrent event (had an ostomy or colectomy (partial or total), discontinued study intervention due to lack of therapeutic effect or due to an AE of worsening of UC, had a protocol-prohibited change in concomitant UC medication(s), discontinued study intervention for reasons other than lack of efficacy or an AE of worsening of UC. death) prior to the Week 12 visit were considered to not have achieved modified Mayo response at Week 12.
[d] After accounting for intercurrent events, participants who are missing any or all of the Mayo subscores that compromise the modified Mayo score (i.e.. stool frequency, rectal bleeding, and endoscopy subscores) will be considered to not have achieved modified Mayo response at Week 12.
[e] The confidence intervals for the treatment difference in the proportion of participants achieving modified Mayo response between combination therapy versus each monotherapy were based on the Wald statistic.
[f] The p-values were based on the 1-sided Cochran-Mantel-Haenszel (CMH) test, stratified by concomitant use of corticosteroids at baseline (Yes/No).

TABLE 10

Number of Participants in Clinical Remission by Health Authority
Definition at Week 12; Primary Analysis Set (CNTO1959UCO2002)

|  | Golimumab Monotherapy | Guselkumab Monotherapy | Combination Therapy |
|---|---|---|---|
| N | 72 | 71 | 71 |
| Participants in clinical remission by Health Authority definition [a,b,c] | 18 (25.0%) | 17 (23.9%) | 33 (46.5%) |
| Adjusted treatment difference (80% 2-sided CI) [d] | 21.6 (11.7, 31.4) | 22.5 (12.7, 32.4) |  |
| p-value [e] | 0.007 | 0.005 |  |

[a] Clinical remission by Health Authority definition is defined as a stool frequency subscore of 0 or 1, rectal bleeding subscore of 0, and an endoscopy subscore of 0 or 1 with no friability present on the endoscopy, where the stool frequency subscore has not increased from baseline.
[b] Participants who had an intercurrent event (had an ostomy or colectomy (partial or total), discontinued study intervention due to lack of therapeutic effect or due to an AE of worsening of UC, had a protocol-prohibited change in concomitant UC medication(s), discontinued study intervention for reasons other than lack of efficacy or an AE of worsening of UC. death) prior to the Week 12 visit were considered to not have achieved clinical remission by Health Authority definition at Week 12.
[c] After accounting for intercurrent events, participants who are missing any or all of the components of the clinical remission by Health Authority definition at Week 12 will be considered to not have achieved clinical remission by Health Authority definition at Week 12.
[d] The confidence intervals for the treatment difference in the proportion of participants achieving clinical remission by Health Authority definition between combination therapy versus each monotherapy were based on the Wald statistic.
[e] The p-values were based on the 1-sided Cochran-Mantel-Haenszel (CMH) test, stratified by concomitant use of corticosteroids at baseline (Yes/No).

TABLE 11

Overall Summary of Treatment-Emergent Adverse Events Through
Week 12; Primary Analysis Set (CNTO1959UCO2002)

|  | Golimumab Monotherapy | Guselkumab Monotherapy | Combination Therapy |
|---|---|---|---|
| N, Primary Analysis Set | 72 | 71 | 71 |
| Avg duration of follow up (weeks) | 12.0 | 12.1 | 12.4 |
| Avg exposure (number of administrations)[a] | 5.8 | 5.8 | 5.9 |
| Participants with ≥1, n (%) |  |  |  |
| Adverse events (AEs) | 38 (52.8%) | 31 (43.7%) | 29 (40.8%) |
| Serious AEs (SAEs) | 1 (1.4%) | 2 (2.8%) | 1 (1.4%) |
| AEs leading to discontinuation of study intervention | 3 (4.2%) | 1 (1.4%) | 2 (2.8%) |
| Infection | 16 (22.2%) | 10 (14.1%) | 10 (14.1%) |

TABLE 11-continued

Overall Summary of Treatment-Emergent Adverse Events Through Week 12; Primary Analysis Set (CNTO1959UCO2002)

|  | Golimumab Monotherapy | Guselkumab Monotherapy | Combination Therapy |
|---|---|---|---|
| Serious infection [b] | 0 | 0 | 1 (1.4%) |
| AEs leading to death | 0 | 0 | 0 |
| One or more AEs associated with COVID-19 infection | 0 | 0 | 1 (1.4%) |

Key: AE = adverse event, Avg = average

Note:
Participants are counted only once for any given event, regardless of the number of times they actually experienced the event. Adverse events are coded using MedDRA Version 21.1.
[a] Average number of visits study intervention received.
[b] Infection as assessed by the investigator.

TABLE 12

Summary of Treatment-Emergent Adverse Events Through Week 12 by MedDRA System-Organ Class and Preferred Term; Primary Analysis Set (CNTO1959UCO2002)

|  | Golimumab Monotherapy | Guselkumab Monotherapy | Combination Therapy |
|---|---|---|---|
| Analysis Set[a]: Primary Analysis Set | 42 | 43 | 41 |
| Avg duration of follow up (weeks) | 12.1 | 12.1 | 12.2 |
| Avg exposure (number of administrations)[b] | 6.0 | 6.0 | 6.0 |
| Participants with 1 or more AEs MedDRA System-Organ Class/Preferred Term | 21 (50.0%) | 22 (51.2%) | 14 (34.1%) |
| Infections and infestations | 10 (23.8%) | 9 (20.9%) | 5 (12.2%) |
| Nasopharyngitis | 3 (7.1%) | 2 (4.7%) | 2 (4.9%) |
| Fungal skin infection | 0 | 0 | 1 (2.4%) |
| Influenza | 1 (2.4%) | 1 (2.3%) | 1 (2.4%) |
| Pharyngitis | 0 | 0 | 1 (2.4%) |
| Rash pustular | 0 | 0 | 1 (2.4%) |
| Sepsis | 0 | 0 | 1 (2.4%) |
| Upper respiratory tract infection | 2 (4.8%) | 3 (7.0%) | 1 (2.4%) |
| Amoebiasis | 1 (2.4%) | 0 | 0 |
| Bronchitis | 1 (2.4%) | 0 | 0 |
| Herpes zoster | 1 (2.4%) | 0 | 0 |
| Impetigo | 0 | 1 (2.3%) | 0 |
| Respiratory tract infection | 0 | 1 (2.3%) | 0 |
| Rhinitis | 1 (2.4%) | 0 | 0 |
| Tracheitis | 0 | 2 (4.7%) | 0 |
| Blood and lymphatic system disorders | 5 (11.9%) | 7 (16.3%) | 4 (9.8%) |
| Anaemia | 3 (7.1%) | 4 (9.3%) | 2 (4.9%) |
| Iron deficiency anaemia | 0 | 0 | 1 (2.4%) |
| Leukopenia | 1 (2.4%) | 2 (4.7%) | 1 (2.4%) |
| Neutropenia | 0 | 4 (9.3%) | 1 (2.4%) |
| Lymphopenia | 2 (4.8%) | 0 | 0 |
| Gastrointestinal disorders | 5 (11.9%) | 6 (14.0%) | 4 (9.8%) |
| Colitis ulcerative | 5 (11.9%) | 1 (2.3%) | 2 (4.9%) |
| Abdominal pain | 0 | 0 | 1 (2.4%) |
| Abdominal pain upper | 0 | 1 (2.3%) | 1 (2.4%) |
| Gingival bleeding | 0 | 0 | 1 (2.4%) |
| Haemorrhoids | 0 | 0 | 1 (2.4%) |
| Nausea | 0 | 1 (2.3%) | 1 (2.4%) |
| Vomiting | 0 | 1 (2.3%) | 1 (2.4%) |
| Dental caries | 0 | 1 (2.3%) | 0 |
| Dyspepsia | 0 | 1 (2.3%) | 0 |
| Hypoaesthesia oral | 0 | 1 (2.3%) | 0 |
| Small intestinal obstruction | 0 | 1 (2.3%) | 0 |
| General disorders and administration site conditions | 2 (4.8%) | 1 (2.3%) | 2 (4.9%) |
| Injection site erythema | 0 | 0 | 1 (2.4%) |
| Non-cardiac chest pain | 0 | 0 | 1 (2.4%) |
| Fatigue | 1 (2.4%) | 0 | 0 |
| Injection site swelling | 0 | 1 (2.3%) | 0 |
| Pyrexia | 1 (2.4%) | 0 | 0 |
| Nervous system disorders | 2 (4.8%) | 4 (9.3%) | 2 (4.9%) |
| Headache | 1 (2.4%) | 1 (2.3%) | 1 (2.4%) |
| Presyncope | 0 | 0 | 1 (2.4%) |

TABLE 12-continued

Summary of Treatment-Emergent Adverse Events Through
Week 12 by MedDRA System-Organ Class and Preferred
Term; Primary Analysis Set (CNTO1959UCO2002)

| | Golimumab Monotherapy | Guselkumab Monotherapy | Combination Therapy |
|---|---|---|---|
| Dizziness | 0 | 1 (2.3%) | 0 |
| Dysgeusia | 0 | 1 (2.3%) | 0 |
| Somnolence | 1 (2.4%) | 1 (2.3%) | 0 |
| Skin and subcutaneous tissue disorders | 0 | 0 | 2 (4.9%) |
| Dermatitis allergic | 0 | 0 | 1 (2.4%) |
| Pyoderma gangrenosum | 0 | 0 | 1 (2.4%) |
| Endocrine disorders | 0 | 0 | 1 (2.4%) |
| Adrenal insufficiency | 0 | 0 | 1 (2.4%) |
| Immune system disorders | 0 | 1 (2.3%) | 1 (2.4%) |
| Seasonal allergy | 0 | 0 | 1 (2.4%) |
| Drug hypersensitivity | 0 | 1 (2.3%) | 0 |
| Musculoskeletal and connective tissue disorders | 2 (4.8%) | 2 (4.7%) | 1 (2.4%) |
| Arthralgia | 1 (2.4%) | 0 | 1 (2.4%) |
| Back pain | 0 | 1 (2.3%) | 0 |
| Bone pain | 1 (2.4%) | 0 | 0 |
| Muscle spasms | 0 | 1 (2.3%) | 0 |
| Myalgia | 1 (2.4%) | 0 | 0 |
| Osteoarthritis | 1 (2.4%) | 0 | 0 |
| Psychiatric disorders | 0 | 0 | 1 (2.4%) |
| Nightmare | 0 | 0 | 1 (2.4%) |
| Reproductive system and breast disorders | 0 | 0 | 1 (2.4%) |
| Endometriosis | 0 | 0 | 1 (2.4%) |
| Cardiac disorders | 0 | 1 (2.3%) | 0 |
| Atrial fibrillation | 0 | 1 (2.3%) | 0 |
| Eye disorders | 0 | 1 (2.3%) | 0 |
| Ocular hyperaemia | 0 | 1 (2.3%) | 0 |
| Hepatobiliary disorders | 1 (2.4%) | 0 | 0 |
| Cholangitis sclerosing | 1 (2.4%) | 0 | 0 |
| Injury, poisoning and procedural complications | 1 (2.4%) | 1 (2.3%) | 0 |
| Contusion | 0 | 1 (2.3%) | 0 |
| Head injury | 1 (2.4%) | 0 | 0 |
| Investigations | 1 (2.4%) | 4 (9.3%) | 0 |
| Alanine aminotransferase increased | 1 (2.4%) | 0 | 0 |
| Aspartate aminotransferase increased | 1 (2.4%) | 0 | 0 |
| Blood alkaline phosphatase increased | 0 | 1 (2.3%) | 0 |
| Blood pressure increased | 0 | 1 (2.3%) | 0 |
| Hepatic enzyme increased | 0 | 1 (2.3%) | 0 |
| Transaminases increased | 0 | 1 (2.3%) | 0 |
| Metabolism and nutrition disorders | 0 | 1 (2.3%) | 0 |
| Hypophosphataemia | 0 | 1 (2.3%) | 0 |
| Respiratory, thoracic and mediastinal disorders | 1 (2.4%) | 1 (2.3%) | 0 |
| Cough | 1 (2.4%) | 0 | 0 |
| Orophaiyngeal pain | 0 | 1 (2.3%) | 0 |

Key: AE = adverse event, Avg = average

Note:

Participants are counted only once for any given event, regardless of the number of times they actually experienced the event. Adverse events are coded using MedDRA Version 21.1.

[a]Interim data from a subset of participants.

[b]Average number of visits study intervention received.

TABLE 13

Number of Participants With Treatment-Emergent Adverse events Leading To Discontinuation of Study Intervention Through Week 12 by MedDRA System-Organ Class and Preferred Term; Primary Analysis Set (CNTO1959UCO2002)

|  | Golimumab Monotherapy | Guselkumab Monotherapy | Combination Therapy |
|---|---|---|---|
| Analysis Set[a]: Primary Analysis Set | 42 | 43 | 41 |
| Avg duration of follow up (weeks) | 12.1 | 12.1 | 12.2 |
| Avg exposure (number of administrations)[b] | 6.0 | 6.0 | 6.0 |
| Participants with treatment-emergent adverse events leading to discontinuation of study intervention MedDRA System-Organ Class/Preferred Term | 2 (4.8%) | 1 (2.3%) | 2 (4.9%) |
| Gastrointestinal disorders | 2 (4.8%) | 1 (2.3%) | 2 (4.9%) |
| Colitis ulcerative | 2 (4.8%) | 0 | 2 (4.9%) |
| Small intestinal obstruction | 0 | 1 (2.3%) | 0 |

Key: Avg = average

Note:

Participants are counted only once for any given event, regardless of the number of times they actually experienced the event. Adverse events are coded using MedDRA Version 21.1.

[a]Interim data from a subset of participants.

[b]Average number of visits study intervention received.

TABLE 14

Number of Participants With 1 or More Treatment-Emergent Serious Infections Through Week 12 by MedDRA System-Organ Class and Preferred Term; Primary Analysis Set (CNTO1959UCO2002)

|  | Golimumab Monotherapy | Guselkumab Monotherapy | Combination Therapy |
|---|---|---|---|
| Analysis Set[a]: Primary Analysis Set | 42 | 43 | 41 |
| Avg duration of follow up (weeks) | 12.1 | 12.1 | 12.2 |
| Avg exposure (number of administrations)[b] | 6.0 | 6.0 | 6.0 |
| Participants with 1 or more AEs of serious infection [c] MedDRA System-Organ Class/Preferred Term | 0 | 0 | 1 (2.4%) |
| Infections and infestations | 0 | 0 | 1 (2.4%) |
| Influenza | 0 | 0 | 1 (2.4%) |
| Sepsis | 0 | 0 | 1 (2.4%) |

Key: Avg = average

Note:

Participants are counted only once for any given event, regardless of the number of times they actually experienced the event. Adverse events are coded using MedDRA Version 21.1.

[a]Interim data from a subset of participants.

[b]Average number of visits study intervention received.

[c] Serious infection as assessed by the investigator.

TABLE 15

Overall Summary of Treatment-Emergent Adverse Events Through Week 24; Full Analysis Set (CNTO1959UCO2002)

|  | Golimumab Monotherapy | Guselkumab Monotherapy | Combination Therapy [d] |
|---|---|---|---|
| Analysis Set[a]: Full Analysis Set | 55 | 55 | 58 |
| Avg duration of follow up (weeks) | 19.3 | 19.6 | 18.5 |
| Avg exposure (number of administrations)[b] | 8.9 | 9.1 | 8.4 |
| Participants with 1 or more AEs | 31 (56.4%) | 29 (52.7%) | 28 (48.3%) |
| Participants with 1 or more serious AEs | 2 (3.6%) | 2 (3.6%) | 2 (3.4%) |
| Participants with 1 or more AEs leading to discontinuation of study intervention | 3 (5.5%) | 1 (1.8%) | 5 (8.6%) |
| Participants with 1 or more AEs of infection [c] | 15 (27.3%) | 12 (21.8%) | 11 (19.0%) |
| Participants with 1 or more AEs of serious infection [c] | 0 | 0 | 2 (3.4%) |

Key: AE = adverse event, Avg = average

Note:

Participants are counted only once for any given event, regardless of the number of times they actually experienced the event. Adverse events are coded using MedDRA Version 21.1.

[a]Interim data from a subset of participants.

[b]Average number of visits study intervention received.

[c] Infection as assessed by the investigator.

[d] Participants in the combination therapy group switched to guselkumab monotherapy beginning at Week 12.

TABLE 16

Number of Participants With Treatment-Emergent Adverse Events Leading to Discontinuation of Study Intervention Through Week 24 by MedDRA System-Organ Class and Preferred Term; Full Analysis Set (CNTO1959UCO2002)

|  | Golimumab Monotherapy | Guselkumab Monotherapy | Combination Therapy [c] |
|---|---|---|---|
| Analysis Set[a]: Full Analysis Set | 55 | 55 | 58 |
| Avg duration of follow up (weeks) | 19.3 | 19.6 | 18.5 |
| Avg exposure (number of administrations)[b] | 8.9 | 9.1 | 8.4 |
| Participants with treatment-emergent adverse events leading to discontinuation of study intervention | 3 (5.5%) | 1 (1.8%) | 5 (8.6%) |

TABLE 16-continued

Number of Participants With Treatment-Emergent Adverse Events Leading to Discontinuation of Study Intervention Through Week 24 by MedDRA System-Organ Class and Preferred Term; Full Analysis Set (CNTO1959UCO2002)

| | Golimumab Monotherapy | Guselkumab Monotherapy | Combination Therapy [c] |
|---|---|---|---|
| MedDRA System-Organ Class/Preferred Term | | | |
| Gastrointestinal disorders | 2 (3.6%) | 1 (1.8%) | 3 (5.2%) |
| Colitis ulcerative | 2 (3.6%) | 0 | 3 (5.2%) |
| Small intestinal obstruction | 0 | 1 (1.8%) | 0 |
| Infections and infestations | 0 | 0 | 2 (3.4%) |
| Cytomegalovirus colitis | 0 | 0 | 1 (1.7%) |
| Extrapulmonary tuberculosis | 0 | 0 | 1 (1.7%) |
| Respiratory, thoracic and mediastinal disorders | 1 (1.8%) | 0 | 0 |
| Pulmonary embolism | 1 (1.8%) | 0 | 0 |

Key: Avg = average

Note: Participants are counted only once for any given event, regardless of the number of times they actually experienced the event. Adverse events are coded using MedDRA Version 21.1.

[a] Interim data from a subset of parcitipants.

[b] Average number of visits study intervention received.

[c] Participants in the combination therapy group switched to guselkumab monotherapy beginning at Week 12.

TABLE 17

Number of Participants With Treatment-Emergent Serious Adverse Events Through Week 24 by MedDRA System-Organ Class and Preferred Term; Full Analysis Set (CNTO1959UCO2002)

| | Golimumab Monotherapy | Guselkumab Monotherapy | Combination Therapy [c] |
|---|---|---|---|
| Analysis Set[a]: Full Analysis Set | 55 | 55 | 58 |
| Avg duration of follow up (weeks) | 19.3 | 19.6 | 18.5 |
| Avg exposure (number of administrations)[b] | 8.9 | 9.1 | 8.4 |
| Participants with 1 or more treatment-emergent serious adverse events | 2 (3.6%) | 2 (3.6%) | 2 (3.4%) |
| MedDRA System-Organ Class/Preferred Term | | | |
| Infections and infestations | 0 | 0 | 2 (3.4%) |
| Extrapulmonary tuberculosis | 0 | 0 | 1 (1.7%) |
| Influenza | 0 | 0 | 1 (1.7%) |
| Sepsis | 0 | 0 | 1 (1.7%) |
| Respiratory, thoracic and mediastinal disorders | 1 (1.8%) | 0 | 1 (1.7%) |
| Pulmonary embolism | 1 (1.8%) | 0 | 1 (1.7%) |
| Cardiac disorders | 0 | 1 (1.8%) | 0 |
| Atrial fibrillation | 0 | 1 (1.8%) | 0 |
| Gastrointestinal disorders | 1 (1.8%) | 1 (1.8%) | 0 |
| Colitis ulcerative | 1 (1.8%) | 0 | 0 |
| Small intestinal obstruction | 0 | 1 (1.8%) | 0 |

Key: Avg = average

Note:

Participants are counted only once for any given event, regardless of the number of times they actually experienced the event. Adverse events are coded using MedDRA Version 21.1.

[a] Interim data from a subset of participants.

[b] Average number of visits study intervention received.

[c] Participants in the combination therapy group switched to guselkumab monotherapy beginning at Week 12.

TABLE 18

Number of Participants With 1 or More Treatment-Emergent Serious Infections Through Week 24 by MedDRA System-Organ Class and Preferred Term; Full Analysis Set (CNTO1959UCO2002)

|  | Golimumab Monotherapy | Guselkumab Monotherapy | Combination Therapy [d] |
|---|---|---|---|
| Analysis Set[a]: Full Analysis Set | 55 | 55 | 58 |
| Avg duration of follow up (weeks) | 19.3 | 19.6 | 18.5 |
| Avg exposure (number of administrations)[b] | 8.9 | 9.1 | 8.4 |
| Participants with 1 or more AEs of serious infection [c] MedDRA System-Organ Class/Preferred Term | 0 | 0 | 2 (3.4%) |
| Infections and infestations | 0 | 0 | 2 (3.4%) |
| Extrapulmonary tuberculosis | 0 | 0 | 1 (1.7%) |
| Influenza | 0 | 0 | 1 (1.7%) |
| Sepsis | 0 | 0 | 1 (1.7%) |

Key: Avg = average
Note:
Participants are counted only once for any given event, regardless of the number of times they actually experienced the event. Adverse events are coded using MedDRA Version 21.1.
[a] Interim data from a subset of participants.
[b] Average number of visits study intervention received.
[c] Infection as assessed by the investigator.
[d] Participants in the combination therapy group switched to guselkumab monotherapy beginning at Week 12.

The present application describes a number of examples and embodiments of the invention. Nevertheless, it must be borne in mind that various modifications of the described examples and embodiments can be developed, while not departing from the scope and the essence of the invention in principle. With this in mind, other embodiments are included in the scope of the items listed below. At that, all the numerical ranges described herein include all the sub ranges contained therein, as well as any individual values within the scope of these ranges. All publications, patents and patent applications mentioned in this description are hereby incorporated by reference.

The Invention can be Described with Reference to the Following Numbered Embodiments:

1. An IL-23 inhibitor and a TNF-α inhibitor for use in the treatment of an inflammatory disease in a patient, wherein the inhibitors are in co-therapeutically effective and clinically safe amounts and the patient shows a clinical response.
2. An IL-23 inhibitor and a TNF-α inhibitor for use according to embodiment 1, wherein the inflammatory disease is an inflammatory bowel disease and the patient shows a clinical response based on a clinical endpoint selected from the group consisting of Mayo score, partial Mayo score, Ulcerative Colitis Endoscopic Index of Severity (UCEIS), the markers CRP and/or fecal calprotectin and patient-reported outcome and symptom measures.
3. An IL-23 inhibitor and a TNF-α inhibitor for use according to any one of the preceding embodiments, wherein the IL-23 inhibitor comprises an anti-IL-23p19 antibody or an antigen-binding fragment thereof and the TNF-α inhibitor comprises an anti-TNF-α antibody or an antigen-binding fragment thereof.
4. An IL-23 inhibitor and a TNF-α inhibitor for use according to any one of the preceding embodiments, wherein the inflammatory bowel disease is Crohn's disease.
5. An IL-23 inhibitor and a TNF-α inhibitor for use according to any one of the preceding embodiments, wherein the inflammatory bowel disease is ulcerative colitis (UC) or indeterminate colitis.
6. An IL-23 inhibitor and a TNF-α inhibitor for use according to any one of the preceding embodiments, wherein the inflammatory bowel disease is moderately to severely active ulcerative colitis (UC).
7. An IL-23 inhibitor and a TNF-α inhibitor for use according to any one of the preceding embodiments, wherein the patient was previously treated with a TNF-α inhibitor alone and wherein the UC did not undergo remission after the previous treatment.
8. An IL-23 inhibitor and a TNF-α inhibitor for use according to any one of the preceding embodiments, wherein the patient was previously treated with an IL-23 inhibitor alone and wherein the UC did not undergo remission after the previous treatment.
9. An IL-23 inhibitor and a TNF-α inhibitor for use according to any one of the preceding embodiments, wherein the anti-IL-23p19 antibody comprises: a) heavy chain complementarity determining region (CDR) amino acid sequences of SEQ ID NOS:1-3 and light chain CDR amino acid sequences of SEQ ID NOS: 4-6; b) a heavy chain variable region amino acid sequence of SEQ ID NO:7 and a light chain variable region amino acid sequence of SEQ ID NO: 8; or c) a heavy chain amino acid sequence of SEQ ID NO:9 and a light chain amino acid sequence of SEQ ID NO:10.
10. An IL-23 inhibitor and a TNF-α inhibitor for use according to any one of the preceding embodiments, wherein the anti-TNFα antibody comprises: a) heavy chain CDR amino acid sequences of SEQ ID NOS:11-13 and light chain CDR amino acid sequences of SEQ ID NOS: 14-16; b) a heavy chain variable region amino acid sequence of SEQ ID NO:17 and a light chain variable region amino acid sequence of SEQ ID NO:18; or c) a heavy chain amino acid sequence of SEQ ID NO:19 and a light chain amino acid sequence of SEQ ID NO:20.
11. An IL-23 inhibitor and a TNF-α inhibitor for use according to any one of the preceding embodiments, wherein the anti-IL-23p19 antibody comprises: a) heavy chain complementarity determining region (CDR) amino acid sequences of SEQ ID NOS:1-3 and light chain CDR amino acid sequences of SEQ ID NOS: 4-6; b) a heavy chain variable region amino acid sequence of SEQ ID NO:7 and a light chain variable region amino acid sequence of SEQ ID NO: 8; or c) a heavy chain amino acid sequence of SEQ ID NO:9 and a light chain amino acid sequence of SEQ ID NO:10, and the anti-TNFα antibody comprises: a) heavy chain CDR amino acid sequences of SEQ ID NOS:11-13 and light chain CDR amino acid sequences of SEQ ID NOS: 14-16; b) a heavy chain variable region amino acid sequence of SEQ ID NO:17 and a light chain variable region amino acid sequence of SEQ ID NO:18; or c) a heavy chain amino acid sequence of SEQ ID NO:19 and a light chain amino acid sequence of SEQ ID NO:20.
12. An anti-IL-23 antibody or fragment thereof and an anti-TNF-α antibody or fragment thereof for use in the treatment of ulcerative colitis in a patient, wherein the anti-IL-23p19 antibody comprises: (i) the heavy chain complementarity determining region (CDR) amino acid sequences of SEQ ID NOS:1-3 and the light chain CDR amino acid sequences of SEQ ID NOS: 4-6, (ii)

the heavy chain variable region amino acid sequence of SEQ ID NO:7 and the light chain variable region amino acid sequence of SEQ ID NO: 8, or (iii) the heavy chain amino acid sequence of SEQ ID NO:9 and the light chain amino acid sequence of SEQ ID NO:10; and the anti-TNF-α antibody comprises (i) the heavy chain CDR amino acid sequences of SEQ ID NOS:11-13 and the light chain CDR amino acid sequences of SEQ ID NOS: 14-16, (ii) the heavy chain variable region amino acid sequence of SEQ ID NO:17 and the light chain variable region amino acid sequence of SEQ ID NO:18, or (iii) the heavy chain amino acid sequence of SEQ ID NO:19 and the light chain amino acid sequence of SEQ ID NO:20, wherein the antibodies are in co-therapeutically effective and clinically safe amounts and the use is effective to treat ulcerative colitis and the patient shows a clinical response based on a clinical endpoint selected from the group consisting of Mayo score, partial Mayo score, Ulcerative Colitis Endoscopic Index of Severity (UCEIS), the markers CRP and/or fecal calprotectin and patient-reported outcome and symptom measures.

13. An anti-IL-23 antibody and an anti-TNF-α antibody for use according to embodiment 12, wherein the anti-TNFα antibody and the anti-IL-23p19 antibody are administered in a ratio of from 1:2 to 2:1 (w/w).

14. An anti-IL-23 antibody and an anti-TNF-α antibody for use according to embodiments 12 or 13, wherein the anti-TNFα antibody and the anti-IL-23p19 antibody are administered in a ratio of from 15:1 to 400:1 (w/w).

15. An anti-IL-23 antibody and an anti-TNF-α antibody for use according to any of embodiments 12-14, wherein the anti-IL-23p19 antibody and the anti-TNF-α antibody are administered simultaneously.

16. An anti-IL-23 antibody and an anti-TNF-α antibody for use according to any of embodiments 12-14, wherein the anti-IL-23p19 antibody and the anti-TNF-α antibody are administered sequentially.

17. An anti-IL-23 antibody and an anti-TNF-α antibody for use according to any of embodiments 12-14 and 16, wherein the anti-IL-23p19 antibody and the anti-TNF-α antibody are administered within one day of one another.

18. An anti-IL-23 antibody and an anti-TNF-α antibody for use according to any of embodiments 12-17, wherein the anti-IL-23p19 antibody is administered in an initial intravenous dose of 200 mg, intravenous doses of 200 mg at weeks 4 and 8 and subsequent subcutaneous doses of 100 mg every 8 weeks and the anti-TNF-α antibody is administered in an initial subcutaneous dose of 200 mg and subsequent subcutaneous doses of 100 mg at weeks 2, 6 and 10.

19. An anti-IL-23 antibody and an anti-TNF-α antibody for use according to any of embodiments 12-18, wherein the patient shows a clinical remission based on a clinical endpoint selected from the group consisting of Mayo score, partial Mayo score, Ulcerative Colitis Endoscopic Index of Severity (UCEIS), the markers CRP and/or fecal calprotectin and patient-reported outcome and symptom measures.

20. An anti-IL-23 antibody and an anti-TNF-α antibody for use according to embodiment 19, wherein the clinical endpoint is measured about 12 weeks after initial treatment.

21. An anti-IL-23 antibody and an anti-TNF-α antibody for use according to embodiments 19 or 20, wherein the clinical endpoint is based on the Mayo Score.

22. An anti-IL-23 antibody or fragment thereof and an anti-TNF-α antibody or fragment thereof for use in reducing inflammation of the colon in a patient with inflammatory bowel disease, wherein the antibodies are in co-therapeutically effective and clinically safe amounts and the use is effective to reduce inflammation of the colon of the patient to a level comparable to the colon of a normal subject.

23. An anti-IL-23 antibody and an anti-TNF-α antibody for use according to embodiment 22, wherein the inflammation is very minimal or normal in a tissue sample from the colon of the patient after administration of the anti-IL-23p19 antibody or antigen-binding fragment thereof and the anti-TNF-α antibody or antigen-binding fragment thereof.

24. An anti-IL-23 antibody and an anti-TNF-α antibody for use according to embodiment 22, wherein gland loss is very minimal or normal in a tissue sample from the colon of the subject after administration of the anti-IL-23p19 antibody or antigen-binding fragment thereof and the anti-TNF-α antibody or antigen-binding fragment thereof.

25. An anti-IL-23 antibody and an anti-TNF-α antibody for use according to embodiment 22, wherein erosion is very minimal or normal in a tissue sample from the colon of the subject after administration of the anti-IL-23p19 antibody or antigen-binding fragment thereof and the anti-TNF-α antibody or antigen-binding fragment thereof.

26. An anti-IL-23 antibody and an anti-TNF-α antibody for use according to embodiment 22, wherein mucosal thickness and hyperplasia are independently very minimal or normal in a tissue sample from the colon of the subject after administration of the anti-IL-23p19 antibody or antigen-binding fragment thereof and the anti-TNF-α antibody or antigen-binding fragment thereof.

27. An anti-IL-23 antibody and an anti-TNF-α antibody for use according to embodiment 22, wherein after administration of the anti-IL-23p19 antibody or antigen-binding fragment thereof and the anti-TNF-α antibody or antigen-binding fragment thereof, histopathology of the colon is identical to that of normal tissue.

28. An anti-IL-23 antibody and an anti-TNF-α antibody for use according to any of embodiments 22-27, wherein the anti-IL-23p19 antibody or antigen-binding fragment thereof comprises: a) the heavy chain CDR amino acid sequences of SEQ ID NOS:1-3 and the light chain CDR amino acid sequences of SEQ ID NOS: 4-6; b) the heavy chain variable region amino acid sequence of SEQ ID NO:7 and the light chain variable region amino acid sequence of SEQ ID NO: 8; or c) the heavy chain amino acid sequence of SEQ ID NO:9 and the light chain amino acid sequence of SEQ ID NO: 10; and the anti-TNF-α antibody or antigen-binding fragment thereof comprises d) the heavy chain CDR amino acid sequences of SEQ ID NOS:11-13 and the light chain CDR amino acid sequences of SEQ ID NOS:14-16; e) the heavy chain variable region amino acid sequence of SEQ ID NO:17 and the light chain variable region amino acid sequence of SEQ ID NO:18; or f) the heavy chain amino acid sequence of SEQ ID NO:19 and the light chain amino acid sequence of SEQ ID NO:20.

29. An anti-IL-23 antibody and an anti-TNF-α antibody for use according to any of embodiments 22-28, wherein the anti-TNFα antibody or antigen-binding fragment thereof and the anti-IL-23p19 antibody or antigen-binding fragment thereof are administered in a ratio of from 1:2 to 2:1 (w/w).
30. An anti-IL-23 antibody and an anti-TNF-α antibody for use according to any of embodiments 22-28, wherein the anti-TNFα antibody or antigen-binding fragment thereof and the anti-IL-23p19 antibody or antigen-binding fragment thereof are administered in a ratio of from 15:1 to 400:1 (w/w).
31. An anti-IL-23 antibody and an anti-TNF-α antibody for use according to any of embodiments 22-30, wherein the a) anti-IL-23p19 antibody or antigen-binding fragment thereof and the b) anti-TNF-α antibody or antigen-binding fragment thereof are administered simultaneously.
32. An anti-IL-23 antibody and an anti-TNF-α antibody for use according to any of embodiments 22-30, wherein the a) anti-IL-23p19 antibody or antigen-binding fragment thereof and the b) anti-TNF-α antibody or antigen-binding fragment thereof are administered sequentially.
33. An anti-IL-23 antibody and an anti-TNF-α antibody for use according to any of embodiments 22-30, wherein the a) anti-IL-23p19 antibody or antigen-binding fragment thereof and the b) anti-TNF-α antibody or antigen-binding fragment thereof are administered within one day of one another.
34. An anti-IL-23 antibody or fragment thereof and an anti-TNF-α antibody or fragment thereof for use in treating inflammatory bowel disease in a patient and reducing weight loss in the patient and being clinically safe.
35. An anti-IL-23 antibody or antigen-binding fragment thereof and an anti-TNF-α antibody or antigen-binding fragment thereof for use according to embodiment 34, wherein the anti-TNFα antibody or antigen-binding fragment thereof and the anti-IL-23p19 antibody or antigen-binding fragment thereof are administered in a ratio of from 15:1 to 400:1 (w/w).
36. An anti-IL-23 antibody or antigen-binding fragment thereof and an anti-TNF-α antibody or antigen-binding fragment thereof for use according to embodiments 34 or 35, wherein the a) anti-IL-23p19 antibody or antigen-binding fragment thereof and the b) anti-TNF-α antibody or antigen-binding fragment thereof are administered simultaneously.
37. An anti-IL-23 antibody or antigen-binding fragment thereof and an anti-TNF-α antibody or antigen-binding fragment thereof for use according to embodiments 34 or 35, wherein the a) anti-IL-23p19 antibody or antigen-binding fragment thereof and the b) anti-TNF-α antibody or antigen-binding fragment thereof are administered sequentially.
38. An anti-IL-23 antibody or antigen-binding fragment thereof and an anti-TNF-α antibody or antigen-binding fragment thereof for use according to any of embodiments 34, 35 or 37, wherein the a) anti-IL-23p19 antibody or antigen-binding fragment thereof and the b) anti-TNF-α antibody or antigen-binding fragment thereof are administered within one day of one another.
39. An anti-IL-23 antibody or antigen-binding fragment thereof and an anti-TNF-α antibody or antigen-binding fragment thereof for use according to any of embodiments 34-38, wherein the anti-IL-23p19 antibody or antigen-binding fragment thereof comprises: a) the heavy chain CDR amino acid sequences of SEQ ID NOS:1-3 and the light chain CDR amino acid sequences of SEQ ID NOS: 4-6; b) the heavy chain variable region amino acid sequence of SEQ ID NO:7 and the light chain variable region amino acid sequence of SEQ ID NO: 8; or c) the heavy chain amino acid sequence of SEQ ID NO:9 and the light chain amino acid sequence of SEQ ID NO: 10; and the anti-TNF-α antibody or antigen-binding fragment thereof comprises d) the heavy chain CDR amino acid sequences of SEQ ID NOS:11-13 and the light chain CDR amino acid sequences of SEQ ID NOS:14-16; e) the heavy chain variable region amino acid sequence of SEQ ID NO:17 and the light chain variable region amino acid sequence of SEQ ID NO:18; or f) the heavy chain amino acid sequence of SEQ ID NO:19 and the light chain amino acid sequence of SEQ ID NO:20.
40. An anti-IL-23 antibody or fragment thereof and an anti-TNF-α antibody or fragment thereof for use in treating moderately to severely active ulcerative colitis in a human patient, wherein the anti-IL-23p19 antibody or an antigen-binding fragment thereof is administered at 0.0005 to 0.002 mg/kg and comprises the sequences of (i) the heavy chain CDR amino acid sequences of SEQ ID NOS:1-3 and the light chain CDR amino acid sequences of SEQ ID NOS: 4-6; (ii) the heavy chain variable region amino acid sequence of SEQ ID NO:7 and the light chain variable region amino acid sequence of SEQ ID NO: 8; or (iii) the heavy chain amino acid sequence of SEQ ID NO:9 and the light chain amino acid sequence of SEQ ID NO:10 and the anti-TNF-α antibody or an antigen-binding fragment thereof is administered at 0.020 to 0.125 mg/kg and comprises the sequences of (iv) the heavy chain CDR amino acid sequences of SEQ ID NOS:11-13 and the light chain CDR amino acid sequences of SEQ ID NOS:14-16; (v) the heavy chain variable region amino acid sequence of SEQ ID NO:17 and the light chain variable region amino acid sequence of SEQ ID NO:18; or (vi) the heavy chain amino acid sequence of SEQ ID NO:19 and the light chain amino acid sequence of SEQ ID NO:20.
41. An anti-IL-23 antibody or antigen-binding fragment thereof and an anti-TNF-α antibody or antigen-binding fragment thereof for use according to embodiment 40, wherein the use is effective and clinically safe to treat the ulcerative colitis.
42. An anti-IL-23 antibody or antigen-binding fragment thereof and an anti-TNF-α antibody or antigen-binding fragment thereof for use according to embodiments 40 or 41, wherein the patient shows a clinical remission based on a clinical endpoint selected from the group consisting of Mayo score, partial Mayo score, Ulcerative Colitis Endoscopic Index of Severity (UCEIS), the markers CRP and/or fecal calprotectin and patient-reported outcome and symptom measures.
43. An anti-IL-23 antibody or antigen-binding fragment thereof and an anti-TNF-α antibody or antigen-binding fragment thereof for use according to any of embodiments 40-42, wherein the anti-IL-23p19 antibody is in an aqueous solution in a pharmaceutical composition at 100 mg/mL; 7.9% (w/v) sucrose, 4.0 mM Histidine, 6.9 mM L-Histidine monohydrochloride monohydrate; 0.053% (w/v) Polysorbate 80 of the composition, and the anti-TNF-α antibody is in an aqueous solution in a pharmaceutical composition at 100 mg/mL; 4.1% (w/v) sorbitol, 5.6 mM L-Histidine and L-Histidine monohydrochloride monohydrate; 0.015% (w/v) Polysorbate 80 of the composition.

44. An anti-IL-23p19 antibody or antigen-binding fragment thereof for use in treating ulcerative colitis in a patient, wherein a therapeutically effective and clinically safe amount of the anti-IL-23p19 antibody or antigen-binding fragment thereof is administered.
45. An anti-IL-23p19 antibody or antigen-binding fragment thereof for use according to embodiment 44, wherein the anti-IL-23p19 antibody or antigen-binding fragment thereof comprises: a) heavy chain complementarity determining region (CDR) amino acid sequences of SEQ ID NOS:1-3 and light chain CDR amino acid sequences of SEQ ID NOS: 4-6; b) a heavy chain variable region amino acid sequence of SEQ ID NO:7 and a light chain variable region amino acid sequence of SEQ ID NO: 8; or c) a heavy chain amino acid sequence of SEQ ID NO:9 and a light chain amino acid sequence of SEQ ID NO:10.
46. An anti-IL-23p19 antibody or antigen-binding fragment thereof for use according to embodiment 44 or 45, wherein the anti-IL-23p19 antibody or antigen-binding fragment thereof is guselkumab.
47. An anti-IL-23p19 antibody or antigen-binding fragment thereof for use according to any of embodiments 44-46, wherein the anti-IL-23p19 antibody or antigen-binding fragment thereof is administered in an initial dose of 200 mg, 600 mg or 1200 mg and a dose of 100 mg 2 weeks after the initial dose, 6 weeks after the initial dose, 10 weeks after the initial dose and every 4 or 8 weeks after the dose at 10 weeks.
48. An anti-IL-23p19 antibody or antigen-binding fragment thereof for use according to any of embodiments 44-47, wherein the patient shows a clinical response based on a clinical endpoint selected from the group consisting of Mayo score, partial Mayo score, Ulcerative Colitis Endoscopic Index of Severity (UCEIS), the markers CRP and/or fecal calprotectin and patient-reported outcome and symptom measures.

The invention claimed is:

1. A method comprising:
   a) administering to a group of patients with ulcerative colitis a first co-therapeutically effective amount of an anti-IL-23p19 antibody comprising (i) the heavy chain complementarity determining region (CDR) amino acid sequences of SEQ ID NOS: 1-3 and the light chain CDR amino acid sequences of SEQ ID NOS: 4-6, (ii) the heavy chain variable region amino acid sequence of SEQ ID NO: 7 and the light chain variable region amino acid sequence of SEQ ID NO: 8, or (iii) the heavy chain amino acid sequence of SEQ ID NO: 9 and the light chain amino acid sequence of SEQ ID NO: 10;
   b) administering to the group of patients with ulcerative colitis a second co-therapeutically effective amount of anti-TNF-α antibody comprising (i) the heavy chain CDR amino acid sequences of SEQ ID NOS: 11-13 and the light chain CDR amino acid sequences of SEQ ID NOS: 14-16, (ii) the heavy chain variable region amino acid sequence of SEQ ID NO: 17 and the light chain variable region amino acid sequence of SEQ ID NO: 18, or (iii) the heavy chain amino acid sequence of SEQ ID NO: 19 and the light chain amino acid sequence of SEQ ID NO: 20,
   wherein the anti-TNF-α antibody and the anti-IL-23p19 antibody are administered in a ratio of from 1:2 to 2:1 (w/w); and
   c) achieving one or more of the following clinical endpoints at week 12:
      i. greater than 83 % of patients are in clinical response defined as a decrease from baseline in the Mayo score %≥30% and ≥3 points with either decrease form baseline in the rectal bleeding subscore (RBS) of ≥1 or a RBS of 0 or 1;
      ii. greater that 36% of patients are in clinical remission defined as the Mayo score≤2 with no individual subscore>1;
      iii. greater than 49% of patients have endoscopic healing defined as an endoscopy score of 0 or 1;
      iv. greater than 80 % of patients have a modified Mayo response defined as a decrease form baseline in the modified Mayo score of ≥2 and ≥30%, plus a decrease in rectal bleeding subscore of ≥1 or an absolute rectal bleeding subscore of ≤1, wherein the modified Mayo score is calculated as the sub of the stool frequency, rectal bleeding, and endoscopy subscores; and
      v. greater than 46% of patients are in clinical remission by health authority definition defined as a stool frequency subscore of 0 or 1, rectal bleeding subscore of 0, and an endoscopy subscore of 0 or 1 with no friability present on the endoscopy, where the stool frequency subscore has not increased from baseline.

2. The method of claim 1, wherein the anti-IL-23p19 antibody and the anti-TNF-α antibody are administered simultaneously.

3. The method of claim 1, wherein the anti-IL-23p19 antibody and the anti-TNF-α antibody are administered sequentially.

4. The method of claim 1, wherein the anti-IL-23p19 antibody and the anti-TNF-α antibody are administered within one day of one another.

5. The method of claim 1, wherein the anti-IL-23p19 antibody is administered in an initial intravenous dose of 200 mg, intravenous doses of 200 mg at weeks 4 and 8 and subsequent subcutaneous doses of 100 mg every 8 weeks and the anti-TNF-α antibody is administered in an initial subcutaneous dose of 200 mg and subsequent subcutaneous doses of 100 mg at weeks 2, 6 and 10.

6. The method of claim 1, wherein the anti-IL-23p19 antibody is in a pharmaceutical composition comprising a solution comprising 7.9% (w/v) sucrose, 4.0 mM Histidine, 6.9 mM L-Histidine monohydrochloride monohydrate, and 0.053% (w/v) Polysorbate 80 of the composition, and wherein the anti-TNF-α antibody is in a pharmaceutical composition comprising a solution comprising 4.1% (w/v) sorbitol, 5.6 mM L-Histidine and L-Histidine monohydrochloride monohydrate, and 0.015% (w/v) Polysorbate 80 of the composition.

7. A method comprising:
   a) administering to a patient with ulcerative colitis a first co-therapeutically effective amount of an anti-IL-23p19 antibody comprising (i) a heavy chain variable region amino acid sequence of SEQ ID NO: 7 and a light chain variable region amino acid sequence of SEQ ID NO: 8, or (ii) a heavy chain amino acid sequence of SEQ ID NO: 9 and a light chain amino acid sequence of SEQ ID NO: 10;
   b) administering to the patient with ulcerative colitis a second co-therapeutically effective amount of an anti-TNF-α antibody comprising (i) a heavy chain variable region amino acid sequence of SEQ ID NO: 17 and a light chain variable region amino acid sequence of SEQ ID NO: 18, or (ii) a heavy chain amino acid sequence of SEQ ID NO: 19 and a light chain amino acid sequence of SEQ ID NO: 20, wherein the anti-TNF-α antibody and the anti-IL-23p19 antibody are administered simultaneously and in a ratio of from 1:2 to 2:1 (w/w); and c) achieving one or more of the following clinical endpoints at week 12;
  i. clinical response defined as a decrease from baseline in the Mayo score≥30% and ≥3 points with either decrease from baseline in the rectal bleeding subscore (RBS) of ≥1 or a RBS of 0 or 1;
  ii. clinical remission defined as the Mayo score≤2 with no individual subscore>1;
  iii. endoscopic healing defined as an endoscopy score of 0 or 1;
  iv. modified Mayo response defined as a decrease from baseline in the modified Mayo score of ≥2 and ≥30%, plus a decrease in rectal bleeding subscore of ≥1 or an absolute rectal bleeding subscore of ≤1, wherein the modified Mayo score is calculated as the sum of the stool frequency, rectal bleeding, and endoscopy subscores; and
  v. clinical remission by health authority definition defined as a stool frequency subscore of 0 or 1, rectal bleeding subscore of 0, and an endoscopy subscore of 0 or 1 with no friability present on the endoscopy, wherein the stool frequency subscore has not increased from baseline.

* * * * *